United States Patent
Tagaya et al.

(10) Patent No.: US 12,030,936 B2
(45) Date of Patent: Jul. 9, 2024

(54) MODULATING THE EFFECTS OF GAMMA-C-CYTOKINE SIGNALING FOR THE TREATMENT OF ALOPECIA AND ALOPECIA ASSOCIATED DISORDERS

(71) Applicant: BIONIZ THERAPEUTICS, LLC, La Jolla, CA (US)

(72) Inventors: Yutaka Tagaya, Rockville, MD (US); Nazli Azimi, San Juan Capistrano, CA (US)

(73) Assignee: BIONIZ THERAPEUTICS, INC., La Jolla, CA (US)

( * ) Notice: Subject to any disclaimer, the term of this patent is extended or adjusted under 35 U.S.C. 154(b) by 426 days.

(21) Appl. No.: 16/863,914

(22) Filed: Apr. 30, 2020

(65) Prior Publication Data

US 2020/0347128 A1    Nov. 5, 2020

Related U.S. Application Data

(60) Provisional application No. 62/842,846, filed on May 3, 2019.

(51) Int. Cl.
| | |
|---|---|
| *A61K 47/64* | (2017.01) |
| *A61K 47/68* | (2017.01) |
| *A61P 17/14* | (2006.01) |
| *C07K 16/24* | (2006.01) |

(52) U.S. Cl.
CPC .......... *C07K 16/246* (2013.01); *A61K 47/643* (2017.08); *A61K 47/6811* (2017.08); *A61P 17/14* (2018.01); *C07K 16/247* (2013.01)

(58) Field of Classification Search
CPC .............................. A61K 47/643; A61K 38/16
See application file for complete search history.

(56) References Cited

U.S. PATENT DOCUMENTS

| | | | |
|---|---|---|---|
| 4,518,584 A | 5/1985 | Mark et al. | |
| 5,700,913 A | 12/1997 | Taniguchi et al. | |
| 5,795,966 A | 8/1998 | Grabstein et al. | |
| 6,013,480 A | 1/2000 | Grabstein et al. | |
| 6,028,186 A | 2/2000 | Tasset et al. | |
| 6,127,387 A | 10/2000 | Huang et al. | |
| 6,168,783 B1 | 1/2001 | Grabstein et al. | |
| 6,261,559 B1 | 7/2001 | Levitt et al. | |
| 6,307,024 B1 | 10/2001 | Novak et al. | |
| 6,323,027 B1 | 11/2001 | Burkly et al. | |
| 6,686,178 B2 | 2/2004 | Novak et al. | |
| 6,770,745 B2 | 8/2004 | Burkly et al. | |
| 6,793,919 B2 | 9/2004 | Mohler | |
| 6,797,263 B2 | 9/2004 | Strom et al. | |
| 6,811,780 B2 | 11/2004 | Furfine et al. | |
| 6,838,433 B2 | 1/2005 | Serlupi-Crescenzi | |
| 6,955,807 B1 | 11/2005 | Shanafelt et al. | |
| 7,105,653 B2 | 9/2006 | Shanafelt et al. | |
| 7,148,333 B2 | 12/2006 | Cox, III | |
| 7,192,578 B2 | 3/2007 | Levitt et al. | |
| 7,235,240 B2 | 6/2007 | Grabstein et al. | |
| 7,314,623 B2 | 1/2008 | Grusby et al. | |
| 7,347,995 B2 | 3/2008 | Strom et al. | |
| 7,423,123 B2 | 9/2008 | Boisvert et al. | |
| 7,473,765 B2 | 1/2009 | Novak et al. | |
| 7,632,814 B2 | 12/2009 | Hazlehurst et al. | |
| 7,645,449 B2 | 1/2010 | Stassi et al. | |
| 7,700,088 B2 | 4/2010 | Levitt et al. | |
| 7,731,946 B2 | 6/2010 | Grusby et al. | |
| 7,785,580 B2 | 8/2010 | Pan et al. | |
| 7,786,072 B2 | 8/2010 | Verdine et al. | |
| 7,910,123 B2 | 3/2011 | McKay | |
| 7,959,908 B2 | 6/2011 | Nelson et al. | |
| 8,110,180 B2 | 2/2012 | Novak et al. | |
| 8,211,420 B2 | 7/2012 | Bondensgaard | |
| 8,455,449 B2 | 6/2013 | Tagaya et al. | |
| 9,133,243 B2 | 9/2015 | Tagaya et al. | |
| 9,133,244 B2 | 9/2015 | Tagaya et al. | |
| 9,675,672 B2 | 6/2017 | Tagaya et al. | |
| 9,951,105 B2 | 4/2018 | Tagaya | |
| 9,959,384 B2 | 5/2018 | Azimi et al. | |
| 10,030,058 B2 | 7/2018 | Azimi | |
| 10,030,059 B2 | 7/2018 | Azimi | |
| 10,227,382 B2 | 3/2019 | Tagya et al. | |
| 10,358,477 B2 | 7/2019 | Jacques et al. | |

(Continued)

FOREIGN PATENT DOCUMENTS

| | | |
|---|---|---|
| CN | 1478098 | 2/2004 |
| CN | 1703423 | 11/2005 |

(Continued)

OTHER PUBLICATIONS

Yampolsky et al., Genetics, 2005, 170:1459-1472.*
Abadie et al., "IL-15: A central regulator of celiac disease immunopathology". Immunol Rev. (2014) 260(1): 221-234.
Antony, et al., "Interleukin-2-Dependent Mechanisms of Tolerance and Immunity In Vivo," J. Immunol. 176: 5255-5266, 2006.
Aringer et al., "Serum interleukin-15 is elevated in systemic lupus erythematosus", Rheumatology (2001) 40(8):876-881.
Asano et al., Molecular scanning of interleukin-21 gene and genetic susceptibility to type 1 diabetes. Hum Immunol. (2007) 68(5):384-391.

(Continued)

*Primary Examiner* — Prema M Mertz
(74) *Attorney, Agent, or Firm* — Knobbe, Martens, Olson & Bear, LLP

(57) ABSTRACT

The γc-family cytokines, Interleukin-2 (IL-2), Interleukin-4 (IL-4), Interleukin-7 (IL-7), Interleukin-9 (IL-9), Interleukin-15 (IL-15), and Interleukin-21 (IL-21), are associated with important human diseases, such as alopecia and alopecia associated disorders. Compositions, methods, and kits to modulate signaling by at least one γc-cytokine family member for inhibiting, ameliorating, reducing a severity of, treating, delaying the onset of, or preventing at least one alopecia related disorder are described.

7 Claims, 32 Drawing Sheets
Specification includes a Sequence Listing.

(56) References Cited

U.S. PATENT DOCUMENTS

| | | |
|---|---|---|
| 10,808,009 B2 | 10/2020 | Tagya et al. |
| 10,854,312 B2 | 12/2020 | Azimi et al. |
| 11,400,134 B2 | 8/2022 | Azimi |
| 11,462,297 B2 | 10/2022 | Azimi et al. |
| 11,708,392 B2 | 7/2023 | Tagaya et al. |
| 11,834,519 B2 | 12/2023 | Tagaya et al. |
| 2002/0114781 A1 | 8/2002 | Strom et al. |
| 2003/0049798 A1 | 3/2003 | Carter et al. |
| 2003/0108549 A1 | 6/2003 | Carter et al. |
| 2004/0009150 A1 | 1/2004 | Nelson et al. |
| 2004/0126900 A1 | 7/2004 | Barry |
| 2004/0136954 A1 | 7/2004 | Grusby et al. |
| 2005/0124044 A1 | 6/2005 | Cunningham et al. |
| 2006/0008848 A1 | 1/2006 | Verdine et al. |
| 2006/0034892 A1 | 2/2006 | Ueno |
| 2006/0039902 A1 | 2/2006 | Young et al. |
| 2006/0236411 A1 | 10/2006 | Dreher et al. |
| 2006/0263857 A1 | 11/2006 | Lefrancois et al. |
| 2007/0048266 A1 | 3/2007 | Nelson |
| 2007/0048831 A1 | 3/2007 | Sprecher et al. |
| 2007/0122413 A1 | 5/2007 | Sivakumar et al. |
| 2008/0038275 A1 | 2/2008 | Martin |
| 2008/0108552 A1 | 5/2008 | Hazlehurst et al. |
| 2008/0166338 A1 | 7/2008 | Leonard |
| 2009/0136511 A1 | 5/2009 | Santos Savio et al. |
| 2009/0148403 A1 | 6/2009 | Bosivert et al. |
| 2009/0253864 A1 | 10/2009 | Peschke et al. |
| 2009/0258357 A1 | 10/2009 | Ruben et al. |
| 2010/0099742 A1 | 4/2010 | Stassi |
| 2010/0135958 A1 | 6/2010 | Hwu |
| 2010/0196309 A1 | 8/2010 | Bondensgaard et al. |
| 2010/0266531 A1 | 10/2010 | Hsieh |
| 2011/0081327 A1 | 4/2011 | Nicolette |
| 2011/0091515 A1 | 4/2011 | Zilberman et al. |
| 2011/0142833 A1 | 6/2011 | Young |
| 2011/0245090 A1 | 10/2011 | Abbas |
| 2011/0311475 A1 | 12/2011 | Borte |
| 2013/0052127 A1 | 2/2013 | Sasaki et al. |
| 2013/0095102 A1 | 4/2013 | Levin |
| 2013/0217858 A1 | 8/2013 | Tagaya et al. |
| 2018/0125941 A1 | 5/2018 | Greve |
| 2018/0237475 A1 | 8/2018 | Tagaya et al. |
| 2018/0258174 A1 | 9/2018 | Mortier et al. |
| 2019/0070263 A1 | 3/2019 | Azimi |
| 2019/0194255 A1 | 6/2019 | Tagaya et al. |
| 2020/0399316 A1 | 12/2020 | Tagaya et al. |
| 2021/0082537 A1 | 3/2021 | Azimi et al. |
| 2021/0324029 A1 | 10/2021 | Doerr et al. |
| 2023/0060637 A1 | 3/2023 | Azimi |
| 2023/0197187 A1 | 6/2023 | Azimi et al. |
| 2023/0338473 A1 | 10/2023 | Tagaya et al. |

FOREIGN PATENT DOCUMENTS

| | | |
|---|---|---|
| EP | 1525213 | 4/2005 |
| JP | 2004-525076 | 8/2004 |
| JP | 2005-508179 | 3/2005 |
| WO | WO 1987/002990 A1 | 5/1987 |
| WO | WO 2000/72864 A1 | 12/2000 |
| WO | WO 2003/040313 A1 | 5/2003 |
| WO | WO 2003/087320 A2 | 10/2003 |
| WO | WO 2003/103589 A2 | 12/2003 |
| WO | WO 2004/084835 A2 | 10/2004 |
| WO | WO 2005/014642 A2 | 2/2005 |
| WO | WO 2005/030196 A2 | 4/2005 |
| WO | WO 2005/067956 A2 | 7/2005 |
| WO | WO 2005/105830 A1 | 11/2005 |
| WO | WO 2005/112983 A2 | 12/2005 |
| WO | WO 2006/105538 A2 | 5/2006 |
| WO | WO 2006/111524 A2 | 10/2006 |
| WO | WO 2006/113331 A1 | 10/2006 |
| WO | WO 2008/049920 A2 | 2/2008 |
| WO | WO 2009/100035 A2 | 8/2009 |
| WO | WO 2009/108341 A1 | 9/2009 |
| WO | WO 2009/132821 A1 | 11/2009 |
| WO | WO 2010/011313 A2 | 1/2010 |
| WO | WO 2010/039533 A2 | 4/2010 |
| WO | WO 2010/054667 A1 | 5/2010 |
| WO | WO 2010/076339 A1 | 7/2010 |
| WO | WO 2010/103038 A1 | 9/2010 |
| WO | WO 2010/133828 A1 | 11/2010 |
| WO | WO 2011/008260 A1 | 1/2011 |
| WO | WO 2011/070214 A2 | 6/2011 |
| WO | WO 2011/133948 A2 | 10/2011 |
| WO | WO 2012/006585 A2 | 1/2012 |
| WO | WO 2012/012531 A2 | 1/2012 |
| WO | WO 2012/099886 A2 | 7/2012 |
| WO | WO 2012/175222 A1 | 12/2012 |
| WO | WO 2015/089217 A2 | 6/2015 |
| WO | WO 2017/062685 A1 | 4/2017 |
| WO | WO 2018/187499 A1 | 10/2018 |

OTHER PUBLICATIONS

Atwa et al., "T-helper 17 cytokines (interleukins 17, 21, 22, and 6, and tumor necrosis factor-α) in patients with alopecia areata: association with clinical type and severity". Int J Dermatol. (2016) 55(6):666-672.

Awwad et al., "Overview of Antibody Drug Delivery". Pharmaceutics (2018) 10(3): 83.

Azimi, N., "Human T Cell Lymphotropic Virus Type I Tax Protein Trans-Activates Interleukin 15 Gene Transcription Through an NF-kappaB Site," Proc. Natl. Acad. Sci. USA 95:2452-2457, 1998.

Azimi, N., "Involvement of IL-15 In The Pathogenesis of Human T Lymphotropic Virus Type-I-Associated Myelopathy/Tropical Spastic Paraparesis: Implications for Therapy with a Monoclonal Antibody Directed to the IL-2/15Rbeta Receptor," J. Immunol. 163:4064-4072, 1999.

Azimi, N., et al., "How Does Interleukin 15 Contribute to the Pathogenesis of HTLV Type-1 Associated Myelopathy/Tropical Spastic Paraparesis?" AIDS Res. Hum. Retroviruses 16:1717-1722, 2000.

Azimi, N., et al., "IL-15 Plays a Major Role in the Persistence of Tax-specific CD8 Cells in HAM/TSP patients," Proc. Natl. Acad. Sci. 98:14559-14564, 2001.

Baranda et al., "IL-15 and IL-15R in leucocytes from patients with systemic lupus erythematosus." Rheumatology (2005) 44(12): 1507-1513.

Bazan, J.F., "Hematopoietic Receptors and Helical cytokines," Immunol. Today 11:350-354, 1990.

Ben Ahmed et al., "IL-15 renders conventional lymphocytes resistant to suppressive functions of regulatory T cells through activation of the phosphatidylinositol 3-kinase pathway". J Immunol. (2009) 182(11):6763-6770.

Benahmed et al., "Inhibition of TGF-beta signaling by IL-15: a new role for IL-15 in the loss of immune homeostasis in celiac disease". Gastroenter. (2007) 132(3):994-1008.

Bernard et al., Identification of an Interleukin-15α Receptor-binding Site on Human Interleukin-15, J Biol Chem., (2004) 279(23):24313-24322.

Bettini et al., "Regulatory T Cells and Inhibitory Cytokines in Autoimmunity," Curr. Opin. Immunol. 21:612-618, 2009.

Blaser et al., "Donor-derived IL-15 is critical for acute allogeneic graft-versus-host disease". Blood (2005) 105(2): 894-901.

Blažek et al., "The production and application of single-chain antibody fragments". Folia Microbiol. (2003) 48(5): 687-698.

Bobbala et al., "Interleukin-15 plays an essential role in the pathogenesis of autoimmune diabetes in the NOD mouse", Diabetologia (2012) 55: 3010-3020.

Bodd et al., "HLA-DQ2-Restricted Gluten-Reactive T cells Produce IL-21 but not IL-17 or IL-22," Mucosal Immunol. 3:594-601, 2010.

Bönsch, et al., Species-specific Agonist/Antagonist Activities of Human Interleukin-4 Variants Suggest Distinct Ligand Binding Properties of Human and Murine Common Receptor γ Chain, The Journal of Biological Chemistry (1995) 270:8452-8457.

Borrego et al., "Recognition of human histocompatibility leukocyte antigen (HLA)-E complexed with HLA class I signal sequence-

(56) References Cited

OTHER PUBLICATIONS derived peptides by CD94/NKG2 confers protection from natural killer cell-mediated lysis". J Exp Med. (1998) 187(5): 813-818.
Botti et al., "Psoriasis, from pathogenesis to therapeutic strategies: IL-21 as a novel potential thereapeutic target". Curr Pharm Biotechnol. (2012) 13(10): 1861-1867.
Broux et al., "IL-15 amplifies the pathogenic properties of CD4+ CD28- T cells in multiple sclerosis". J Immunol. (2015) 194(5): 2099-2109.
Brumbaugh et al., "Clonotypic differences in signaling from CD94 (kp43) on NK cells lead to divergent cellular responses". J Immunol. (1996) 157(7): 2804-2812.
Bubier et al., "A critical role for IL-21 receptor signaling in the pathogenesis of systemic lupus erythematosus in BXSB-Yaa mice." Proc Natl Acad Sci U S A (2009) 106(5):1518-1523.
Bucher et al., "IL-21 blockade reduces graft-versus-host disease mortality by supporting inducible T regulatory cell generation". 2009 114:5375-84.
Cantoni et al., "The activating form of CD94 receptor complex: CD94 covalently associates with the Kp39 protein that represents the product of the NKG2-C gene". Eur J Immunol. (1998) 28: 327-338.
Caruso et al., "Involvement of interleukin-21 in the epidermal hyperplasia of psoriasis". Nature Med. (2009) 15(():1013-1015.
Caruso et al., "Pathogenic role of interleukin-21 in psoriasis." Cell Cycle (2009) 8: 3629-3630.
Chen et al., "Insulin-dependent diabetes induced by pancreatic betacell expression of IL-15 and IL-15R alpha", Proc Natl Acad Sci U S A (2013) 110:13534-13539.
Chen et al., "Induction of autoimmune diabetes in non-obese diabetic mice requires interleukin-21-dependent activation of autoreactive CD8+T cells". Clin Exp Immunol. (2013) 173(2): 184-194.
Chik et al., "Elevated serum interleukin-15 level in acute graft-versus-host disease after hematopoietic cell transplantation." J Pediatr Hematol Oncol. (2003) 25(12): 960-964.
Cox et al., "Immunoassay methods", in Assay Guidance Manual [Internet], S. Markossian, G.S. Sittampalam, N.P. Coussens, H. Nelson, et al. [Eds.] (Bethesda, MD: Eli Lilly & Company and the National Center for Advancing Translational Sciences); 2004 Edition; (TOC only).
D'Auria et al., "Increased serum interleukin-15 levels in bullous skin diseases: correlation with disease intensity". Arch Dermatol Res. (1999) 291: 354-356.
De Nitto et al., "Involvement of interleukin-15 and interleukin-21, two gamma-chain-related cytokines, in deiac disease", World J Gastroenter. (2009) 15:4609-4614.
De Nitto et al. "Interleukin-21 triggers effector cell responses in the gut." World J Gastroenterol. (2010) 16(29):3638-3641.
Depaolo et al., "Co-adjuvant effects of retinoic acid and IL-15 induce inflammatory immunity to dietary antigens". Nature (2011) 471(7337): 220-224.
De Rezende, L.C., et al., "Regulatory T Cells as a Target for Cancer Therapy," Arch. Immunol. Ther. Exp. 58:179-190, 2010.
Definition of composite from www.merriam-sebster.com/dictionary/composite, pp. 1-5. Accessed Feb. 17, 2015.
Definition of derivative from http://cancerweb.ncl.ac.uk/omd/about. html, pp. 1-5. Accessed Jul. 7, 2005.
Di Sabatino A. et al., "Epithelium derived interleukin 15 regulates intraepithelial lymphocyte Th1 cytokine production, cytotoxicity, and survival in coeliac disease", Gut (2006) 55(4):469-477.
Dubois, S., et al., "IL-15R alpha Recycles and Presents IL-15 In Trans to Neighboring Cells," Immunity 17:537-547, 2002.
Fang et al., "Prophylactic effects of interleukin-2 receptor antagonists against graft-versus-host disease following unrelated donor peripheral blood stem cell transplantation". Biol Blood Marrow Transplant. (2012) 18(5): 754-762.
Fehniger, T.A., "Fatal Leukemia in Interleukin 15 Transgenic Mice Follows Early Expansions in Natural Killer and Memory Phenotype CD8+ T Cells," J. Exp. Med. 193:219-231, 2001.

Ferreira et al., "IL-21 production by CD4+ effector T cells and frequency of circulating follicular helper T cells are increased in type 1 diabetes patients", Diabetologia (2015) 58: 781-790.
Fina et al., "Interleukin 21 contributes to the mucosal T helper cell type 1 resonse in coeliac disease". Gut (2008) 57(7):887-892.
Fisher A.G. et al., "Lymphoproliferative disorders in an IL-7 transgenic mouse line," Leukemia( 1993) 2: 66-68.
Frenzel et al., "Designing Human Antibodies by Phage Display". Transfus Med Hemother. (2017) 44(5): 312-318.
Fuentes-Duculan et al., "Biomarkers of alopecia areata disease activity and response to corticosteroid treatment". Exp Dermatol. (2016) 4:282-286.
Garrity et al., "The activating NKG2D receptor assembles in the membrane with two signaling dimers into a hexameric structure". Proc Natl Acad Sci. (2005) 102(21): 7641-7646.
Ghalamfarsa et al., "IL-21 and IL-21 receptor in theimmunopathogenesis of multiple sclerosiS", J Immunotoxicol. (2016) 13(3):274-285.
Gilhar et al., "Alopecia areata animal models illuminate autoimmune pathogenesis and novel immunotherapeutic strategies". Autoimmun Rev. (2016) 15(7): 726-735.
Gong, J.H. et al., Characterization of a human cell line (NK-92) with phenotypical and functional characteristics of activated natural killer cells. Leukemia 8, 1994, pp. 652-658.
Gonzalez-Alvaro et al., "Increased serum levels of interleukin-15 in rheumatoid arthritis with long-term disease." Clin Exp Rheumatol. (2003) 21(5):639-642.
Grando et al., "Mediators of inflammation in blister fluids from patients with pemphigus vulgaris and bullous pemphigoid". 1989 Arch Dermatol. (1989) 125:925-930.
Groh et al., "Stimulation of T cell autoreactivity by anomalous expression of NKG2D and its MIC ligands in rheumatoid arthritis". Proc Natl Acad Sci U S A. (2003) 100(16):9452-9457.
Guo-Qiang et al., "Guided selection methods through chain shuffling". Methods Mol Biol. (2009) 562(10): 133-142.
Habib T. et al., "IL-21: a novel IL-2-family lymphokine that modulates B, T, and natural killer cell responses", J Allergy Clin Immunol. (2003) 112(6):1033-1045.
Hammers et al., "Antibody Phage Display: Technique and Applications". J Invest Dermatol. (2014) 134(2): e17; 13 pages.
Harada et al., "Production of interleukin-7 and interleukin-15 by fibroblast-like synoviocytes from patients with rheumatoid arthritis." Arthritis Rheum. (1999) 42(7):1508-1516.
He et al., "Elevated serum levels of interleukin 21 are associated with disease severity in patients with psoriasis." Br J Dermatol. (2012) 167: 191-193.
Hennighausen L. et al., "Interpretation of Cytokine Signaling Through the Transcription Factors STAT5A and STAT5B," Genes Dev. 22:711-721, 2008.
Hessian P.A. et al., "Cytokine profile of the rheumatoid nodule suggests that it is a Th1 granuloma." Arthritis Rheum. (2003) 48(2):334-338.
Hines L. et al., Interleukin 15, partial [synthetic construct]. NCBI PDS Accession No. AAX36174, interleukin 15, partial [synthetic construct]. Submitted Jan. 5, 2005; downloaded from the internet <https://www.ncbi.nlm.nih.gov/protein/60811495/> on Dec. 14, 2016, p. 1.
Hippen et al., "Blocking IL-21 signaling ameliorates xenogeneic GVHD induced by human lymphocytes". Blood (2012) 119(2): 619-628.
Hodge et al., "IL-2 and IL-12 alter NK cell responsiveness to IFN-gamma-inducible protein 10 by down-regulating CXCR3 expression". J Immunol. (2002) 168(12): 6090-6098.
Hong et al., Regulatory and pro-inflammatory phenotypes of myelin basic protein-autoreactive T cells in multiple sclerosis. Int Immunol. (2009) 21(12): 1329-1340.
Hüe et al., "A direct role for NKG2D/MICA interaction in villous atrophy during celiac disease." Immunity (2004) 21(3): 367-377.
Jabri B. et al., "Selective expansion of intraepithelial lymphocytes expressing the HLA-E-specific natural killer receptor CD94 in celiac disease", Gastroenter. (2000) 118:867-879.
Jagielska et al., "Follow-up study of the first genome-wide association scan in alopecia areata: IL13 and KIAA0350 as suscepti-

(56) References Cited

OTHER PUBLICATIONS bility loci supported with genome-wide significance." J Invest Dermatol. (2012) 132:2192-2197.
Jespers et al., "Guiding the selection of human antibodies from phage display repertoires to a single epitope of an antigen". Biotechnology (1994) 12: 899-903.
Jespersen et al., "BepiPred-2.0: improving sequence-based B-cell epitope prediction using conformational epitopes". Nucleic Acids Res. (2017) 45(W1): W24-W29.
Kang et al., Rational Design of Interleukin-21 Antagonist through Selective Elimination of the C Binding Epitope, J Biol Chem. (2010) 285(16): 12223-12231.
Kivisäkk et al., "IL-15 mRNA expression is up-regulated in blood and cerebrospinal fluid mononuclear cells in multiple sclerosis (MS)", Clin Exp Immunol. (1998) 111(1):193-197.
Klingemann H.G. et al., "A cytotoxic NK-cell line (NK-92) for ex vivo purging of leukemia from blood," Biol. Blood Marrow Transplant (1996) 2(2):68-75.
Kluczyk et al., "The "two-headed" peptide inhibitors of interleukin-1 action," Peptides, (200), 21: 1411-1420.
Köhler et al., "Continuous cultures of fused cells secreting antibody of predefined specificity". Nature (1975) 256(5517): 495-497.
Kooy-Winkelaar et al., "CD4 T-cell cytokines synergize to induce proliferation of malignant and nonmalignant innate intraepithelial lymphocytes", Proc Natl Acad Sci U S A (2017)114(6):E980-989.
Krause C.D. et al., "Evolution of the Class 2 Cytokines and Receptors, and Discovery of New Friends and Relatives," Pharmacol. and Therapeutics 106:299-346, 2005.
Kuczynski et al., "IL-15 is elevated in serum patients with type 1 diabetes mellitus." Diabetes Res Clin Pract. (2005) 69(3):231-236.
Kundig T.M. et al. "Immune Responses of the interleukin-2-deficient mice," Science 262, 1993, pp. 1059-1061.
Laffleur et al., "Production of human or humanized antibodies in mice". In Antibody Methods and Protocols by G. Proetzel et al.,[Ed.]. (2012) 901:149-159 (TOC only).
Lazetic et al., "Human natural killer cell receptors involved in MHC class I recognition are disulfide-linked heterodimers of CD94 and NKG2 subunits". J Immunol. (1996) 157(11): 4741-4745.
Le Buanec, H., et al., "Control of Allergic Reactions in Mice by an Active Anti-Murine IL-4 Immunization," Vaccine 25:7206-7216, 2007.
Littman D.R. et al., "Th17 and Regulatory T Cells in Mediating and Restraining Inflammation," Cell 140(6):845-858, 2010.
Liu et al., "IL-15 is highly expressed in inflammatory bowel disease and regulates local T cell-dependent cytokine production." J Immunol. (2000) 164(7):3608-3615.
Lonberg et al., "Human antibodies from transgenic mice". Int Rev Immunol. (1995) 13: 65-93.
Maiuri L. et al., "Interleukin 15 Mediates Epithelial Changes in Celiac Desease", Gastroenter. (2000) 119:996-1006.
McInnes et al., "Interleukin-15 mediates T cell-dependent regulation of tumor necrosis factor-α production in rheumatoid arthritis." Nature Med. (1997) 3(2): 189-195.
Mention J-J. et al., "Interleukin 15: a key to disrupted intraepithelial lymphocyte homeostasis and lymphomagenesis in celiac disease", Gastroenter. (2003) 125(3):730-745.
Meresse et al., "Coordinated induction by IL15 of a TCR-independent NKG2D signaling pathway converts CTL into lymphokine-activated killer cells in celiac disease." Immunity (2004) 21(3):357-366.
Meresse et al., "The cytokine interleukin 21: a new player in coeliac disease?." Gut (2008) 57(7): 879-881.
Mingari et al., "HLA class I-specific inhibitory receptors in human T lymphocytes: interleukin 15-induced expression of CD94/NK62A in superantigen- or alloantigen-activated CD8+ T cells". Proc Natl Acad Sci. (1998) 95(3): 1172-1177.
Miyagawa, F., et al., "IL-15 Serves as a Costimulator in Determining the Activity of Autoreactive CD8 T Cells in an Experimental Mouse Model of Graft-Versus-Host-Like Disease," J. Immunol. 181:1109-1119, 2008.

Monteleone et al., "Interleukin-21 enhances T-helper cell type I signaling and interferon-γ production in Crohn's disease", Gastroenterology (2005) 128(3): 687-694.
Monteleone et al., "Characterization of IL-17A—Producing cells in celiac disease mucosa", J Immunol. (2010) 184: 2211-2218.
Nakou et al., "Interleukin-21 is increased in active systemic lupus erythematosus patients and contributes to the generation of plasma B cells." Clin Exp Rheumatol. (2013) 31(2):172-179.
NCBI Accession No. ABF82250, Accessed Aug. 11, 2014.
NCBI Accession No. BAA96385, Accessed Aug. 11, 2014.
NCBI Accession No. NP_999580, Accessed Aug. 11, 2014.
NCBI Accession No. ACT78884, Accessed Aug. 11, 2014.
NCBI Accession No. NP_999288, Accessed Aug. 11, 2014.
Noguchi, M., et al., "Interleukin 2 Receptor Gamma Chain Mutation Results in X-linked Severe Combined Immunodeficiency in Humans," Cell 73:147-157, 1993.
Nohra et al., RGMA and IL21R show association with experimental inflammation and multiple sclerosis. Genes & Immunity, (2010) 11(4): 279-293.
Nowak E.C. et al., "IL-9 as a mediator of Th17-driven inflammatory disease", J Exp Med. (2009) 206:1653-1660.
Oh et al., "Treatment of HTLV-I-Associated Myelopathy / Tropical Spastic Paraparesis: Towards Rational Targeted Therapy," Neurol. Clin. 26:781-785, 2008.
Olosz, F. et al. Structural Basis for Binding Multiple Ligands by the Common Cytokine Receptor [gamma] -chain, Journal of Biological Chemistry, vol. 277, No. 14, pp. 12047-12052, (2002).
Oppenheimer-Marks et al., "Interleukin 15 is produced by endothelial cells and increases the transendothelial migration of T cells In vitro and in the SCID mouse-human rheumatoid arthritis model In vivo." J Clin Invest (1998) 101(6):1261-1272.
Orzaez, M., et al., "Peptides and Peptide Mimics as Modulators of Apoptotic Pathways," Chem. Med. Chem. 4:146-160, 2009.
O'Shea, J.J., "Targeting the Jak/STAT Pathway for Immunosuppression," Ann. Rheum. Dis. 63:(Suppl. II):ii67-71, 2004.
Padlan E.A., "A possible procedure for reducing the immunogenicity of antibody variable domains while preserving their ligand-binding properties". Mol Immunol. (1991) 28(4-5): 489-498.
Pashenkov et al., "Levels of interleukin-15-expressing blood mononuclear cells are elevated in multiple sclerosis", Scand J Immunol. (1999) 50(3):302-308.
Paul, W.E., "Pleiotropy and Redundancy: T Cell-Derived Lymphokines in the Immune Response," Cell 57:521-524, 1989.
Pesu, M., "Jak3, Severe Combined Immunodeficiency, and a New Class of Immunosuppressive Drugs," Immunol. Rev. 203:127-142, 2005.
Pesu, M., Laurence, et al., "Therapeutic Targeting of Janus Kinases," Immunol. Rev. 223:132-142, 2008.
Petukhova et al., "Genome-wide association study in alopecia areata implicates both innate and adaptive immunity." Nature (2010) 466(7302):113-117.
Recher et al., "IL-21 is the primary common γ chain-binding cytokine required for human B-cell differentiation in vivo". Blood (2011) 118(26): 6824-6835.
Richmond et al., "Antibody blockade of IL-15 signaling has the potential to durably reverse vitiligo". Sci Transl Med. (2018) 10(450).
Riechmann et al., "Reshaping human antibodies for therapy". Nature (1988) 332: 323-327.
Rochman Y., et al., "New Insights into the Regulation of T Cells by Gamma C Family Cytokines," Nat. Rev. Immunol. 9:480-490, 2009.
Roguska et al., "Humanization of murine monoclonal antibodies through variable domain resurfacing". Proc Natl Acad Sci. (1994) 91(3): 969-973.
Rückert R. et al., "Interleukin-15 stimulates macrophages to activate CD4+ T cells: a role in the pathogenesis of rheumatoid arthritis?", Immunology (2009) 126(1):63-73.
Saha et al., "Prediction of continuous B-cell epitopes in an antigen using recurrent neural network". Proteins (2006) 65: 40-48.
Saikali et al., "Contribution of astrocyte-derived IL-15 to CD8 T cell effector functions in multiple sclerosis", J Immunol. (2010) 185(10):5693-5703.

(56) References Cited

OTHER PUBLICATIONS

Sakaguchi S., et al., "Regulatory T Cells and Immune Tolerance," Cell 133:775-787, 2008.
Sarra M. et al., "IL-15 positively regulates IL-21 production in celiac disease mucosa", Mucosal Immunol. (2013) 6(2):244-255.
Sato N. et al., "Development of an IL-15-Autocrine CD8 T-cell Leukemia in IL-15 Transgenic mice requires the cis-expression of IL-15R apha," Blood (2011) 117(15):4032-4040.
Sawalha et al., "Genetic association of interleukin-21 polymorphisms with systemic lupus erythematosus", Ann Rheum Dis. (2008) 67(4):458-461.
Schaller et al., "Interleukin-2 receptor expression and interleukin-2 production in bullous pemphigoid". Arch Dermatol Res. (1990) 282(4): 223-226.
Schneider et al., "B cell-derived IL-15 enhances CD8 T cell cytotoxicity and is increased in multiple sclerosis patients", J Immunol. (2011) 187(8):4119-4128.
Schumacher et al., "Severe combined immunodeficiencies of the common g-chain/JAK3 signaling pathway." Isr. Med. Assoc. J. (2002) 4: 131-135.
Seffernick J. et al., "Melamine Deaminase and Atrazine Chlorohydrolase: 98 Percent Identical but Functionally Different", J Bacter. (2001) 183(8):2405-2410.
Shultz et al., "Humanized mice for immune system investigation: progress, promise and challenges". Nat Rev Immunol. (2012) 12(11): 786-798.
Sonntag et al., "Chronic graft-versus-host-disease in CD34(+)-humanized NSG mice is associated with human susceptibility HLA haplotypes for autoimmune diseases". J Autoimmun. (2015) 62: 55-66.
Studnicka et al., "Human-engineered monoclonal antibodies retain full specific binding activity by preserving non-CDR complementarity-modulating residues". P rotein Eng (1994) 7: 805-814.
Suarez-Farinas et al., "Alopecia areata profiling shows TH1, TH2, and IL-23 cytokine activation without parallel TH17/TH22 skewing." J Allergy Clin Immunol. (2015) 136(5): 1277-1287.
Sugamura K., et al., "The Common Gamma-Chain for Multiple Cytokine Receptors," Adv. Immunol. 59:225-277, 1995.
Sugamura K., et al., "The Interleukin-2 Receptor Gamma Chain: Its Role in the Multiple Cytokine Receptor Complexes and T Cell Development in XSCID," Annu. Rev. Immunol. 14:179-205, 1996.
Sushama et al., "Cytokine profile (IL-2, IL-6, IL-17, IL-22, and TNF-alpha) in vitiligo—New insight into pathogenesis of disease". J Cosmet Dermatol. (2019) 18(1): 337-341.
Tagaya Y., "Memory CD8 T Cells Now Join 'Club 21," J Leukoc Biol. (2010) 87: 13-15.
Tagaya, Y., et al., "Identification of a Novel Receptor/Signal Transduction Pathway for IL-15/T in Mast Cells," EMBO J. 15:4928-4939, 1996.
Takai K. et al., The Wheat-Germ Cell-Free Expression System, Curr. Pharm. Biotechnol. 11, 2010, pp. 272-278.
Takeshita, T., et al., "Cloning of the Gamma Chain of the Human IL-2 Receptor," Science 257:379-382, 1992.
Tanaka, T., et al., "A Novel Monoclonal Antibody Against Murine IL-2 Receptor Beta-Chain. Characterization of Receptor Expression in Normal Lymphoid Cells and EL-4 Cells," J. Immunol. 147:2222-2228, 1991.
Tang et al., "Cytosolic PLA2 is required for CTL-mediated immunopathology of celiac disease via NKG2D and IL-15." J Exp Med. (2009) 206(3): 707-719.
Terrier et al., "Interleukin 21 Correlates with T Cell and B Cell Subset Alterations in Systemic Lupus Erythematosus", J Rheumatol. (2012) 39(9):1819-1828.
Tomimatsu et al., "Antigen-specific in vitro immunization: a source for human monoclonal antibodies". Methods Mol Biol. (2014) 1060 (Chapter 15): 297-307.
Tzartos et al., "IL-21 and IL-21 Receptor Expression in Lymphocytes and Neurons in Multiple Sclerosis Brain", Am J Pathol. (2011) 178(2):794-802.

Vainer et al., "Colonic expression and synthesis of interleukin 13 and interleukin 15 in inflammatory bowel disease", Cytokine (2000) 12(10):1531-1536.
Vaknin-Dembinsky et al., "Membrane bound IL-15 is increased on CD14 monocytes in early stages of MS", J Neuroimmunol. (2008) 195(1-2):135-139.
Van Heel et al., "A genome-wide association study for celiac disease identifies risk variants in the region harboring IL2 and IL21." Nat Genet. (2007) 39(7): 827-829.
Vaughan et al., "Human Antibodies with Sub-nanomolar Affinities Isolated from a Large Non-immunized Phage Display Library". Nature (1996) 14(3): 309-314.
Villadsen et al., "Resolution of psoriasis upon blockade of IL-15 biological activity in a xenograft mouse model". J Clin Invest. (2003) 112: 1571-1580.
Waldmann, T.A., Anti-Tac (daclizumab, Zenapax) in the Treatment of Leukemia, Autoimmune Diseases, and in the Prevention of Allograft Rejection: A 25-Year Personal Odyssey, J. Clin. Immunol. 27:1-18, 2007.
Waldmann, T.A., "The biology of IL-15: implications for cancer therapy and the treatment of autoimmune disorders." J Investig Dermatol Symp Proc. (2013) 16(1):S28-S30.
Walensky L.D. et al., "Hydrocarbon-Stapled Peptides: Principles, Practice, and Progress", Miniperspective; J Med Chem. (Aug. 2014) 57(15):6275-6288.
Water is naturally occurring from www.biology-online.org/dictionary/Water, pp. 1-3, Accesssed Apr. 24, 2014.
Williams et al., "Humanising Antibodies by CDR Grafting.", in: Antibody Engineering, eds R. Kontermann and S. Dübel (Springer-Berlin, Heidelberg); (2010) Chapter 21: 319-339.
Witkowski A. et al., "Conversion of a beta-Ketoacyl Synthase to a Malonyl Decarboxylase by Replacement of the Active-Site Cysteine with Glutamine", Biochem. (1999) 38:11643-11650.
Xing et al., "Alopecia areata is driven by cytotoxic T lymphocytes and is reversed by JAK inhibition." Nat Med. (2014) 9:1043-1049.
Xing et al., "Interleukin-21 induces migration and invasion of fibroblast-like synoviocytes from patients with rheumatoid arthritis", Clin Exp Immunol. (May 2016) 184(2):147-158.
Xing et al., "Interleukin-21 Induces Proliferation and Proinflammatory Cytokine Profile of lFibroblast-like Synoviocytes of Patients with Rheumatoid Arthritis", Scand J Immunol. (Jan. 2016) 83(1):64-71.
Yampolsky, L. et al., The Exchangeability of Amino Acids in Proteins, Genetics, 170, pp. 1459-1472, (2005).
Yano et al., "Interleukin 15 induces the signals of epidermal proliferation through ERK and PI 3-kinase in a human epidermal keratinocyte cell line, HaCaT." Biochem Biophys Res Comm. (2003) 301(4): 841-847.
Yao et al., "SVMTriP: A Method to Predict Antigenic Epitopes Using Support Vector Machine to Integrate Tri-Peptide Similarity and Propensity". PLoS One (2012) 7(9): e45152.
Zanzi et al., "IL-15 interferes with suppressive activity of intestinal regulatory T cells expanded in Celiac disease." Am J Gastroenter (2011) 106(7): 1308-1317.
Zeng et al., "Synergy of IL-21 and IL-15 in regulating CD8+ T cell expansion and function." J Exp Med. (2005) 201(1): 139-148.
Office Action dated Oct. 22, 2015 for AU Application 2012207456.
Notice of Acceptance dated Oct. 19, 2016 for Australian Application 2012207456.
Office Action dated Feb. 9, 2018 in Australian Application No. 2017200489.
Notice of Acceptance dated Jan. 14, 2019 in Australian Application No. 2017200489.
Office Action dated Jun. 6, 2020 in Australian Application No. 2019202527.
Office Action regarding National Genetic Patrimony/Traditional Knowledge, dated Feb. 11, 2020, in Brazilian Application No. 1120130180463.
Office Action dated Nov. 22, 2017 in Canadian Application No. 2,824,51.
Office Action dated Nov. 23, 2018 in Canadian Application No. 2,824,515.

(56) References Cited

OTHER PUBLICATIONS

Office Action dated Dec. 19, 2019 for Canadian Patent Application No. 2824515.
Office Action dated Jul. 2, 2014 for corresponding CN Application 201280010348.8.
Office Action dated Apr. 28, 2015 for Chinese Patent Application No. 201280010348.8.
Office Action dated Oct. 27, 2015 for Chinese Patent Application No. 201280010348.8.
Office Action dated Jul. 4, 2016 for Chinese Patent Application No. 201280010348.8.
Notification of Re-examination dated Mar. 24, 2017 for Chinese Patent Application 201280010348.8.
Decision of Re-examination dated Jun. 27, 2017 in Chinese Application 201280010348.8.
Notification of Allowance dated May 31, 2018 for Chinese Patent Application 201280010348.8.
Extended EP Search report dated May 22, 2014 for European Patent Application No. 12736203.6.
Office Action dated Oct. 26, 2016 in EP Patent Application No. 12736203.6.
Office Action dated Oct. 4, 2017 in European Patent Application No. 12736203.6.
Office Action dated Nov. 26, 2018 in European Patent Application No. 12736203.6.
Notice of Allowance dated Jul. 5, 2019 for European Patent Application No. 12736203.6.
Extended European Search Report dated Feb. 10, 2020 in European Application No. 19206731.2.
Office Action dated Jan. 26, 2016 for JP Patent Application 2013-550541.
Office Action dated Nov. 29, 2016 for JP Patent Application 2013-550541.
Office Action dated Feb. 27, 2018 for JP Patent Application 2013-550541.
Office Action dated May 8, 2018 in JP Patent Application No. 2017-90501.
Office Action dated Apr. 23, 2019 in Japanese Patent Application No. 2017-90501.
Office Action dated Jun. 23, 2020 in Japanese Application No. 2017-090501.
Office Action dated Sep. 29, 2020 in Japanese Application No. 2019-152602.
International Search Report and Written Opinion dated May 10, 2012 for PCT/US2012/021566.
International Preliminary Report on Patentability dated Jul. 23, 2013 for PCT/US2012/021566.
International Search Report and Written Opinion dated Jun. 26, 2015 for PCT/US14/69597.
International Preliminary Report on Patentability dated Jun. 14, 2016 for PCT/US2012/062870.
Examination Report dated Nov. 14, 2018 in Australian Patent Application No. 2016334085.
Office Action dated Oct. 28, 2019 for AU Patent Application No. 2016334085.
Office Action dated May 27, 2020 in Australian Application No. 2020201174.
Office Action dated Jan. 31, 2019 in Canadian Patent Application No. 3,000,207.
Office Action dated Feb. 4, 2020 in In Canadian Application No. 3000207.
Extended European Search Report dated Mar. 28, 2019 in European Patent Application No. 16854367.6.
Office Action dated Mar. 27, 2020 for European Application No. 16854367.6.
Office Action dated Jun. 4, 2019 in JP Patent Application No. 2018-517887.
Office Action dated May 19, 2020 in Japanese Patent Application No. 2018-517887.
Office Action dated Nov. 10, 2020 in Japanese Patent Application No. 2018-517887.
Office Action dated Sep. 25, 2019 for KR Patent Application No. 10-2018-7013183.
International Search Report and Written Opinion dated Jan. 17, 2017 for PCT/US2016/055845.
International Preliminary Report on Patentability dated Apr. 10, 2018 for PCT/US2016/055845.
Extended European Search Report dated Oct. 15, 2020 for Application No. 18780544.5.
International Search Report and Written Opinion dated Aug. 23, 2018 for PCT/US2018/026125.
Notice of Allowance dated Feb. 19, 2013 for U.S. Appl. No. 13/589,017.
Restriction Requirement dated May 9, 2014 for U.S. Appl. No. 13/868,725.
Office Action dated Aug. 18, 2014 for U.S. Appl. No. 13/868,725.
Office Action dated Oct. 18, 2014 for U.S. Appl. No. 13/868,725.
Office Action dated Feb. 24, 2015 for U.S. Appl. No. 13/868,725.
Notice of Allowance dated May 11, 2015 for U.S. Appl. No. 13/868,725.
Restriction Requirement dated Apr. 25, 2016 for U.S. Appl. No. 14/852,240.
Office Action dated Sep. 6, 2016 for U.S. Appl. No. 14/852,240.
Notice of Allowance dated Feb. 6, 2017 for U.S. Appl. No. 14/852,240.
Restriction Requirement dated Jan. 26, 2018 for U.S. Appl. No. 15/474,312.
Office Action dated Jun. 22, 2018 for U.S. Appl. No. 15/474,312.
Notice of Allowance dated Oct. 22, 2018 for U.S. Appl. No. 15/474,312.
Restriction Requirement dated Jun. 24, 2014 for U.S. Appl. No. 13/980,305.
Office Action dated Nov. 12, 2014 for U.S. Appl. No. 13/980,305.
Notice of Allowance dated May 4, 2015 for U.S. Appl. No. 13/980,305.
Restriction Requirement dated Feb. 28, 2017 for U.S. Appl. No. 15/179,900.
Office Action dated Jul. 24, 2017 in U.S. Appl. No. 15/179,900.
Notice of Allowance dated Dec. 15, 2017 in U.S. Appl. No. 15/179,900.
Restriction Requirement dated Mar. 22, 2019 for U.S. Appl. No. 15/957,806.
Office Action dated Aug. 16, 2019 for U.S. Appl. No. 15/957,806.
Notice of Allowance dated Feb. 26, 2020 in U.S. Appl. No. 15/957,806.
Notice of Allowance dated Jun. 5, 2020 in U.S. Appl. No. 15/957,806.
Restriction Requirement dated Mar. 24, 2017 for U.S. Appl. No. 15/103,804.
Office Action dated Aug. 3, 2017 for U.S. Appl. No. 15/103,804.
Notice of Allowance dated Dec. 19, 2017 for U.S. Appl. No. 15/103,804.
Restriction Requirement dated Apr. 8, 2019 for U.S. Appl. No. 15/964,717.
Office Action dated Sep. 9, 2019 for U.S. Appl. No. 15/964,717.
Office Action dated Feb. 26, 2020 for U.S. Appl. No. 15/964,717.
Notice of Allowance dated Jul. 29, 2020 for U.S. Appl. No. 15/964,717.
Restriction Requirement dated Jul. 25, 2017 in U.S. Appl. No. 15/287,517.
Office Action dated Oct. 23, 2017 in U.S. Appl. No. 15/287,517.
Notice of Allowance dated Mar. 26, 2018 in U.S. Appl. No. 15/287,517.
Office Action dated Aug. 8, 2017 for U.S. Appl. No. 15/585,666.
Office Action dated Dec. 13, 2017 for U.S. Appl. No. 15/585,666.
Notice of Allowance dated Mar. 26, 2018 in U.S. Appl. No. 15/585,666.
Restriction Requirement dated Apr. 30, 2020 in U.S. Appl. No. 15/767,133.
Office Action dated Sep. 4, 2020 in U.S. Appl. No. 15/767,133.
Abboud et al., Severe cytokine release syndrome after T cell-replete peripheral blood Haploidentical donor transplantation is associated

(56) References Cited

OTHER PUBLICATIONS with poor survival and anti-IL-6 therapy is safe and well tolerated. Biol Blood Marrow Transpl. Oct. 1, 2016;22(10):1851-1860.
Abdel-Hakeem M.S., Viruses teaching Immunology: Role of LCMV model and human viral infections in immunological discoveries. Viruses. Jan. 27, 2019;11(2):106 in 19 pages.
Abe R., Immunological Response in Stevens-Johnson Syndrome and Toxic Epidermal Necrolysis. J Dermatol. Jan. 2015;42(1):42-48.
Adusumilli et al., Regional delivery of mesothelin-targeted CAR T cell therapy generates potent and long-lasting CD4-dependent tumor immunity. Science Transl. Med. Nov. 5, 2014;6(261):261ra151 in 31 pages.
Agostini et al., Role of IL-15, IL-2, and their receptors in the development of T cell Alveolitis in pulmonary sarcoidosis. J Immunol. Jul. 15, 1996;157(2):910-918.
Agostini et al., New Pathogenetic Insights into the Sarcoid Granuloma. Curr Opin Rheumatol. Jan. 1, 2000;12(1):71-76.
Agouridakis et al., Association between Increased Levels of IL-2 and IL-15 and Outcome in Patients with Early Acute Respiratory Distress Syndrome. Eur J Clin Invest. Nov. 2002;32(11):862-867.
Allison et al., Association of interleukin-15-induced peripheral immune activation in persons coinfected with hepatitis C virus and HIV. J Infect Dis.Aug. 1, 2009;200(4):619-623.
Anonymous: "Equillium®—EQ101: A multi-specific cytokine inhibitor to treat alopecia areata". Presentation 6th Annual Dermatology Drug Development Summit; Equillium, Inc.; Nov. 1-3, 2022; 23 pages.
Antin et al., Cytokine dysregulation and acute graft-versus-host disease. Blood. Dec. 15, 1992;80(12):2964-2968.
Arras et al., Interleukin-9 reduces lung Fibrosis and type 2 immune polarization induced by silica particles in a murine model. Am J Resp Cell Mol Biol. Apr. 1, 2001;24(4):368-375.
Assier et al., NK Cells and Polymorphonuclear Neutrophils Are Both Critical for IL-2-Induced Pulmonary Vascular Leak Syndrome. J Immunol. Jun. 15, 2004;172(12):7661-7668.
Bae et al., Immune Response during Adverse Events after 17D-Derived Yellow Fever Vaccination in Europe. J Infect Dis. Jun. 1, 2008;197(11):1577-1584.
Baird et al., Multiplex immunoassay analysis of cytokines in idiopathic inflammatory myopathy. Arch Pathol Lab Med. Feb. 2008;132(2):232-238.
Baize et al., Early and Strong Immune Responses Are Associated with Control of Viral Replication and Recovery in Lassa Virus-Infected Cynomolgus Monkeys. J Virol. 2009; 83:5890-903.
Banadyga et al., The Cytokine Response Profile of Ebola Virus Disease in a Large Cohort of Rhesus Macaques Treated with Monoclonal Antibodies. Open Forum Infect Dis. 2019; 6:ofz046 in 6 pages.
Baraut et al., Relationship between cytokine profiles and clinical outcomes in patients with systemic sclerosis. Autoimmun Rev. 2010; 10:65-73.
Barnes et al., The Cytokine Network in Asthma and Chronic Obstructive Pulmonary Disease. J Clin Invest. 2008; 118:3546-3556.
Becker et al., Interleukin 15 Is Required for Proliferative Renewal of Virus-Specific Memory CD8 T Cells. J Exp Med. 2002; 195:1541-1548.
Belani et al., T Cell Activation and Cytokine Production in Anti-CD3 Bispecific Antibody Therapy. J Hematother. 1995; 4:395-402.
Belhadjer et al., Acute heart failure in multisystem inflammatory syndrome in children (MIS-C) in the context of global SARS-CoV-2 pandemic. Circulation in press Aug. 4, 2020;142:429-436.
Bequignon et al., Pathogenesis of chronic rhinosinusitis with nasal polyps: Role of IL-6 in airway epithelial cell dysfunction. J Transl Med. 2020 ;18:136 in 12 pages.
Biber et al., Administration of two macrophage-derived interferon γ-inducing factors (IL-12 and IL-15)induces a lethal systemic inflammatory response in mice that is dependent on natural killer cells but does not require interferon- γ. Cell Immunol. Mar. 1, 2002;216(1-2):31-42.
Bixler et al., The Role of Cytokines and Chemokines in Filovirus Infection. Viruses 2015; 7:5489-5507.
Björkström et al., Rapid Expansion and Long-Term Persistence of Elevated NK Cell Numbers in Humans Infected with Hantavirus. J Exp Med. 2010; 208:13-21.
Blackwell et al., Sepsis and Cytokines: Current Status. Br J Anaesth. 1996; 77:110-7.
Blaser et al., Trans-Presentation of Donor-Derived Interleukin 15 Is Necessary for the Rapid Onset of Acute Graft-versus-Host Disease but Not for Graft-versus-Tumor Activity. Blood. 2006; 108:2463-2469.
Bonifant et al., Toxicity and Management in CAR T-Cell Therapy. Mol Ther Oncolytics. 2016; 3:16011 in 7 pages.
Boumba et al., Cytokine mRNA expression in the labial salivary gland tissues from patients with primary Sjögrens Syndrome. Br J Rheumatol. 1995; 34:326-333.
Braun et al., NK Cell Activation in Human Hantavirus Infection Explained by Virus-Induced IL-15/IL 15Ra Expression. PLoS Pathog. 2014; 10:e1004521 in 12 pages.
Brisse et al., Hemophagocytic Lymphohistiocytosis (HLH): A Heterogeneous Spectrum of Cytokine-Driven Immune Disorders. Cytokine Growth Factor Rev. 2015; 26:263-280.
Brudno et al. Toxicities of Chimeric Antigen Receptor T Cells: Recognition and Management. Blood. 2016; 127:3321-3330.
Bruminhent et al., Acute Interstitial Pneumonia (Hamman-Rich Syndrome) as a Cause of Idiopathic Acute Respiratory Distress Syndrome. Case Rep Med. 2011; 2011:628743 in 5 pages.
Buchweitz et al., Time-Dependent Airway Epithelial and Inflammatory Cell Responses Induced by Influenza Virus A/PR/8/34 in C57BL/6 Mice. Toxicol Pathol. 2007; 35:424-435.
Cahill et al. Circulating Factors in Trauma Plasma Activate Specific Human Immune Cell Subsets. Injury 2020; 51:819-829.
Caproni et al., Expression of Cytokines and Chemokine Receptors in the Cutaneous Lesions of Erythema Multiforme and Stevens-Johnson Syndrome/Toxic Epidermal Necrolysis. Br J Dermatol. 2006; 155:722-728.
Carding et al., Activation of Cytokine Genes in T Cells during Primary and Secondary Murine Influenza Pneumonia. J Exp Med. 1993; 177:475-482.
Carey et al., Neutrophil Activation, Vascular Leak Toxicity, and Cytolysis during Interleukin-2 Infusion in Human Cancer. Surgery. 1997; 122:918-926.
Cerar et al., Diagnostic value of cytokines and chemokines in Lyme neuroborreliosis. Clin Vaccine Immunol. 2013; 20:1578-1584.
Channappanavar et al., Pathogenic Human Coronavirus Infections: Causes and Consequences of Cytokine Storm and Immunopathology. Semin Immunopathol. Jul. 2017;39(5):529-539.
Chaturvedi et al., Cytokine Cascade in Dengue Hemorrhagic Fever: Implications for Pathogenesis. FEMS Immunol Med Microbiol. Jul. 1, 2000;28(3):183-188.
Chen et al., Cellular Immune Responses to Severe Acute Respiratory Syndrome Coronavirus (SARS-CoV) Infection in Senescent BALB/c Mice: CD4+ T Cells Are Important in Control of SARS-CoV Infection. J Virol. Feb. 1, 2010;84(3):1289-1301.
Chen et al., Elevated Cytokine Levels in Tears and Saliva of Patients with Primary Sjögren's Syndrome Correlate with Clinical Ocular and Oral Manifestations. Sci Rep. May 13, 2019;9(1):7319 in 10 pages.
Chi et al., Cytokine and Chemokine Levels in Patients Infected with the Novel Avian Influenza A (H7N9) Virus in China. J Infect Dis. Dec. 15, 2013;208(12):1962-1967.
Chien et al., Temporal Changes in Cytokine/Chemokine Profiles and Pulmonary Involvement in Severe Acute Respiratory Syndrome. Respirology. Nov. 2006;11(6):715-722.
Chiotos et al., Multisystem Inflammatory Syndrome in Children during the COVID-19 pandemic: A Case Series. J Pediatr Infect Dis Soc. Jul. 2020;9(3):393-398.
Chung et al., Recent Advances in the Genetics and Immunology of Stevens-Johnson Syndrome and Toxic Epidermal Necrosis. J Dermatol Sci. Jun. 1, 2012;66(3):190-196.

(56) References Cited

OTHER PUBLICATIONS

Cicardi et al., The Systemic Capillary Leak Syndrome: Appearance of Interleukin-2-Receptor-Positive Cells during Attacks. Ann Intern Med. Sep. 15, 1990;113(6):475-477.

Ciccia et al., Difference in the expression of IL-9 and IL-17 correlates with different histological pattern of vascular wall injury in giant cell arteritis. Rheumatology. Sep. 1, 2015;54:1596-1604.

Clay et al., Severe acute respiratory syndrome-Coronavirus Infection in Aged Nonhuman Primates is Associated with Modulated Pulmonary and Systemic Immune Responses. Immun Ageing. Dec. 2014;11(1):1-6.

Cron et al., Cytokine Storm Syndrome. 2019 Cham: Springer International Publishing; TOC (17 pages).

D'Elia et al., Targeting the "cytokine storm" for therapeutic benefit. Clin Vaccine Immunol. Mar. 2013;20(3):319-327.

De Maria et al., CD3+4-8-WT31-(T Cell Receptor γ+) Cells and Other Unusual Phenotypes Are Frequently Detected among Spontaneously Interleukin 2-Responsive T Lymphocytes Present in the Joint Fluid in Juvenile Rheumatoid Arthritis. A Clonal Analysis. Eur J Immunol. 1987; 17:1815-1819.

De Paepe et al., Scanning for Therapeutic Targets within the Cytokine Network of Idiopathic Inflammatory Myopathies. Int J Mol Sci. Aug. 11, 2015;16(8):18683-18713.

Dolinger et al., Pediatric Crohn's Disease and Multisystem Inflammatory Syndrome in Children (MIS-C) and COVID-19 Treated with Infliximab. J Pediatr Gastroenterol Nutr. May 5, 2020;71(2):153-155.

Dong et al., IL-9 Induces Chemokine Expression in Lung Epithelial Cells and Baseline Airway Eosinophilia in Transgenic Mice. Eur J Immunol. Jul. 1999;29(7):2130-2139.

Duan et al. Regulatory mechanisms, prophylaxis and treatment of vascular leakage following severe trauma and shock. Milit. Med Res. Dec. 2017;4(1):11 in 11 pages.

Endo et al., Two types of septic shock classified by the plasma levels of cytokines and endotoxin. 1992 Circ Shock. Dec. 1, 1992;38(4):264-274.

Engelmann et al., Pathophysiologic and Transcriptomic Analyses of Viscerotropic Yellow Fever in a Rhesus Macaque Model. PLoS Negl Trop Dis. 2014 8:e000329 in 16 pages.

Ermler et al., RNA Helicase Signaling Is Critical for Type I Interferon Production and Protection against Rift Valley Fever Virus during Mucosal Challenge. J Virol. May 1, 2013;87(9):4846-4860.

Fadeel et al., Induction of Apoptosis and Caspase Activation in Cells Obtained from Familial Haemophagocytic Lymphohistiocytosis Patients. Br J Haematol. Aug. 1999;106(2):406-415.

Falasca et al., Molecular Mechanisms of Ebola Virus Pathogenesis: Focus on Cell Death. Cell Death Differ. Aug. 2015;22(8):1250-1259.

Faulkner et al., The Mechanism of Superantigen-Mediated Toxic Shock: Not a Simple Th1 Cytokine Storm. J Immunol. Nov. 15, 2005;175(10):6870-6877.

Forrester et al., TCR Expression of Activated T Cell Clones in the Lungs of Patients with Pulmonary Sarcoidosis. J Immunol. Nov. 1, 1994;153(9):4291-4302.

Fox et al., Cytokine MRNA Expression in Salivary Gland Biopsies of Sjögren's Syndrome. J Immunol. Jun. 1, 1994;152(11):5532-553.

Friberg et al., Protective versus Pathologic Pre-Exposure Cytokine Profiles in Dengue Virus Infection. PLoS Negl Trop Dis. Dec. 17, 2018;12(12):e0006975 in 15 pages.

Frohna et al., "B-102: Results from a First-in-human Study with BNZ-1, a novel, selective inhibitor of IL-2, IL-9, and IL-15 at the common gamma-chain receptor, in clinical development for the treatment of HAM/TSP and T-cell malignancies". 19th Int'l Meeting of the Institute of Human Virology—Jan. 1, 2018; Abstract; 1 page.

Frohna et al., "LB1517 Clinical effects of BNZ-1, a selective inhibitor of IL-2/IL-9/IL15 in development for alopecia areata". J Invest Dermatol. Sep. 2018; Abstract p. B9-B10.

Funke et al., Capillary Leak Syndrome Associated with Elevated IL-2 Serum Levels after Allogeneic Bone Marrow Transplantation. Ann Hematol. Jan. 1994;68(1):49-52.

Gogishvili et al., Rapid regulatory T-cell response prevents cytokine storm in CD28 superagonist treated mice. PLoS One. Feb. 27, 2009;4(2):e4643 in 9 pages.

Gono et al., Cytokine profiles in polymyositis and dermatomyositis complicated by rapidly progressive or chronic interstitial lung disease. Rheumatology. Dec. 1, 2014;53(12):2196-2203.

Gourh et al., Polymorphisms in TBX21 and STAT4 increase the risk of systemic sclerosis: Evidence of possible gene-gene interaction and alterations in Th1/Th2 cytokines. Arthritis Rheum. Dec. 2009;60(12):3794-3806.

Guo et al., Coronavirus Disease 2019 (COVID-19) and Cardiovascular Disease: A Viewpoint on the Potential Influence of Angiotensin-Converting Enzyme Inhibitors/Angiotensin Receptor Blockers on Onset and Severity of Severe Acute Respiratory Syndrome Coronavirus 2 Infection. J Am Heart Assoc. Apr. 9, 2020;9(7):e0162219 in 5 pages.

Guo et al., The Serum Profile of Hypercytokinemia Factors Identified in H7N9-Infected Patients Can Predict Fatal Outcomes. Sci Rep. 2015;5(1):srep10942 in 10 pages.

Guo et al., IL-15 Superagonist-Mediated Immunotoxicity: Role of NK Cells and IFN-γ. J Immunol. Sep. 1, 2015;195(5):2353-2364.

Guo et al., IL-15 Enables Septic Shock by Maintaining NK Cell Integrity and Function. J Immunol. Feb. 1, 2017;198(3):1320-1333.

Guo et al., The Origin, Transmission and Clinical Therapies on Coronavirus Disease 2019 (COVID-19) Outbreak—An Update on the Status. Military Med Res. Dec. 2020;7(1):10 pages.

Han et al., The acute respiratory distress syndrome: from mechanism to translation. J Immunol. Feb. 1, 2015;194(3):855-860.

Han et al., Cytokine profiles as novel diagnostic markers of Epstein-Barr virus-associated hemophagocytic lymphohistiocytosis in children. J Crit Care. Jun. 1, 2017;39:72-77.

Hao et al., Mathematical Model of Sarcoidosis. PNAS. Nov. 11, 2014;111(45):16065-16070.

Harris et al.,. Reciprocal Regulation of Polarized Cytokine Production by Effector B and T Cells. Nat Immunol. Dec. 2000;1(6):475-482.

Haugen et al., Cytokine Concentrations in Plasma from Children with Severe and Non-Severe Community Acquired Pneumonia. PLoS One. Sep. 25, 2015;10(9):e0138978 in 16 pages.

Hechinger et al., Therapeutic Activity of Multiple Common γ-chain Cytokine Inhibition in acute and chronic GVHD. Blood. Jan. 15, 2015;125(3):570-580.

Hogaboam et al., Differential monocyte chemoattractant protein-1 and chemokine receptor 2 expression by murine lung fibroblasts derived from Th1- and Th2-type pulmonary granuloma models. J Immunol. Aug. 15, 1999;163(4):2193-2201.

Hondowicz et al., Interleukin-2-Dependent Allergen-Specific Tissue-Resident Memory Cells Drive Asthma. Immunity. Jan. 19, 2016;44(1):155-166.

Hornef et al., Cytokine production in a whole-blood assay after Epstein-Barr virus infection in vivo. Clin Diagn Lab Immunol. Mar. 1995;2(2):209-213.

Huang et al. Innate and Adaptive Immune Responses in Patients with Pandemic Influenza A(H1N1)pdm09. Arch Virol. Nov. 2013;158(11):2267-2272.

Huang et al., Clinical Features of Patients Infected with 2019 Novel Coronavirus in Wuhan, China. Lancet. Feb. 15, 2020;395(10223):497-506.

Hunninghake et al., Mechanisms of Hypergammaglobulinemia in Pulmonary Sarcoidosis: Site of Increased Antibody Production and Role of T Lymphocytes. J Clin Invest. Jan. 1, 1981;67(1):86-92.

Jabri et al., IL-15 Functions as a Danger Signal to Regulate Tissue-Resident T Cells and Tissue Destruction. Nat Rev Immunol. Dec. 2015;15(12):771-783.

Jarvis et al., Neutrophils: The Forgotten Cell in JIA Disease Pathogenesis. Pedia Rheumatol Online. Dec. 2007;5(1):1-8.

Jia et al., Detection of IL-9 Producing T Cells in the PBMCs of Allergic Asthmatic Patients. BMC immunol. Dec. 2017;18(1):1-9.

(56) References Cited

OTHER PUBLICATIONS

Jillella et al., Non-Hodgkins Lymphoma Presenting as Anasarca: Probably Mediated by Tumor Necrosis Factor Alpha (TNF-α). Leuk Lymph. Jan. 1, 2000;38(3-4):419-22.
Jiménez-Sousa et al., IL15 Polymorphism is Associated with Advanced Fibrosis, Inflammation-Related Biomarkers and Virological Response in Human Immunodeficiency Virus/Hepatitis C Virus Coinfection. Liver Int. Jan. 2016;36:1258-1266.
Kahaleh et al., Interleukin-2 in scleroderma: Correlation of serum level with extent of skin involvement and disease duration. Ann Intern Med. Mar. 15, 1989;110(6):446-450.
Kalyan et al., Human Peripheral Gammadelta T Cells Potentiate the Early Proinflammatory Cytokine Response to Staphylococcal Toxic Shock Syndrome toxin-1. J Infect Dis. May 15, 2004;189(10):1892-1896.
Kappler et al., V Beta-Specific Stimulation of Human T Cells by Staphylococcal Toxins. Science. May 19, 1989;244(4906):811-813.
Khan et al., IL-2 Regulates SEB Induced Toxic Shock Syndrome in BALB/c Mice. PLoS One. Dec. 29, 2009;4(12):e8473 in 6 pages.
Kim et al., Targeting the IL-15 Receptor with an Antagonist IL-15 Mutant/Fcγ2a Protein Blocks Delayed-Type Hypersensitivity. J Immunol. Jun. 15, 1998;160(12):5742-5748.
Kimber et al., Toxic Shock Syndrome: Characterization of Human Immune Responses to TSST-1 and Evidence for Sensitivity Thresholds. Toxicol Sci. Jul. 1, 2013;134(1):49-63.
Kimura et al., The Postoperative Serum Interleukin-15 Concentration Correlates with Organ Dysfunction and the Prognosis of Septic Patients Following Emergency Gastrointestinal Surgery. J Surg Res. Jun. 15, 2012;175(2):e83-88.
Klingström et al., Innate and Adaptive Immune Responses against Human Puumala Virus Infection: Immunopathogenesis and Suggestions for Novel Treatment Strategies for Severe Hantavirus-Associated Syndromes. J Intern Med. May 2019; 285(5):510-523.
Koh et al., Levels of Interleukin-2, Interferon-gamma, and Interleukin-4 in Bronchoalveolar Lavage Fluid from Patients with Mycoplasma Pneumonia: Implication of Tendency Toward Increased Immunoglobulin E Production. Pediatrics. Mar. 1, 2001;107(3):E39-E45.
Krakauer T., Immune Response to Staphylococcal Superantigens. Immunol Res. Dec. 1999;20(3):163-173.
Krieg et al., Improved IL-2 immunotherapy by selective stimulation of IL-2 receptors on lymphocytes and endothelial cells. PNAS. Jun. 29, 2010;107(26):11906-11911.
Kurane et al., Activation of T Lymphocytes in Dengue Virus Infections. High Levels of Soluble Interleukin 2 Receptor, Soluble CD4, Soluble CD8, Interleukin 2, and Interferon-Gamma in Sera of Children with Dengue. J Clin Invest. Nov. 1, 1991;88(5):1473-1480.
Kushner et al., Immune Biomarker Differences and Changes Comparing HCV Mono-Infected, HIV/HCV Co-Infected, and HCV Spontaneously Cleared Patients. PLoS One. Apr. 4, 2013;8(4):e60387 in 17 pages.
Lamparello et al., Severely Injured Trauma Patients with High Circulating IL-15 Levels Display Worse Outcomes and Distinct Inflammatory Profiles, Suggesting a Role for Natural Killer Cell Activation. J Am Coll Surg. Oct. 1, 2019;229(4):S310.
Lashine et al., Correcting the Expression of MiRNA-155 Represses PP2Ac and Enhances the Release of IL-2 in PBMCs of Juvenile SLE Patients. Lupus. Mar. 2, 2015;24(3):240-247.
Leahy et al., Interleukin-15 Is Associated with Disease Severity in Viral Bronchiolitis. Eur Resp J. Jan. 1, 2015;47(1):212-222.
Lee et al. Regulation of CAR T Cell-Mediated Cytokine Release Syndrome-like Toxicity Using Low Molecular Weight Adapters. Nat Commun. Jun. 18, 2019;10(1):1-11.
Lentsch et al., Mechanisms of Leukocyte-Mediated Tissue Injury Induced by Interleukin-2. Cancer Immunol Immunother. Jan. 1999;47(5):243-248.
Lesur et al., Interleukin-2 Involvement in Early Acute Respiratory Distress Syndrome: Relationship with Polymorphonuclear Neutrophil Apoptosis and Patient Survival. Crit Care Med. Dec. 1, 2000;28(12):3814-3822.
Li et al., Structure-Function Studies of T-Cell Receptor-Superantigen Interactions. Immunol Rev. Jun. 1998;163(1):177-186.
Li et al., CD3 bispecific antibody-induced cytokine release is dispensable for cytotoxic T cell activity. Sci Transl Med. Sep. 4, 2019;11(508):eaax8861 in 13 pages.
Li et al., IL-9 Deficiency Promotes Pulmonary Th17 Response in Murine Model of Pneumocystis Infection. Front Immunol. May 25, 2018;9:Art1118 in 16 pages.
Li et al., Coronavirus Neurovirulence Correlates with the Ability of the Virus to Induce Proinflammatory Cytokine Signals from Astrocytes and Microglia. J Virol. Apr. 1, 2004;78(7):3398-3406.
Lin et al., Expression and regulation of interleukin-9 in chronic rhinosinusitis. Am J Rhinol Allergy. Jan. 2015;29(1):e18-e23.
Lin et al., Temporal Characterization of Marburg Virus Angola Infection Following Aerosol Challenge in Rhesus Macaques. J Virol. Oct. 1, 2015;89(19):9875-9885.
Linde et al., Serum levels of lymphokines and soluble cellular receptors in primary Epstein-Barr virus infection and in patients with chronic fatigue syndrome. J Infect Dis. Jun. 1, 1992;165(6):994-1000.
Link et al., Anti-CD3-based Bispecific Antibody Designed for Therapy of Human B-cell Malignancy can Induce T-cell Activation by Antigen-Dependent and Antigen-Independent Mechanisms. Int J Cancer. Jul. 17, 1998;77(2):251-256.
Lisi et al., Sjögrens Syndrome Autoantibodies Provoke Changes in Gene Expression Profiles of Inflammatory Cytokines Triggering a Pathway Involving TACE/NF-κB. Lab Invest. Apr. 2012;92(4):615-624.
Liu et al., Differences in Inflammatory Marker Patterns for Adult Community-Acquired Pneumonia Patients Induced by Different Pathogens. Clin Respir J. Mar. 2018;12(3):974-985.
Liu et al., Overlapping and Discrete Aspects of the Pathology and Pathogenesis of the Emerging Human Pathogenic Coronaviruses SARS-CoV, MERS-CoV, and 2019-NCOV. J Med Virol. May 2020;92(5):491-494.
Liu et al., Longitudinal Characteristics of Lymphocyte Responses and Cytokine Profiles in the Peripheral Blood of SARS-CoV-2 Infected Patients. EBioMedicine. May 1, 2020;55:102763 in 17 pages.
Logan et al., Increased disease activity in a patient with sarcoidosis after high dose interleukin 2 treatment for metastatic renal cancer. Thorax. Jul. 1, 2005;60(7):610-611.
Lotz et al., Release of lymphokines after Epstein Barr virus infection in vitro. I. Sources of and kinetics of production of interferons and interleukins in normal humans. J Immunol. May 15, 1986;136(10):3636-3642.
Lourdes et al., Systemic Capillary Leak Syndrome as an Initial Presentation of ALK-Negative Anaplastic Large Cell Lymphoma. Case Rep Hematol. Mar. 26, 2012;2012:Article ID 954201 in 4 pages.
Macaubas et al., Oligoarticular and Polyarticular JIA: Epidemiology and Pathogenesis. Nat Rev Rheumatol. Nov. 2009;5(11):616-626.
Mahallawi et al., MERS-CoV Infection in Humans Is Associated with a pro-Inflammatory Th1 and Th17 Cytokine Profile. Cytokine. Apr. 1, 2018;104:8-13.
Makarevich et al., Interleukin-2 (IL-2) and Interferon-γ (IFN- γ) in Identifying Severe Community-Acquired Pneumonia (SCAP) Clinical Outcomes and Complications. Eur Resp J. 2011;38:1474;Abstract.
Maleki et al., Serum Markers Associated with Severity and Outcome of Hantavirus Pulmonary Syndrome. J Infect Dis. May 5, 2019;219(11):1832-1840.
Massoud et al., Common γ-chain 1,9,15 blocking peptide reduces in vitro immune activation markers in HTLV-1-associated myelopathy/tropical spastic paraparesis. PNAS. Sep. 1, 2015;112(35):11030-11035.
McElroy et al., Ebola Hemorrhagic Fever: Novel Biomarker Correlates of Clinical Outcome. J Infect Dis. Aug. 15, 2014;210(4):558-566.
McElroy et al., Human Ebola Virus Infection Results in Substantial Immune Activation. PNAS. Apr. 14, 2015;112(15):4719-4724.

(56) References Cited

OTHER PUBLICATIONS

McKinstry et al., Memory CD4 T Cell-Derived IL-2 Synergizes with Viral Infection to Exacerbate Lung Inflammation. PLoS Pathog. Aug. 14, 2019;15(8):e1007989 in 24 pages.

Mehta et al., COVID-19: Consider Cytokine Storm Syndromes and Immunosuppression. Lancet. Mar. 28, 2020;395(10229):1033-1034.

Mo et al., Induction of Cytokines in Mice with Parainfluenza Pneumonia. J Virol. Feb. 1995;69(2):1288-1291.

Moretti et al., A Mast Cell-ILC2-Th9 Pathway Promotes Lung Inflammation in Cystic Fibrosis. Nat Commun. Jan. 16, 2017;8(1):14017 in 13 pages.

Mori et al., High Levels of Cytokine-Producing Cells in the Lung Tissues of Patients with Fatal Hantavirus Pulmonary Syndrome. J Infect Dis. Feb. 1, 1999;179(2):295-302.

Muro et al., Expression of IL-15 in Inflammatory Pulmonary Diseases. J Allergy Clin Immunol. Dec. 1, 2001;108(6):970-975.

Nakamura et al., Interleukin-15 Is Critical in the Pathogenesis of Influenza A Virus-Induced Acute Lung Injury. J Virol. Jun. 1, 2010;84(11):5574-5582.

NCBI Reference Sequence: XP_012498189 Predicted: interleukin-15 [Propithecus coquereli], Jun. 1, 2015.

Needleman et al., Interleukin-1, interleukin-2, interleukin-4, interleukin-6, tumor necrosis factor α, and interferon-γ levels in sera from patients with scleroderma. Arthritis Rheum. Jan. 1992;35(1):67-72.

Nordberg et al., Cytotoxic mechanisms may play a role in the local immune response in the central nervous system in neuroborreliosis. J Neuroimmunol. Mar. 1, 2011;232(1-2):186-193.

Notarnicola et al., Correlation between serum levels of IL-15 and IL-17 in patients with idiopathic inflammatory myopathies. Scand J Rheumatol. May 4, 2015;44(3):224-228.

Okamoto et al., Interleukin 18 (IL-18) in Synergy with IL-2 Induces Lethal Lung Injury in Mice: A Potential Role for Cytokines, Chemokines, and Natural Killer Cells in the Pathogenesis of Interstitial Pneumonia. Blood Feb. 15, 2002;99(4):1289-1298.

Olcott et al., Interleukin-9 and interleukin-17C in chronic rhinosinusitis. Int Forum Allergy Rhinol. Aug. 2016;6(8):841-847.

Orucevic et al., Role of nitric oxide in IL-2 therapy-induced capillary leak syndrome. Cancer Metastasis Rev. Mar. 1998;17(1):127-142.

Outinen et al., Thrombocytopenia Associates with the Severity of Inflammation and Variables Reflecting Capillary Leakage in Puumala Hantavirus Infection, an Analysis of 546 Finnish Patients. Infect Dis (Lond) Sep. 1, 2016;48(9):682-687.

Ozsurekci et al., Can the Mild Clinical Course of Crimean-Congo Hemorrhagic Fever in Children Be Explained by Cytokine Responses? J Med Virol. Nov. 2013;85(11):1955-1959.

Panupattanapong et al., New spectrum of COVID-19 manifestations in children: Kawasaki-like syndrome and hyperinflammatory response. Cleve Clin J Med. Dec. 31, 2020; in 7 pages.

Papa et al., Emergence of Crimean-Congo Haemorrhagic Fever in Greece. Clin Microbiol Infection. Jul. 1, 2009;16(7):843-847.

Papa et al., Cytokines as Biomarkers of Crimean-Congo Hemorrhagic Fever. J Med Virol. Jan. 2016;88(1):21-27.

Parsonnet et al., Mediators in the Pathogenesis of Toxic Shock Syndrome: Overview. Rev Infect Dis. Jan. 1, 1989;S263-S269.

Patro et al., Cytokine Signature Associated with Disease Severity in Dengue. Viruses. Jan. 8, 2019;11(1):34 in 12 pages.

Pattanaik et al., Pathogenesis of Systemic Sclerosis. Front Immunol. Jun. 8, 2015;6:272 in 40 pages.

Pietikäinen et al., Cerebrospinal fluid cytokines in Lyme neuroborreliosis. J Neuroinflam. Dec. 2016;13(1):273 in 10 pages.

Poust et al., Management of Toxicities Associated with High-Dose Interleukin-2 and Biochemotherapy. Anticancer Drugs. Jan. 1, 2013;24(1):1-13.

Prasse et al., Th1 Cytokine Pattern in Sarcoidosis Is Expressed by Bronchoalveolar CD4 and CD8 T Cells. Clin Exp Immunol. Nov. 2000;122(2):241-248.

Prior et al., Increased Levels of Serum Interferon-Gamma in Pulmonary Sarcoidosis and Relationship with Response to Corticosteroid Therapy. Am Rev Respir Dis. Jan. 1, 1991;143(1):53-60.

Rafi et al., Evidence for the Involvement of Fas Ligand and Perforin in the Induction of Vascular Leak Syndrome. J Immunol. Sep. 15, 1998;161(6):3077-3086.

Rai et al., Serum Cytokine Profile in Patients with Chronic Rhinosinusitis with Nasal Polyposis Infected by Aspergillus flavus. Ann Lab Med. Mar. 28, 2018;38(2):125-131.

Ramos-Casals et al., Adult Haemophagocytic Syndrome. Lancet. Apr. 26, 2014;383(9927):1503-1516.

Rauer et al., Lyme Neuroborreliosis. Dtsch Arztebl Int 2018;115:751-756.

Robinson et al., Gamma Interferon Is Spontaneously Released by Alveolar Macrophages and Lung T Lymphocytes in Patients with Pulmonary Sarcoidosis. J Clin Invest May 1, 1985;75(5):1488-1495.

Roediger et al., IL-2 Is a Critical Regulator of Group 2 Innate Lymphoid Cell Function during Pulmonary Inflammation. J Allergy Clin Immunol. Dec. 1, 2015;136(6):1653-1663.

Ruiz et al., Animal Models of Human Viral Diseases. In Animal Models for the Study of Human Disease. 2013; Chapter 38: 927-970.

Ruprecht et al., Coexpression of CD25 and CD27 Identifies FoxP3+ Regulatory T Cells in Inflamed Synovia. J Exp Med. Jun. 6, 2005;201(11):1793-1803.

Russier et al., The Exonuclease Domain of Lassa Virus Nucleoprotein Is Involved in Antigen-Presenting-Cell-Mediated NK Cell Responses. J Virol. Dec. 1, 2014;88(23):13811-13820.

Sadeghi et al., Cytokine Expression during Early and Late Phase of Acute Puumala Hantavirus Infection. BMC Immunol. Dec. 2011;12(1):65 in 10 pages.

Sambatakou et al., Cytokine Profiling of Pulmonary Aspergillosis. Int J Immunogenet. Aug. 2006;33(4):297-302.

Sarawar et al., Cytokine Profiles of Bronchoalveolar Lavage Cells from Mice with Influenza Pneumonia: Consequences of CD4+ and CD8+ T Cell Depletion. Reg Immunol. May 1993;5(3-4):142-150.

Sarawar et al., Concurrent Production of Interleukin-2, Interleukin-10, and γ Interferon in the Regional Lymph Nodes of Mice with Influenza Pneumonia. J Virol. May 1994;68(5):3112-3119.

Schaeffer et al., Lassa Virus Activates Myeloid Dendritic Cells but Suppresses Their Ability to Stimulate T Cells. PLoS Pathog. Nov. 12, 2018;14(11):e1007430 in 25 pages.

Schaeffer et al., Non-Pathogenic Mopeia Virus Induces More Robust Activation of Plasmacytoid Dendritic Cells than Lassa Virus. Viruses. Mar. 21, 2019;11(3):287 in 9 pages.

Schlosser et al., Mucous Cytokine Levels in Chronic Rhinosinusitis-Associated Olfactory Loss. JAMA Otolaryngol Head Neck Surg. Aug. 1, 2016;142(8):731-737.

Schulert et al., Macrophage Activation Syndrome and Cytokine-Directed Therapies. Best Pract Res Clin Rheumatol. Apr. 1, 2014;28(2):277-292.

Segawa et al., Inhibition of Transforming Growth Factor-β Signalling Attenuates Interleukin (IL)-18 plus IL-2-Induced Interstitial Lung Disease in Mice. Clin Exp Immunol. 2010;160:394-402.

Semenzato et al., Immune Mechanisms in Interstitial Lung Diseases. Allergy. Dec. 2000;55(12):1103-1120.

Shaw et al., Weathering a Cytokine Storm: A Case of EBV-Induced Hemophagocytic Lymphohistiocytosis. J Invest Med High Impact Case Rep. Apr. 28, 2016;4(2):1-5.

Shimbara et al., IL-9 and Its Receptor in Allergic and Nonallergic Lung Disease: Increased Expression in Asthma. J Allergy Clin Immunol. Jan. 1, 2000;105(1):108-115.

Silversides et al., Staphylococcal Toxic Shock Syndrome: Mechanisms and Management. Curr Infect Dis Rep. Sep. 2010;12(5):392-400.

Singer et al., The Third International Consensus Definitions for Sepsis and Septic Shock (Sepsis-3). JAMA. Feb. 23, 2016;315(8):801-810.

Sisto et al., Interleukin-15 as a Potential New Target in Sjögrens Syndrome-Associated Inflammation. Pathology. Oct. 1, 2016;48(6):602-607.

(56) References Cited

OTHER PUBLICATIONS

Sisto et al., TLR2 Signals via NF-κB to Drive IL-15 Production in Salivary Gland Epithelial Cells Derived from Patients with Primary Sjögren's Syndrome. Clin Exp Med. Aug. 2017;17(3):341-350.
Smith et al., Persistent Crimean-Congo Hemorrhagic Fever Virus Infection in the Testes and within Granulomas of Non-Human Primates with Latent Tuberculosis. PLoS Pathog. Sep. 26, 2019;15(9):e1008050 in 22 pages.
Smith et al., A Prominent Role for the IL1 Pathway and IL15 in Susceptibility to Chronic Cavitary Pulmonary Aspergillosis. Clin Microbiol Infect. Aug. 1, 2014;20(8):O480-O488.
Smith et al., Clinical Implications of Interferon-. Genetic and Epigenetic Variants. Immunology. Dec. 2014;143(4):499-511.
Smolewska et al., Regulation of Peripheral Blood and Synovial Fluid Lymphocyte Apoptosis in Juvenile Idiopathic Arthritis. Scand J Rheumatol. Jan. 1, 2004;33(1):7-12.
Soussi-Gounni et al., Role of IL-9 in the Pathophysiology of Allergic Diseases. J Allergy Clin Immunol. Apr. 1, 2001;107(4):575-582.
Stern et al., Stevens-Johnson Syndrome and Toxic Epidermal Necrolysis: Associations, Outcomes, and Pathobiology—Thirty Years of Progress but Still Much to be Done. J Invest Dermatol. May 1, 2017;137(5):1004-1008.
Streckfus et al., Cytokine Concentrations in Stimulated Whole Saliva among Patients with Primary Sjogren's Syndrome, Secondary Sjögrens Syndrome, and Patients with Primary Sjögrens Syndrome Receiving Varying Doses of Interferon for Symptomatic Treatment of the Condition: A Preliminary Study. Clin Oral Investig. Jun. 2001;5(2):133-135.
Strengell et al., IL-21 in Synergy with IL-15 or IL-18 Enhances IFN-γ Production in Human NK and T Cells. J Immunol. Jun. 1, 2003;170(11):5464-5469.
Su et al., Interleukin-15 Is Associated with Severity and Mortality in Stevens-Johnson Syndrome/Toxic Epidermal Necrolysis. J Invest Dermatol. May 1, 2017;137(5):1065-1073.
Sugimoto et. al., IL-9 Blockade Suppresses Silica-Induced Lung Inflammation and Fibrosis in Mice. Am J Respir Cell Mol Biol. Feb. 2019;60(2):232-243.
Sullivan et al., Ebola Virus Pathogenesis: Implications for Vaccines and Therapies. J Virol. Sep. 15, 2003;77(18):9733-9737.
Suntharalingam et al., Cytokine storm in a phase 1 trial of the anti-CD28 monoclonal antibody TGN1412. N Engl J Med. Sep. 7, 2006;355(10):1018-1028.
Tan et al., Acute Myocarditis Following High-Dose Interleukin-2 Treatment. J Cardiol Cases. Jan. 1, 2016;15(1):28-31.
Temann et al., Pulmonary Overexpression of IL-9 Induces Th2 Cytokine Expression, Leading to Immune Pathology. J Clin Invest. Jan. 1, 2002;109(1):29-39.
Temann et al., IL9 Leads to Airway Inflammation by Inducing IL13 Expression in Airway Epithelial Cells. Int Immunol. Jan. 1, 2007;19(1):1-10.
Thiant et al., Plasma Levels of IL-7 and IL-15 in the First Month after Myeloablative BMT Are Predictive Biomarkers of Both Acute GVHD and Relapse. Bone Marrow Trans. Oct. 2010;45(10):1546-1552.
Tisoncik et al., Into the eye of the cytokine storm. Microbiol Mol Biol Rev. Mar. 2012;76(1):16-32.
Tokman et. al., The Pathogenesis of Experimental Toxic Shock Syndrome: The Role of Interleukin-2 in the Induction of Hypotension and Release of Cytokines. Shock Feb. 1, 1995;3(2):145-151.
Tourkova et al., Restoration by IL-15 of MHC Class I Antigen-Processing Machinery in Human Dendritic Cells Inhibited by Tumor-Derived Gangliosides. J Immunol. Sep. 1, 2005;175(5):3045-3052.
Trottestam et. al., Chemoimmunotherapy for Hemophagocytic Lymphohistiocytosis: Long-Term Results of the HLH-94 Treatment Protocol. Blood. Oct. 27, 2011;118(17):4577-4584.
Tsoutsou et al., Cytokine Levels in the Sera of Patients with Idiopathic Pulmonary Fibrosis. Respir Med. May 1, 2006;100(5):938-945.
Uchiyama et al., Study of the Biological Activities of Toxic Shock Syndrome Toxin-1. Proliferative Response and Interleukin 2 Production by T Cells Stimulated with the Toxin. Microbiol Immunol. May 1986;30(5):469-483.
Ueda et al., Serum Interleukin-15 Level Is a Useful Predictor of the Complications and Mortality in Severe Acute Pancreatitis. Surgery. Sep. 1, 2007;142(3):319-326.
Van Den Brûle et al., Profibrotic Effect of IL-9 Overexpression in a Model of Airway Remodeling. Am J Respir Cell Mol Biol. Aug. 2007;37(2):202-209.
Veenhuis et al., Systemic Elevation of Proinflammatory Interleukin 18 in HIV/HCV Coinfection versus HIV or HCV Monoinfection. Clin Infect Dis. Mar. 2017;64(5):589-596.
Via et al. Kinetics of T Cell Activation in Acute and Chronic Forms of Murine Graft-versus-Host Disease. J Immunol. Apr. 15, 1991;146(8):2603-2609.
Via et al., Critical Role of Interleukin-2 in the Development of Acute Graft-versus-Host Disease. Int Immunol. Jun. 1, 1993;5(6):565-572.
Villinger et al., Markedly Elevated Levels of Interferon (IFN)-γ, IFN-α, Interleukin (IL)-2, IL-10, and Tumor Necrosis Factor- α Associated with Fatal Ebola Virus Infection. J Infect Dis. 1999;179:S188-S191.
Vissinga et al. TCR Expression and Clonality Analysis in Pulmonary Sarcoidosis. Hum Immunol. Jun. 1, 1996;48(1-2):98-106.
Waldmann et al., The Multifaceted Regulation of Interleukin-15 Expression and the Role of this Cytokine in Nk Cell Differentiation and Host Response to Intracellular Pathogens. Annu Rev Immunol. 1999;17:19-49.
Wang et al., Biomarkers of Cytokine Release Syndrome and Neurotoxicity Related to CAR-T Cell Therapy. Biomark Res. Dec. 2018;6(1):4 in 10 pages.
Wang et al., "IL-2 and IL-15 blockade by BNZ-1, an inhibitor of selective [gamma]-chain cytokines, decreases leukemic T-cell viability". Leukemia. May 2019;33(5):1243-1255.
Watanabe et al., Pro-inflammatory and anti-inflammatory T cells in giant cell arteritis. Jt Bone Spine. Jul. 1, 2017;84(4):421-426.
Wauquier et al., Human Fatal Zaire Ebola Virus Infection is Associated with an Aberrant Innate Immunity and with Massive Lymphocyte Apoptosis. PLoS Negl Trop Dis. Oct. 5, 2010;4(10):e837 in 10 pages.
Wei et al., Activation of Tumor Necrosis Factor-Alpha Production from Human Neutrophils by IL-2 via IL-2-Rβ. J Immunol. Mar. 1, 1993;150:1979-1987.
Welbourn et al., Involvement of Thromboxane and Neutrophils in Multiple-System Organ Edema with Interleukin-2. Ann Surg. Dec. 1990;212(6):728-733.
Welbourn et al., Interleukin-2 Induces Early Multisystem Organ Edema Mediated by Neutrophils. Ann Surg. Aug. 1991;214(2):181-186.
Welch et al., Fluorescent Crimean-Congo Hemorrhagic Fever Virus Illuminates Tissue Tropism Patterns and Identifies Early Mononuclear Phagocytic Cell Targets in Ifnar-/- Mice. PLoS Pathog. Dec. 2, 2019;15(12):e1008183 in 23 pages.
Weyand et al., Disease patterns and tissue cytokine profiles in giant cell arteritis. Arthritis Rheum. Jan. 1997;40(1):19-26.
White et al. Cardiopulmonary Toxicity of Treatment with High Dose Interleukin-2 in 199 Consecutive Patients with Metastatic Melanoma or Renal Cell Carcinoma. Cancer. Dec. 15, 1994;74(12):3212-3222.
Williams et al., The Mercurial Nature of Neutrophils: Still an Enigma in ARDS? Am J Physiol Lung Cell Mol Physiol. Feb. 1, 2014;306(3):L217-L230.
Winn et al., Selective Effects of Interleukin (IL)-15 on Antifungal Activity and IL-8 Release by Polymorphonuclear Leukocytes in Response to Hyphae of Aspergillus Species. J Infect Dis. Aug. 15, 2003;188(4):585-590.
Wuttge et al., Serum IL-15 in patients with early systemic sclerosis: a potential novel marker of lung disease. Arthritis Res Ther. Oct. 2007;9(5):1-9.
Xie et al., Inflammatory Markers of the Systemic Capillary Leak Syndrome (Clarkson Disease). J Clin Cell Immunol. 2014;5:1000213 in 15 pages.

(56) References Cited

OTHER PUBLICATIONS

Xu et al., IL-9 Blockade Attenuates Inflammation in a Murine Model of Methicillin-Resistant *Staphylococcus aureus* Pneumonia. Acta Biochim Biophys Sin. Feb. 2020;52(2):133-140.
Yang et al., Interleukin-2 and Lymphocyte-Induced Eosinophil Proliferation and Survival in Asthmatic Patients. J Allergy Clin Immunol. Mar. 1, 1993;91(3):792-801.
Yang et al., Epstein-Barr virus (EBV)-encoded RNA promotes growth of EBV-infected T cells through interleukin-9 induction. Cancer Res. Aug. 1, 2004;64(15):5332-5337.
Yang et al., TCR Engagement Negatively Affects CD8 but Not CD4 CAR T Cell Expansion and Leukemic Clearance. Sci Transl Med. Nov. 22, 2017;9(417):eaag1209 in 23 pages.
Yarkoni et al., IL-2-targeted therapy ameliorates the severity of graft-versus host disease: Ex vivo selective depletion of host-reactive T cells and in vivo therapy. Biol Blood Marrow Transplant. Apr. 1, 2012;18(4);523-535.
Youinou et al., Disturbance of Cytokine Networks in Sjogren's Syndrome. Arthritis Res Ther. Aug. 2011;13(4):227 in 10 pages.
Younan et al., Ebola Virus Binding to Tim-1 on T Lymphocytes Induces a Cytokine Storm. MBio. Sep. 26, 2017;8(5):00847-17.
Younan et al., Ebola Virus-Mediated T-Lymphocyte Depletion Is the Result of an Abortive Infection. PLoS Pathog. Oct. 24, 2019;15(10):e1008068 in 25 pages.
Yuki et al., COVID-19 pathophysiology: A review. Clin Immunol. Jun. 1, 2020;215:108427 in 7 pages.
Zhang et al., Potent and Selective Stimulation of Memory-Phenotype CD8 T Cells In Vivo by IL-15. Immunity. May 1, 1998;8(5):591-599.
Zhou et al., Th2 cytokines and asthma. Interleukin-9 as a therapeutic target for asthma. Respir Res. Apr. 2001;2(2):80-84.
Zinter et al. Calming the Storm in HLH. Blood Jul. 11, 2019;134:103-104.
Aoi et al., "IL-15 prevents allergic rhinitis through reactivation of antigen-specific CD8+ cells". J Aller Clin Immunol. (2006) 117(6): 1359-1366.
Boraschi et al., "Cytokine Receptors—Interleukin 2 Receptor Gamma—An overview", in Encyclopedia of Endocrine Diseases, (2004); downloaded from https://www.sciencedirect.com/topics/medicine-and-dentristry/interleukin-2-receptor-gamma; 2 pages.
Cagdas et al., "Genomic spectrum and phenotypic heterogeneity of human IL-21 receptor deficiency". J Clin Immunol. (Apr. 2021) 41: 1272-1290.
Crane et al., "Exercise-stimulated interleukin-15 is controlled by AMPK and regulates skin metabolism and aging." Aging Cell (2015) 14(4): 625-634.
Enose-Akahata et al., "Clinical trial of a humanized anti-IL-2/IL-15 receptor β chain in HAM/TSP." Ann Clin Translation Neurol. (2019) 6(8): 1383-1394.
Hiromura et al., "IL-21 Administration into the nostril alleviates murine allergic rhinitis". J Immunol. (2007) 179(10): 7157-7165.
Huang et al., "Nuclear factor-κB-dependent reversal of aging-induced alterations in T cell cytokines." FASEB J. (2008) 22(7): 2142-2150.
MAYO Clinic. "Hay Fever—Symptoms and Causes", Mayo Foundation for Medical Research (MFMER) © 1998-2021; 4 pages.
Nata et al., "Targeting the binding interface on a shared receptor subunit of a cytokine family enables the inhibition of multiple member cytokines with selectable target spectrum." Journal of Biological Chemistry (2015) 290(37): 22338-22351.
Nozuma et al., "Human T-lymphotropic virus type 1 (HTLV-1) and cellular immune response in HTLV-1-associated myelopathy/tropical spastic paraparesis." J NeuroVirol. (Jul. 2020) 26: 652-663.
Pepper et al., "Different routes of bacterial infection induce long-lived TH 1 memory cells and short-lived TH 17 cells." Nature Immunolo.gy 11.1 (2010): 83-89.
Rajaei et al., "Role of IL-21 in HTLV-1 infections with emphasis on HTLV-1-associated myelopathy/tropical spastic paraparesis (HAM/TSP)." Med Microbiol Immunol. (2017) 206(3): 195-201.
Venkateshaiah et al., "Regulatory effects of IL-15 on allergen-induced airway obstruction". J Aller Clin Immunology 141.3 (2018): 906-917.
Wu et al., "IL-21 alleviates allergic asthma in DOCK8-knockout mice". Biochem Biophys Res Commun. (2018) 501(1): 92-99.
Office Action dated Oct. 21, 2021 in U.S. Appl. No. 15/767,133.
Price-Troska et al., Inhibiting IL-2 Signaling And The Regulatory T-Cell Pathway Using Computationally Designed Peptides, Invest New Drugs, (2018) 37(1): 9-16.
International Search Report and Written Opinion dated Aug. 14, 2020 for PCT/US2020/030772.
Ciszewski et al., Identification of a γc receptor antagonist that prevents reprogramming of human tissue-resident cytotoxic T cells by IL15 and IL21. Gastroenterol. (Feb. 1, 2020) 158(3): 625-637.
Office Action dated Jan. 29, 2021 in Canadian Application No. 2824515.
Office Action dated Sep. 24, 2021 in Chinese Application No. 201810863447.X.
Office Action dated Feb. 19, 2021 in European Application No. 19206731.2.
Office Action dated Feb. 23, 2021 in In Canadian Application No. 3000207.
Office Action dated Dec. 24, 2020 in Chinese Application No. 201680058779.X.
Office Action dated Sep. 17, 2021 in Chinese Application No. 201680058779.X.
Examination Report dated Dec. 9, 2020 in India Application No. 201817014941.
International Search Report and Written Opinion dated Dec. 21, 2021 for PCT/US2021/038512.
Office Action dated Dec. 24, 2021 for U.S. Appl. No. 17/012,724.
Office Action dated Dec. 29, 2021 in U.S. Appl. No. 16/294,733.
Biology Online, "Codon", Definition from https://www.biologyonline.com/dictionary/codon; accessed May 26, 2022 (Year: 2022) 12 pages.
Gillies et al., "Bi-functional cytokine fusion proteins for gene therapy and antibody-targeted treatment of cancer". Cancer Immunol Immunother. (2002) 51: 449-460.
Office Action dated Jun. 2, 2022 for U.S. Appl. No. 17/012,724.
Office Action dated Jun. 9, 2022 in U.S. Appl. No. 16/294,733.
Restriction Requirement dated Mar. 4, 2022 in U.S. Appl. No. 17/083,099.
Notice of Allowance dated May 27, 2022 in U.S. Appl. No. 17/083,099.
Notice of Allowance dated Mar. 31, 2022 in U.S. Appl. No. 15/767,133.
Notice of Acceptance dated Jun. 11, 2021 for Australian Patent Application No. 2019202527.
Office Action dated Feb. 26, 2021 for Chinese Patent Application No. 201810863447.X.
Office Action dated Aug. 17, 2021 in Japanese Application No. 2019-152602.
Office Action dated Mar. 18, 2021 in Australian Application No. 2020201174.
Office Action dated May 12, 2021 in Australian Patent Application No. 2018250210.
Office Action dated Jul. 22, 2021 in U.S. Appl. No. 16/294,733.
Office Action dated Feb. 11, 2021 in U.S. Appl. No. 15/767,133.
Lerkvaleekul et al., Macrophage Activation Syndrome: Early Diagnosis Is Key. Open Access Rheumatol. 2018;10: 117-128.

\* cited by examiner

SEQ ID NO: Alignment of the D-helix region sequence of human γc-family cytokines

| SEQ ID NO | Cytokine | | | | | | | | | | | | | | | | | |
|---|---|---|---|---|---|---|---|---|---|---|---|---|---|---|---|---|---|---|
| 3 | IL-15 | I | K | E | F | L | Q | S | F | V | H | I | V | Q | M | F | I | N | T | S | stop |
| 4 | IL-2 | I | V | E | F | L | N | R | W | I | T | F | C | Q | S | I | I | S | T | L | T | stop |
| 5 | IL-21 | P | K | E | F | L | E | R | F | K | S | L | L | Q | K | M | I | H | Q | H | L | S |
| 6 | IL-4 | L | E | N | F | L | E | R | L | K | T | I | M | R | E | K | Y | S | K | C | S |
| 7 | IL-9 | A | L | T | F | L | E | S | L | L | E | L | F | Q | K | E | K | M | R | G | M | R |
| 8 | IL-7 | D | L | C | F | L | K | R | L | L | - | - | Q | E | I | K | T | C | W | N | K | I | L |

Fig 1A

The consensus sequence for the γc- and the IL-2/IL-15-box.

| | | D/E | F | L | Polar E Q/N | Polar S/R | Non-polar | Non-polar I/K | | Aliphatic L/I | Non-polar | Q | Charged | | I/K | | | | SEQ ID NO: |
|---|---|---|---|---|---|---|---|---|---|---|---|---|---|---|---|---|---|---|---|
| γc-Box | | | | | | | | | | | | Q | Charged | | I/K | | | S | 9 |
| IL-2/IL-15 box | 1 | 2 | 3 | 4 | 5 | 6 | 7 | 8 | 9 | 10 | 11 | 12 | 13 | 14 | 15 | 16 | 17 | 18 | 19 | 10 |

FIG. 13B atgtacaggatgcaactcctcctgtccttgcactgtcttgcactcacaacagt   SEQ ID NO: 29
 M   Y   R   M   Q   L   L   S   C   I   A   L   S   L   A   L   V   T   N   S      SEQ ID NO: 30
gcacctactcaagtctacacagaaacacagtacactggcattactgctggat   SEQ ID NO: 29
 A   P   T   Q   S   T   K   T   Q   L   Q   L   E   H   L   L   L   D      SEQ ID NO: 30
ttacagatgattttgaatggaatattacaagatcccaaactcaccaggatgtc   SEQ ID NO: 29
 L   Q   M   I   L   N   G   I   N   N   Y   K   N   P   K   L   T   R   M   L      SEQ ID NO: 30
acaatttaagtttacatgcccaagagaaggccacagaactcatcagtgtctagaa   SEQ ID NO: 29
 T   F   K   F   Y   M   P   K   K   A   T   E   L   K   H   L   Q   C   L   E      SEQ ID NO: 30
gaagaactcaaacctctggaggaagttttgaatcttgctcaaagcaaaaacttcactta   SEQ ID NO: 29
 E   E   L   K   P   L   E   E   V   L   N   L   A   Q   S   K   N   F   H   L      SEQ ID NO: 30
aggaccagggactaatcagcaatatcaacgtaatatgctgaagagcaccattctgacaga   SEQ ID NO: 29
 R   P   R   D   L   I   S   N   I   N   V   I   V   L   E   L   K   G   S   E      SEQ ID NO: 30
acaacattcatgtgtgaatatgcagatgagacagcaaccatcgttgagttctgaacaga   SEQ ID NO: 29
 T   T   F   M   C   E   Y   A   D   E   T   A   T   I   V   E   F   L   N   R      SEQ ID NO: 30
tggattacctttgtcaagagcatcctcaactctgactga   SEQ ID NO: 29
 W   I   T   F   C   Q   S   I   I   S   T   L   T   -      SEQ ID NO: 30

FIG. 14

```
atgagaattcgaaaccacattgagaagtattccatgctactgctgttactt    SEQ ID NO: 31
 M   R   I   R   K   P   H   L   R   S   I   S   C   Y   L   L   L       SEQ ID NO: 32
ctaaacagtcattctctaactagaagctgcattcatgtcttcatttgggtgtgttcagt    SEQ ID NO: 31
 L   N   S   H   S   L   T   E   A   A   I   H   V   F   I   L   C   F   S   SEQ ID NO: 32
gcaggcttcctaaacagagccaactgggtgaatgtaatagtgattgaaaaaatt        SEQ ID NO: 31
 A   G   L   P   K   T   E   A   N   W   V   N   V   I   S   D   L   K   K   I   SEQ ID NO: 32
gaagtcttattccatcagtcattgaattatgctacttctctcttggagtgatgttcact    SEQ ID NO: 31
 E   D   L   Q   S   M   H   D   A   F   L   Y   T   S   S   D   V   H       SEQ ID NO: 32
cccagttgcaaagtaacgcaatgaagtgttctcttggagttacaagttattcaactaac    SEQ ID NO: 31
 P   S   C   K   V   T   A   M   K   C   F   L   L   Q   V   I   S   L       SEQ ID NO: 32
gagtccggagatgcaagtattcatgatacagtagaaatctgatcatccagcaacaac    SEQ ID NO: 31
 E   S   G   D   A   S   I   H   D   T   V   E   N   L   I   L   A   N   N   SEQ ID NO: 32
agtttgtctaatgggaatgtaacagaatgcaagcaagaatgtgaggaactggag        SEQ ID NO: 31
 S   L   S   N   G   N   V   T   S   C   K   E   C   E   E   L           SEQ ID NO: 32
gaaaaaataaagaattttgagttttgggttccaaatgtacatattgtcatcaac        SEQ ID NO: 31
 E   K   N   I   K   E   F   L   Q   S   F   V   H   I   V   Q   M   F   I   N   SEQ ID NO: 32
acttcttga                                                     SEQ ID NO: 31
 T   S   -                                                     SEQ ID NO: 32
```

```
atggataaccaaggagtaatctactcagaccctgcccccaagggcag   SEQ ID NO: 35
 M  D  N  Q  G  V  I  Y  S  D  L  N  L  P  P  K  R  Q   SEQ ID NO: 36
caacgaaaacctaaaggcaataaagctccatttagcaactgacaagtaacctat   SEQ ID NO: 35
 Q  R  K  P  K  G  N  K  S  H  L  A  T  D  Q  I  T  Y   SEQ ID NO: 36
gcgattaaccttcaaatgaaaggctctcaaggatctgggaacaaacctatcac   SEQ ID NO: 35
 A  I  N  L  Q  M  K  A  G  D  F  Q  G  N  D  K  T  Y  H   SEQ ID NO: 36
tgcaagattaccatccagctcccaagctctgtgggatcctgggaatcatctgt   SEQ ID NO: 35
 C  K  D  L  P  S  A  P  K  L  I  V  G  I  L  G  I  C   SEQ ID NO: 36
cttatcttaatggcctctgtgttaacgatagtattccctcacgtcatgtggcat   SEQ ID NO: 35
 L  I  L  M  A  G  V  V  T  Y  I  V  I  P  R  H  C  H   SEQ ID NO: 36
tgtccggagagagagttgctgcctactcgaagactccagtctgcttctctagat   SEQ ID NO: 35
 C  P  E  W  I  T  Y  S  M  S  C  Y  I  C  K  E  R  R   SEQ ID NO: 36
agcttggggagaatgaattcctgattccaccatcctcatgattggtgtgttt   SEQ ID NO: 35
 T  W  E  E  M  K  F  L  G  I  I  P  S  S  W  I  G  V  F   SEQ ID NO: 36
aatgaagagatcagcatgcatccaggtgacaatgaatggttttcaactatgagata   SEQ ID NO: 35
 N  E  E  N  S  H  P  V  T  N  C  L  A  F  K  N  E  I   SEQ ID NO: 36
cgtaacagcagtcatccatcaatgctgaactaactgtcagtgctacaagcataatca   SEQ ID NO: 35
 R  N  S  S  H  P  V  T  N  C  L  A  V  L  Q  V  N  R  L  K  S   SEQ ID NO: 36
aaggactcagatcctcaatatatcatcatgaagatgaagcataagctttag   SEQ ID NO: 35
 K  D  N  A  E  L  N  C  A  V  L  H  C  K  H  K  L  -   SEQ ID NO: 36
gccagtgtggatcctcaataatatcatcatgtaagcataagctttag   SEQ ID NO: 35
 A  Q  C  G  S  I  I  Y  H  C  K  H  K  L  -   SEQ ID NO: 36
```

FIG. 17 atgaataacaagaggaacttctcagaagtgagtctggcccaaggaccaagcggcag SEQ ID NO: 37
M N K R G T F S E V S L A Q D P K R Q SEQ ID NO: 38 caaggaaaactaaggcaataagcttccattcaaggaccaagcagaatattccaa SEQ ID NO: 37
Q R K P K Q * K S S I S R E Q E I F Q SEQ ID NO: 38 gtagaattcaatcttcaaatcctcctgatcatcaaggtgataaaatatgatgac SEQ ID NO: 37
V E L N L Q N P L M H Q G I D K I Y D SEQ ID NO: 38 tgccaaggtttactgccactgcaagctccgagtcggagtcctaggaatcattgc SEQ ID NO: 37
C Q G L L P P E K L T A E V L G I I C SEQ ID NO: 38 attgtcctgatggccactgtgttaaacatagtccttcctttcctgaacagaac SEQ ID NO: 37
I V M A T V M K T I V L P F L E Q N SEQ ID NO: 38 aatttcccgaattcgcaagacgtcattgtggcattcggcatgcacggaac SEQ ID NO: 37
N F S P N T R Q K A R H C G H C P E E SEQ ID NO: 38 tggatacaccactacaacagtatgatgtaaggaaagactgggaagag SEQ ID NO: 37
W I T Y N S C Y T C K E R R W E E SEQ ID NO: 38 agtttgctggctgactacttaccttcctcatggattggttcgtacagcagt SEQ ID NO: 37
S L A C * N G L I D N E E SEQ ID NO: 38 atgaattctgtggccagcatttggtttggccttcaacataaagactcagat SEQ ID NO: 37
M N F L A S I L P S W I Q V F R N S D SEQ ID NO: 38 catatcgaacttaactgtgacaatgcagtgctacacaagatgaagctaatcagccagtgga SEQ ID NO: 37
H P V N L A F K H K I K S A Q C SEQ ID NO: 38 aatgctgaactaactcattgtgcagttcaagtaagcatcagcatttag SEQ ID NO: 37
N A E L H C A V L Q V N R L K S SEQ ID NO: 38 tcttccaatgatatcatcattgtaagcatcagcttag SEQ ID NO: 37
S S M I Y H C M K L - SEQ ID NO: 38

```
atgaatcaacaaggaacctcactcctggagtctggtctgcaggagtctcagaccaggtctctgactcctggctactgagtcagtctactactctgtctgacctggaaaccactagcag  SEQ ID NO: 43
 M  N  Q  Q  G  T  S  L  L  E  S  G  L  Q  E  S  L  A  Q  D  P  K  R  Q                                                    SEQ ID NO: 44 caagaattaaggccaataaatcttccattccaagaactcaggaataattccaa ... Q R L K G N K I S I S C T K Q E I F Q                              SEQ ID NO: 43/44 gtaaatctaaacctcaatgcatcatcatcatcatcatgcatgatgcatgatgcatgcatcgac ... V E N L O N A S D E Q G N D K T Y H                    SEQ ID NO: 43/44 tgccagcttcctgatggccacactgcccactctgaggtcactagtgaggtcactaggctcattgc ... C K G L P P E K L T A E V L Q I C                    SEQ ID NO: 43/44 attgtcctgatgccattccctccgattcaacatagtctagtattgcattgatgtcctgatatg ... I V L M A T V L K T I V L I P C I G V L                 SEQ ID NO: 43/44 gagcagaaccctggatcaactcagtgtttcctcatgaagcacgatcatactcatggaggaagaagaact ... E Q N P G L N R M K Q K A R H C Q H C            SEQ ID NO: 43/44 cctgagtggatttacaataggccctgcagttccatcaacgagtatcgaagttgaggaagaagact ... P E W I Y N G V V Y I C K E R R T                    SEQ ID NO: 43/44 tgggaagaagagtgctggccgctctgaagacctgcttctatag ... W E E R V C W P V L R R T I C F L *                                          SEQ ID NO: 43/44
```

MODULATING THE EFFECTS OF GAMMA-C-CYTOKINE SIGNALING FOR THE TREATMENT OF ALOPECIA AND ALOPECIA ASSOCIATED DISORDERS

CROSS REFERENCE TO RELATED APPLICATIONS

This application claims the benefit of priority to U.S. Provisional Patent Application No. 62/842,846, filed May 3, 2019. The foregoing application is fully incorporated herein by reference for all purposes.

SEQUENCE LISTING IN ELECTRONIC FORMAT

The present application is being filed along with a Sequence Listing as an ASCII text file via EFS-Web. The Sequence Listing is provided as a file entitled BION012ASEQLIST.txt, created and last saved on Apr. 29, 2020, which is 47,415 bytes in size. The information in the electronic format of the Sequence Listing is incorporated herein by reference in its entirety in accordance with 35 U.S.C. § 1.52(e).

BACKGROUND

Field

The present embodiments relate to inhibiting, ameliorating, reducing a severity of, treating, delaying the onset of, or preventing autoimmune diseases such as alopecia, and alopecia associated disorders using one or more therapeutic compounds by modulating the signaling by at least one γc-cytokine family member.

Description of the Related Art

Cytokines are a diverse group of soluble factors that mediate various cell functions, such as, growth, functional differentiation, and promotion or prevention of programmed cell death (apoptotic cell death). Cytokines, unlike hormones, are not produced by specialized glandular tissues, but can be produced by a wide variety of cell types, such as epithelial, stromal or immune cells.

The γc-family cytokines are a group of mammalian cytokines that are mainly produced by epithelial, stromal and immune cells and control the normal and pathological activation of a diverse array of lymphocytes. These cytokines are critically required for the early development of T cells in the thymus as well as their homeostasis in the periphery.

SUMMARY

In some embodiments, a composition comprises a therapeutic compound in an amount sufficient to modulate signaling by at least one γc-cytokine family member, thereby inhibiting, ameliorating, reducing a severity of, treating, delaying the onset of, or preventing at least one alopecia related disorder, and a pharmaceutically acceptable carrier.

In some embodiments of the composition, the at least one alopecia related disorder is selected from the group consisting of alopecia, pemphigus, pemphigoid, psoriasis, vitiligo, graft-versus-host disease, and immune-mediated hair loss.

In some embodiments of the composition, the at least one γc-cytokine family member is selected from the group consisting of IL-2, IL-4, IL-7, IL-9, IL-15 and IL-21.

In some embodiments of the composition, the therapeutic compound is at least one of a γc cytokine antagonist peptide, a γc cytokine antagonist peptide derivative, anti-CD8 antibody, anti-IL-2 antibody, anti-IL-15 antibody, anti-NKG2A antibody, or a combination thereof.

In some embodiments of the composition, the γc cytokine antagonist peptide comprises a partial sequence of a γc-box D-helix region of each of at least two γc-cytokine family members.

In some embodiments of the composition, the partial sequence comprises consecutive blocks of at least 5 amino acids of the γc-box D-helix region of each of at least two γc-cytokine family members.

In some embodiments of the composition, the partial sequence comprises consecutive blocks of 1-10 amino acids of the γc-box D-helix region of each of at least two γc-cytokine family members.

In some embodiments of the composition, the γc-box D-helix region of each of at least two γc-cytokine family members is selected from the group consisting of IL-15, IL-2, IL-21, IL-4, IL-9, and IL-7.

In some embodiments of the composition, the γc cytokine antagonist peptide comprises 11 to 50 amino acids.

In some embodiments of the composition, the γc cytokine antagonist peptide further comprises a conjugate at the N-termini, C-termini, side residues, or a combination thereof.

In some embodiments of the composition, the conjugate comprises one or more additional moieties selected from the group consisting of bovine serum albumin (BSA), albumin, Keyhole Limpet Hemocyanin (KLH), Fc region of IgG, a biological protein that functions as scaffold, an antibody against a cell-specific antigen, a receptor, a ligand, a metal ion, and Poly Ethylene Glycol (PEG).

In some embodiments of the composition, the γc cytokine antagonist peptide further comprises a signal peptide.

In some embodiments of the composition, the γc cytokine antagonist peptide comprises the amino acid sequence D/E-F-L-E/Q/N-S/R-X-I/K-X-L/I-X-Q (SEQ ID NO: 2), wherein X denotes any amino acid.

In some embodiments of the composition, the γc cytokine antagonist peptide derivative shares at least about 50% identity with a peptide of SEQ ID NO: 2.

In some embodiments of the composition, the γc cytokine antagonist peptide derivative shares at least about 90% identity with a peptide of SEQ ID NO: 2.

In some embodiments of the composition, the γc cytokine antagonist peptide derivative shares at least about 95% identity with a peptide of SEQ ID NO: 2.

In some embodiments of the composition, the γc cytokine antagonist peptide comprises a sequence of SEQ ID NO: 1 (BNZ-γ)

In some embodiments of the composition, the γc cytokine antagonist peptide and the γc antagonist peptide derivative have similar physico-chemical properties but distinct biological activities.

In some embodiments of the composition, the γc cytokine antagonist peptide derivative shares at least about 50% identity with a peptide of SEQ ID NO: 1.

In some embodiments of the composition, the γc cytokine antagonist peptide derivative shares at least about 90% identity with a peptide of SEQ ID NO: 1.

In some embodiments of the composition, the γc cytokine antagonist peptide derivative shares at least about 95% identity with a peptide of SEQ ID NO: 1.

In some embodiments of the composition, the pharmaceutically acceptable carrier is formulated for topical, oral, and/or parenteral delivery.

In some embodiments of the composition, the pharmaceutically acceptable carrier is formulated for topical delivery.

In some embodiments of the composition, the pharmaceutically acceptable carrier is formulated for oral delivery.

In some embodiments of the composition, the pharmaceutically acceptable carrier is formulated for parenteral delivery.

In some embodiments, a method of inhibiting, ameliorating, reducing a severity of, treating, delaying the onset of, or preventing at least one alopecia related disorder comprises administering one or more of the compositions provided herein to a subject in need thereof, thereby inhibiting, ameliorating, reducing a severity of, treating, delaying the onset of, or preventing the at least one alopecia related disorder.

In some embodiments of the method of inhibiting, ameliorating, reducing a severity of, treating, delaying the onset of, or preventing at least one alopecia related disorder, the at least one alopecia related disorder is selected from the group consisting of alopecia, pemphigus, pemphigoid, psoriasis, vitiligo, graft-versus-host disease, and immune-mediated hair loss.

In some embodiments, a method of designing a γc-cytokine antagonist peptide and/or a derivative thereof configured to modulate and/or block signaling by at least one γc-cytokine family member that inhibits, ameliorates, reduces a severity of, treats, delays the onset of, or prevents at least one alopecia related disorder comprises the steps of using a computer to obtain from an amino acid sequence database amino acid sequences of at least one a γc-cytokine family member, assembling a γc cytokine antagonist peptide and/or a derivative thereof based on a sequence of the at least one γc-cytokine family member, wherein the γc cytokine antagonist peptide and/or the derivative thereof modulates and/or blocks signaling by the at least one γc-cytokine family member.

In some embodiments of the method of designing a γc-cytokine antagonist peptide and/or a derivative thereof, the at least one γc-cytokine family member is selected from the group consisting of IL-2, IL-4, IL-7, IL-9, IL-15 and IL-21.

In some embodiments of the method of designing a γc-cytokine antagonist peptide and/or a derivative thereof, the γc cytokine antagonist peptide comprises a partial sequence of a γc-box D-helix region of each of at least two γc-cytokine family members.

In some embodiments of the method of designing a γc-cytokine antagonist peptide and/or a derivative thereof, the sequence comprises consecutive blocks of at least 5 amino acids of the γc-box D-helix region of each of at least two γc-cytokine family members.

In some embodiments of the method of designing a γc-cytokine antagonist peptide and/or a derivative thereof, the sequence comprises consecutive blocks of 1-10 amino acids of the γc-box D-helix region of each of at least two γc-cytokine family members.

In some embodiments of the method of designing a γc-cytokine antagonist peptide and/or a derivative thereof, the γc-box D-helix region of each of at least two γc-cytokine family members is selected from the group consisting of IL-15, IL-2, IL-21, IL-4, IL-9, and IL-7

In some embodiments of the method of designing a γc-cytokine antagonist peptide and/or a derivative thereof, the γc cytokine antagonist peptide comprises 11 to 50 amino acids.

In some embodiments of the method of designing a γc-cytokine antagonist peptide and/or a derivative thereof, the γc cytokine antagonist peptide further comprises a conjugate at the N-termini, C-termini, side residues, or a combination thereof.

In some embodiments of the method of designing a γc-cytokine antagonist peptide and/or a derivative thereof, the γc cytokine antagonist peptide further comprises a signal peptide.

In some embodiments of the method of designing a γc-cytokine antagonist peptide and/or a derivative thereof, the γc cytokine antagonist peptide comprises the amino acid sequence D/E-F-L-E/Q/N-S/R-X-I/K-X-L/I-X-Q (SEQ ID NO: 2), wherein X denotes any amino acid.

In some embodiments of the method of designing a γc-cytokine antagonist peptide and/or a derivative thereof, the γc cytokine antagonist peptide derivative shares at least about 50% identity with a peptide of SEQ ID NO: 2.

In some embodiments of the method of designing a γc-cytokine antagonist peptide and/or a derivative thereof, the γc cytokine antagonist peptide derivative shares at least about 90% identity with a peptide of SEQ ID NO: 2.

In some embodiments of the method of designing a γc-cytokine antagonist peptide and/or a derivative thereof, the γc cytokine antagonist peptide derivative shares at least about 95% identity with a peptide of SEQ ID NO: 2.

In some embodiments of the method of designing a γc-cytokine antagonist peptide and/or a derivative thereof, the γc cytokine antagonist peptide comprises a sequence of SEQ ID NO: 1 (BNZ-γ)

In some embodiments of the method of designing a γc-cytokine antagonist peptide and/or a derivative thereof, the γc cytokine antagonist peptide derivative shares at least about 50% identity with a peptide of SEQ ID NO: 1.

In some embodiments of the method of designing a γc-cytokine antagonist peptide and/or a derivative thereof, the γc cytokine antagonist peptide derivative shares at least about 90% identity with a peptide of SEQ ID NO: 1.

In some embodiments of the method of designing a γc-cytokine antagonist peptide and/or a derivative thereof, the γc cytokine antagonist peptide derivative shares at least about 95% identity with a peptide of SEQ ID NO: 1.

In some embodiments of the method of designing a γc-cytokine antagonist peptide and/or a derivative thereof, the γc cytokine antagonist peptide and the derivative thereof have similar physico-chemical properties but distinct biological activities.

In some embodiments, a kit for inhibiting, ameliorating, reducing a severity of, treating, delaying the onset of, or preventing at least one alopecia related disorder comprises one or more of the compositions provided herein.

In some embodiments of the kit, the at least one alopecia related disorder is selected from the group consisting of alopecia, pemphigus, pemphigoid, psoriasis, vitiligo, graft-versus-host disease, and immune-mediated hair loss.

BRIEF DESCRIPTION OF THE DRAWINGS

FIG. 1A shows an alignment of the D-helix region of human γc-cytokine family members.

FIG. 1B depicts the γc-box (SEQ ID NO: 9) and IL-2/IL-15 box (SEQ ID NO: 10) motifs which give rise to the consensus sequence around the D-helix region of the γc-cytokines.

Figure 10A:
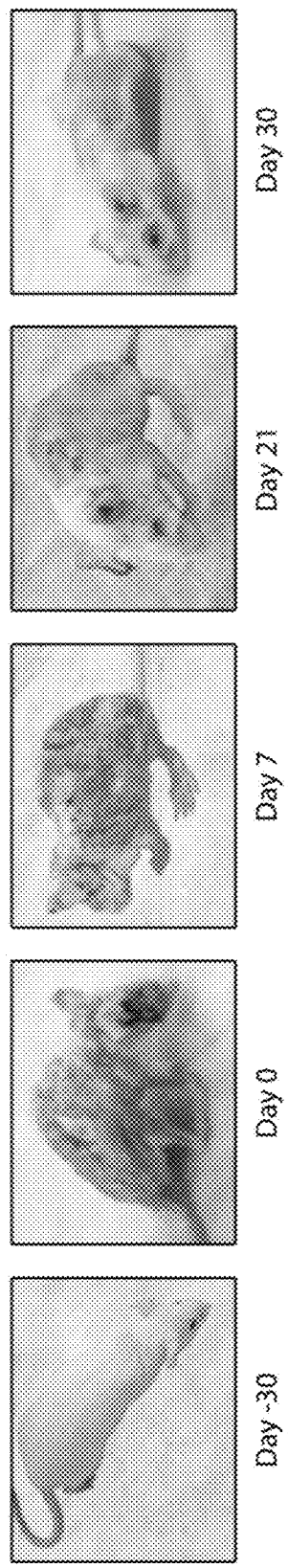

FIG. 10A shows the reversal of immune-mediated hair loss by BNZ-γ in a representative NSG mouse. Time points: Day −30 is prior to huPBMC transplantation. Day 0 is 4-weeks post-huPBMC transplantation. Day 7 is 5-weeks post-huPBMC transplantation and 1 week into a twice weekly BNZ-γ dosing regimen for a treatment duration of two weeks. Day 21 is 7-weeks post-huPBMC transplantation and 1 week following completion of a twice weekly BNZ-γ dosing regimen for a treatment duration of two weeks. Day 30 is just over 8-weeks post-huPBMC transplantation and just over 2 weeks following completion of a twice weekly BNZ-γ dosing regimen for a treatment duration of two weeks.

Figure 10B:
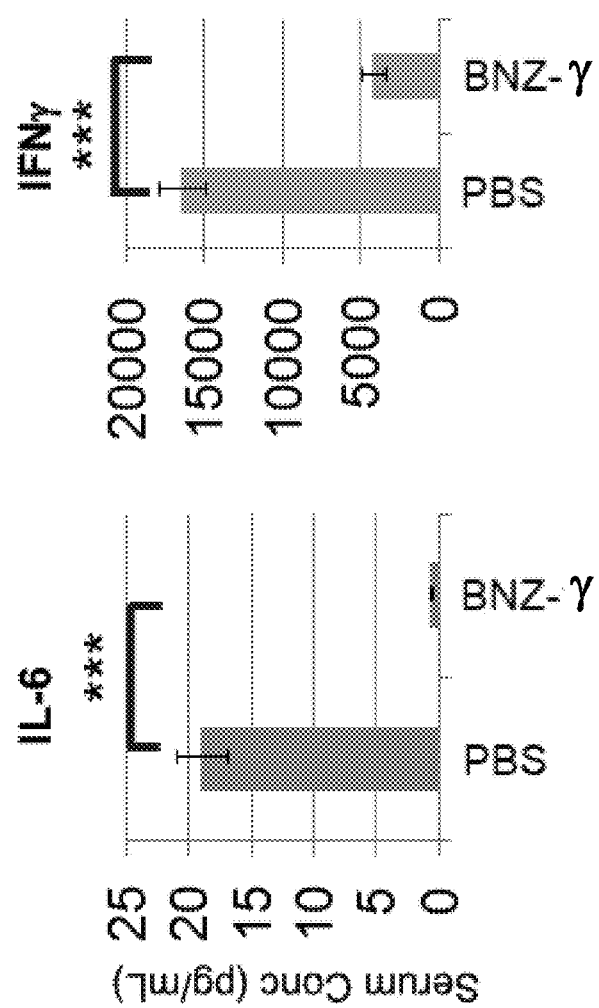

FIG. 10B shows a comparison of serum concentrations of the of circulating human inflammatory cytokines IL-6 and IFNγ in two representative NSG mice 6-weeks post-huPBMC transplantation with and without (PBS control) completion of a twice weekly BNZ-γ dosing regimen for a treatment duration of two weeks. The results were statistically significant (***) $p<0.001$.

Figure 11A:
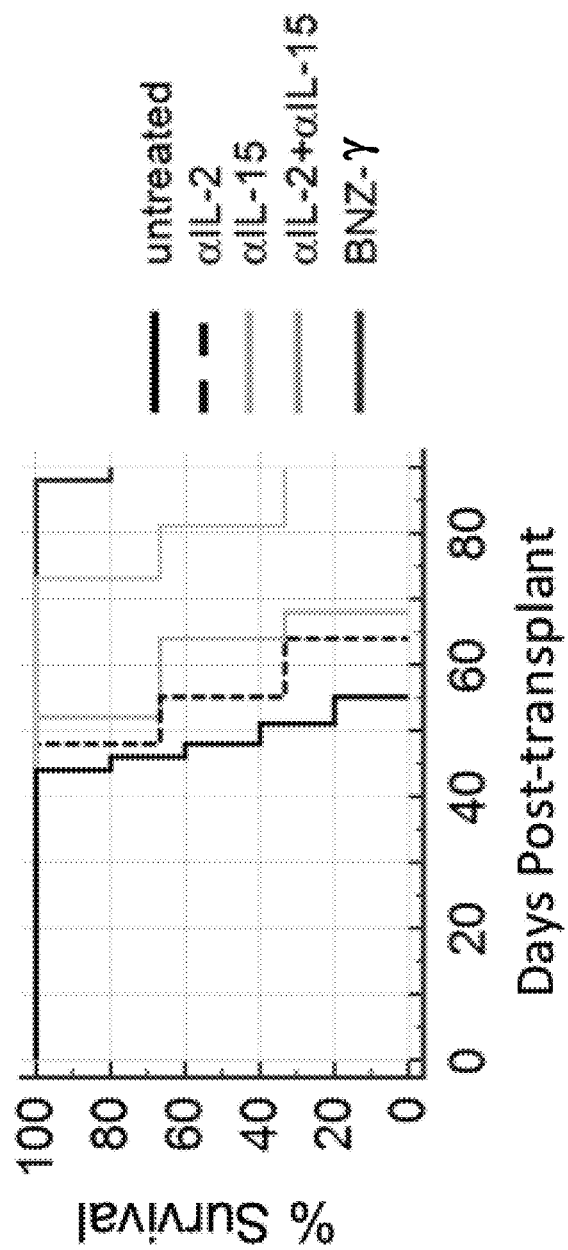

FIG. 11A shows survival curves of humanized NSG mice that began therapeutic treatment 35-days post-huPBMC transplantation with PBS control (untreated), anti-IL-2 antibody, anti-IL-15 antibody, combination anti-IL-2 and anti-IL-15 antibody, and BNZ-γ.

Figure 11B:
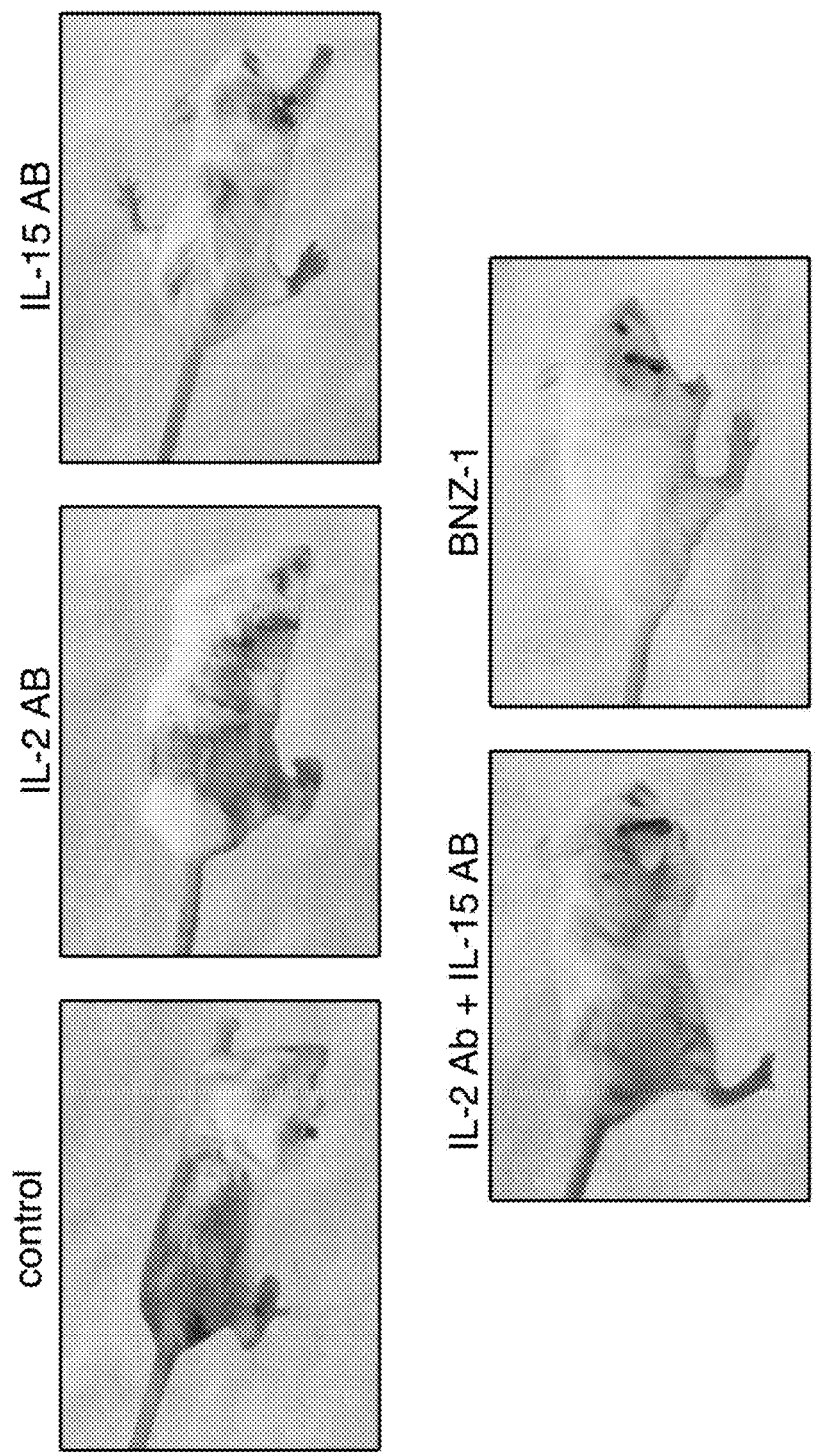

FIG. 11B shows a comparison of the level of hair regrowth in a representative NSG mouse from each of the treatment groups: PBS control, anti-IL-2 antibody (AB), anti-IL-15 AB, combination anti-IL-2 and anti-IL-15 AB, and BNZ-γ following the completion of a four-week treatment regimen on NSG mice at 35-days post-huPBMC transplantation.

Figure 11C:
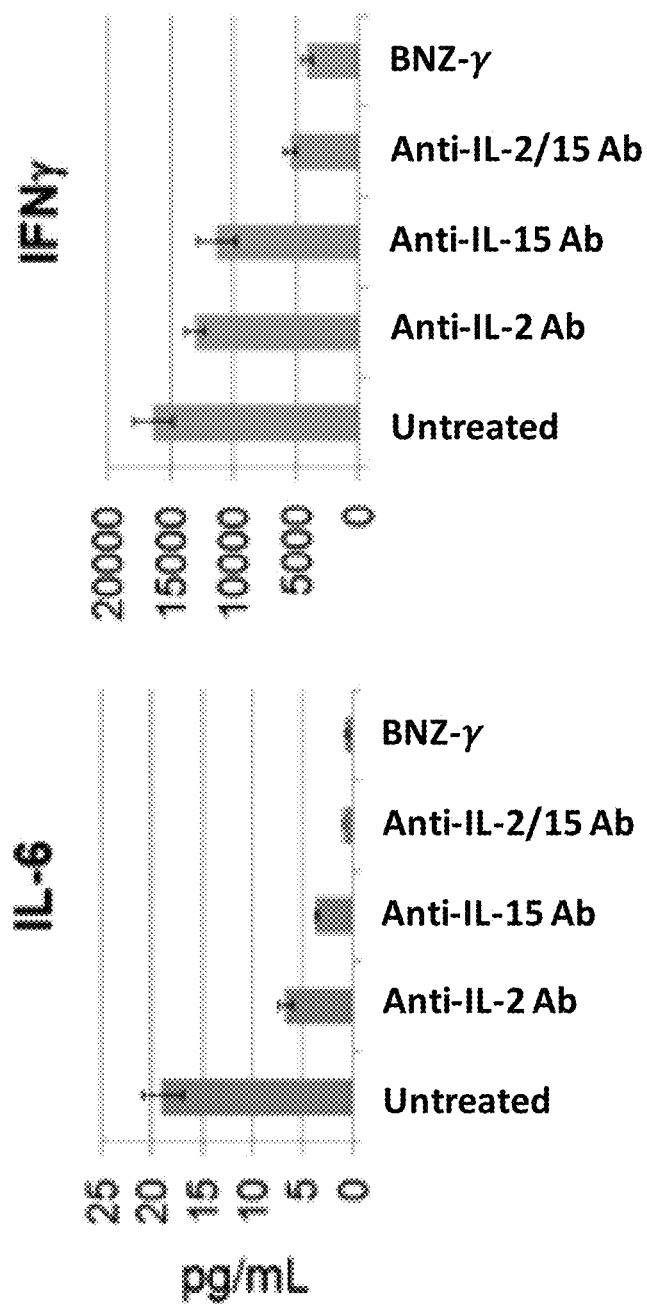

FIG. 11C shows a comparison of average serum concentrations of the of circulating human inflammatory cytokines IL-6 and IFNγ from each of the treatment groups: PBS control, anti-IL-2 antibody (Ab), anti-IL-15 Ab, combination anti-IL-2 and anti-IL-15 Ab, and BNZ-γ following the completion of a four-week treatment regimen on NSG mice at 35-days post-huPBMC transplantation.

Figure 12:
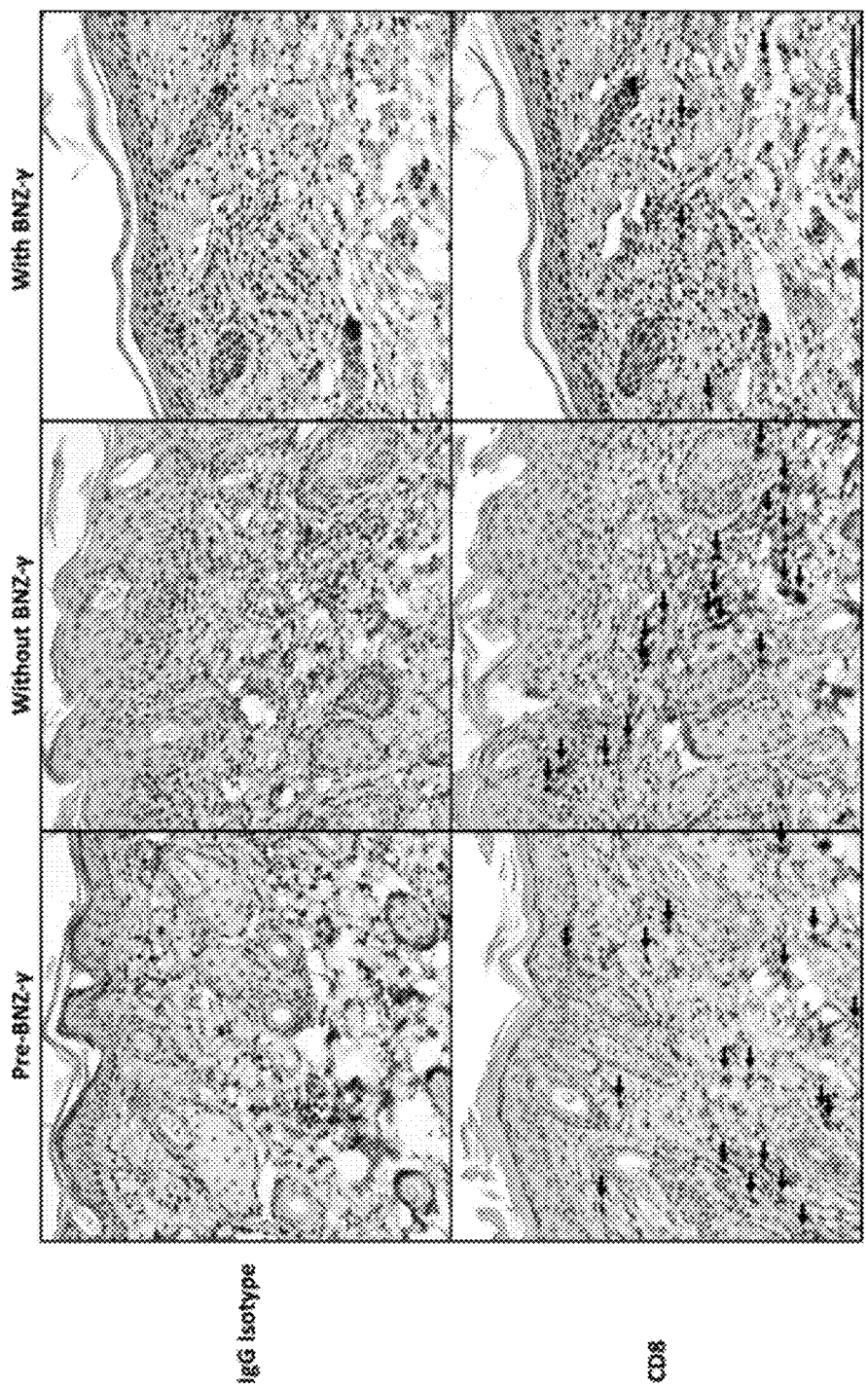

FIG. 12 shows immuno-stained skin tissue for human CD8+ T-cells from humanized NSG mice 3-weeks (pre-BNZ-γ) and 7-weeks (with or without BNZ-γ treatment) post-huPBMC transplantation. Human CD8+ T-cells highlighted with black arrow.

Figure 13A:
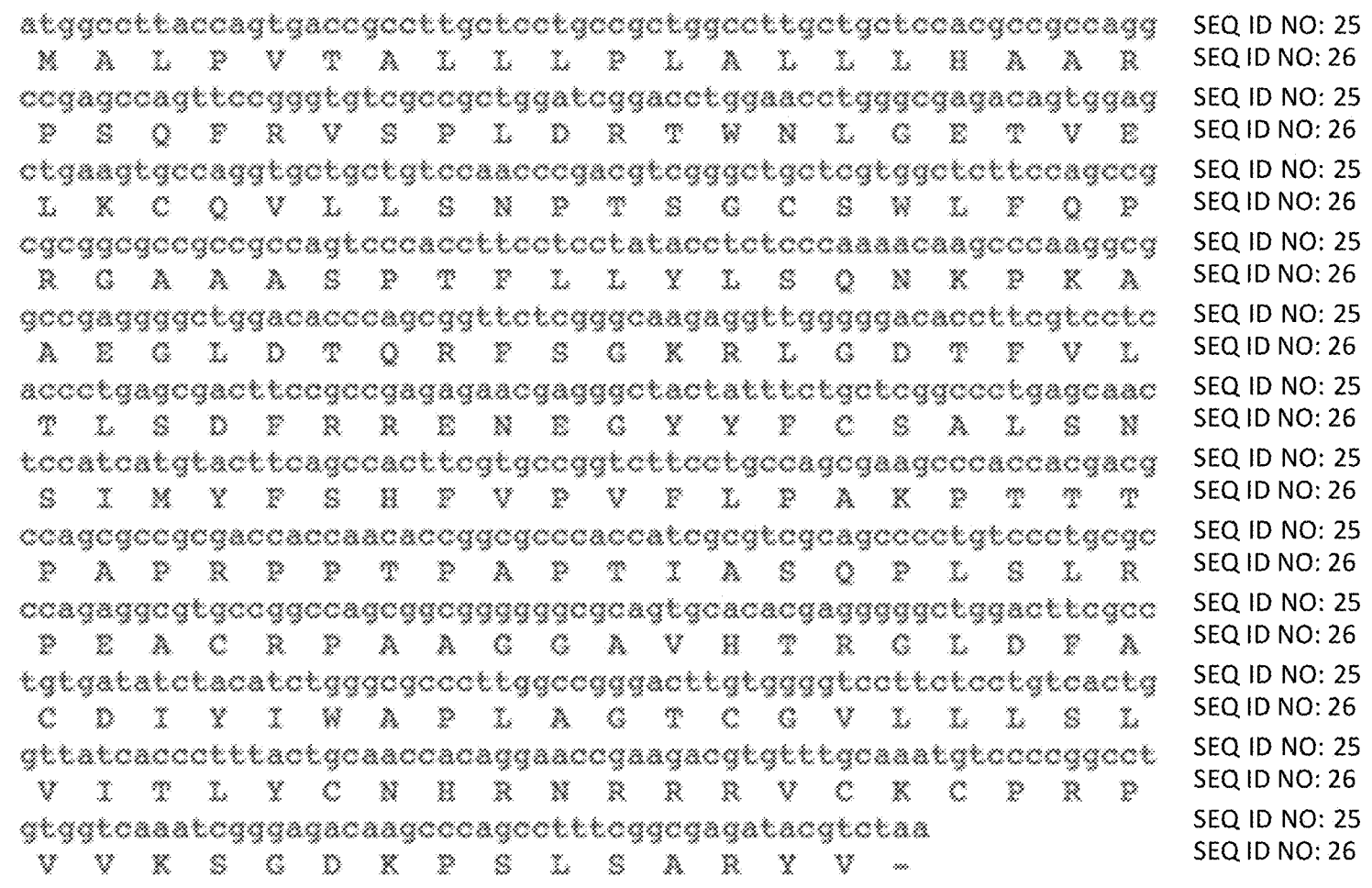

FIG. 13A depicts the nucleotide and peptide sequence of human CD8 alpha chain.

Figure 13B:
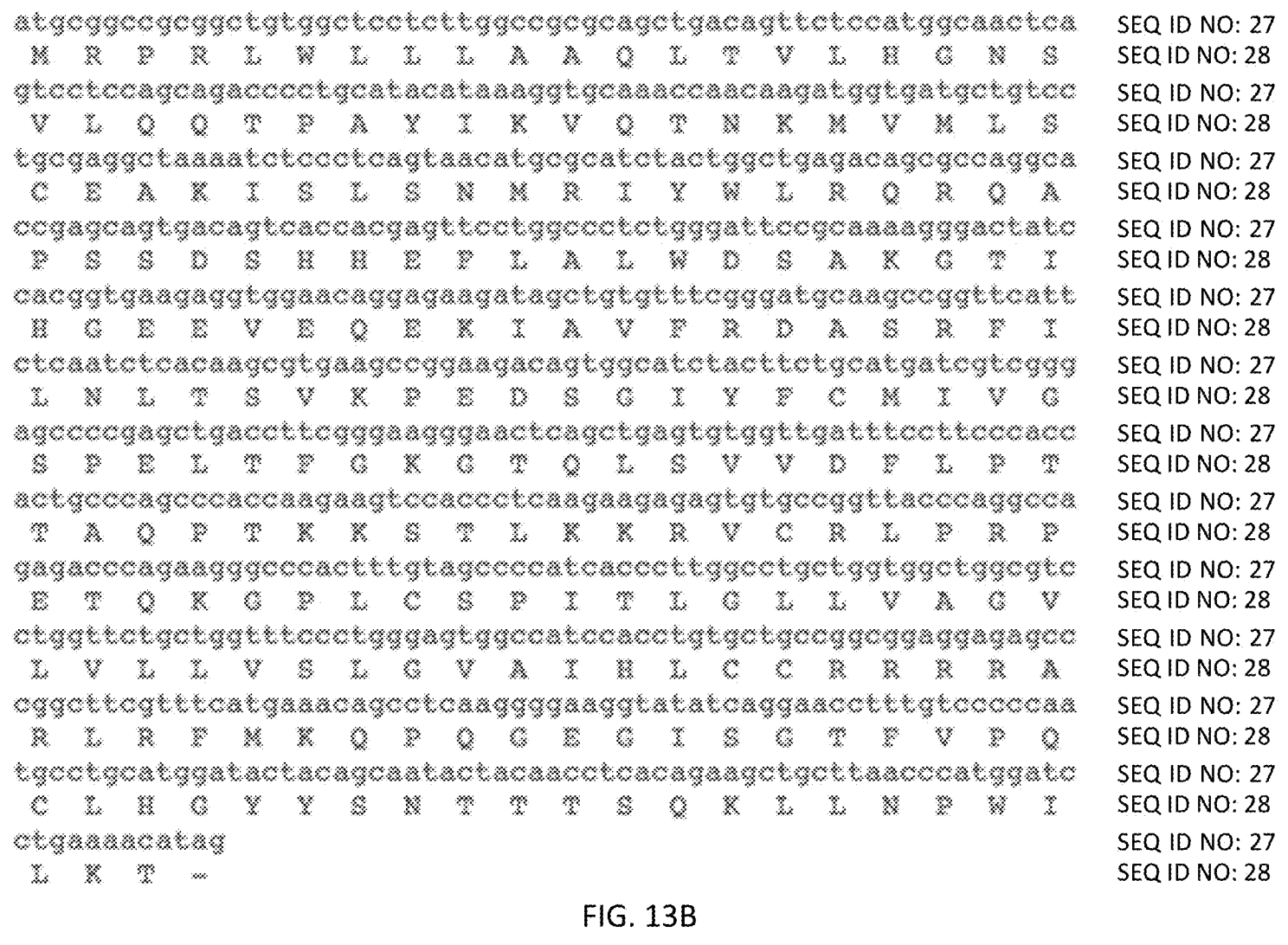

FIG. 13B depicts the nucleotide and peptide sequence of human CD8 beta chain.

FIG. 14 depicts the nucleotide and peptide sequence of human IL-2.

FIG. 15 depicts the nucleotide and peptide sequence of human IL-15.

Figure 16:
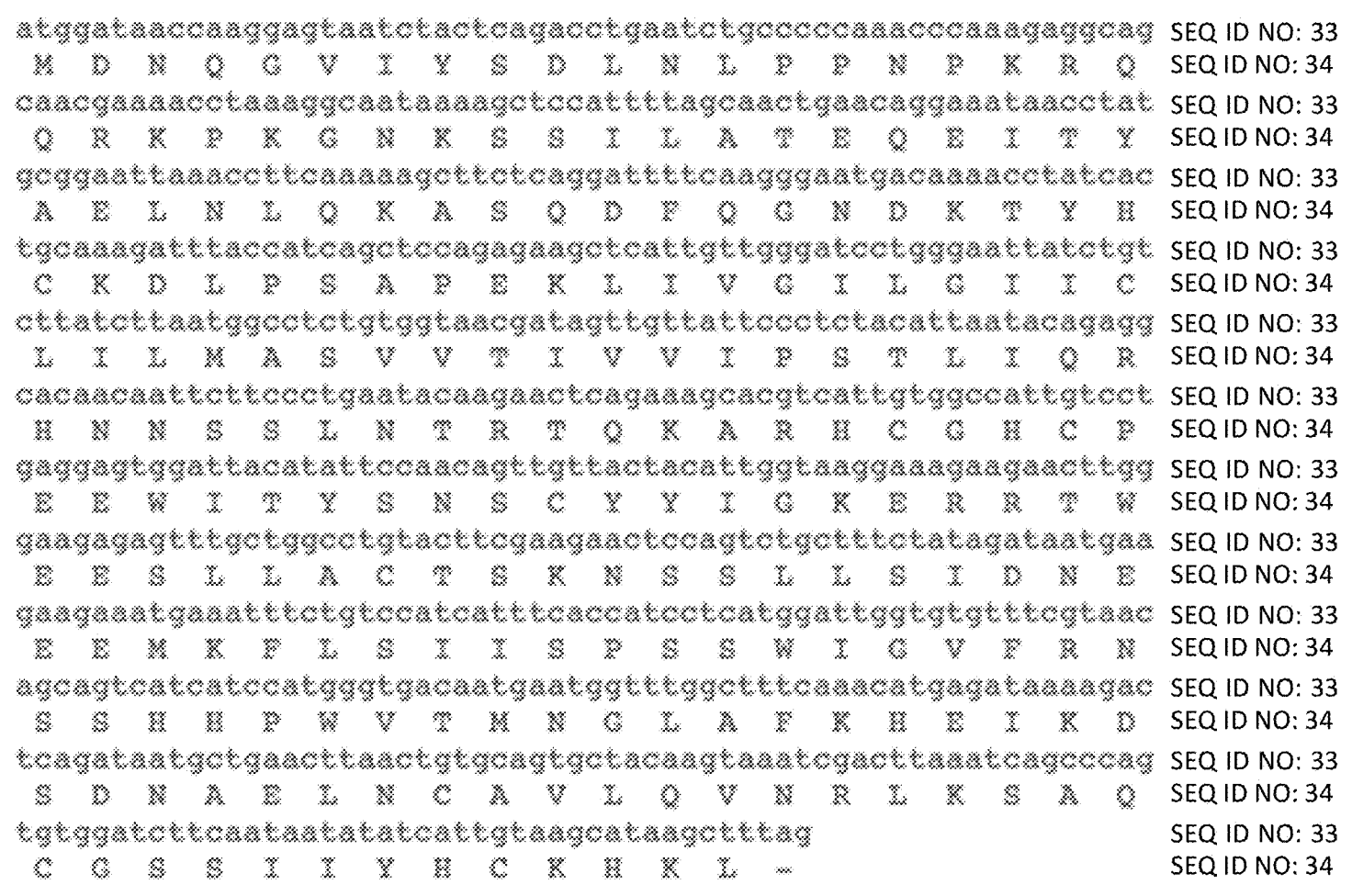

FIG. 16 depicts the nucleotide and peptide sequence of human NKG2A.

FIG. 17 depicts the nucleotide and peptide sequence of human NKG2B.

FIG. 18 depicts the nucleotide and peptide sequence of human NKG2C.

Figure 19:
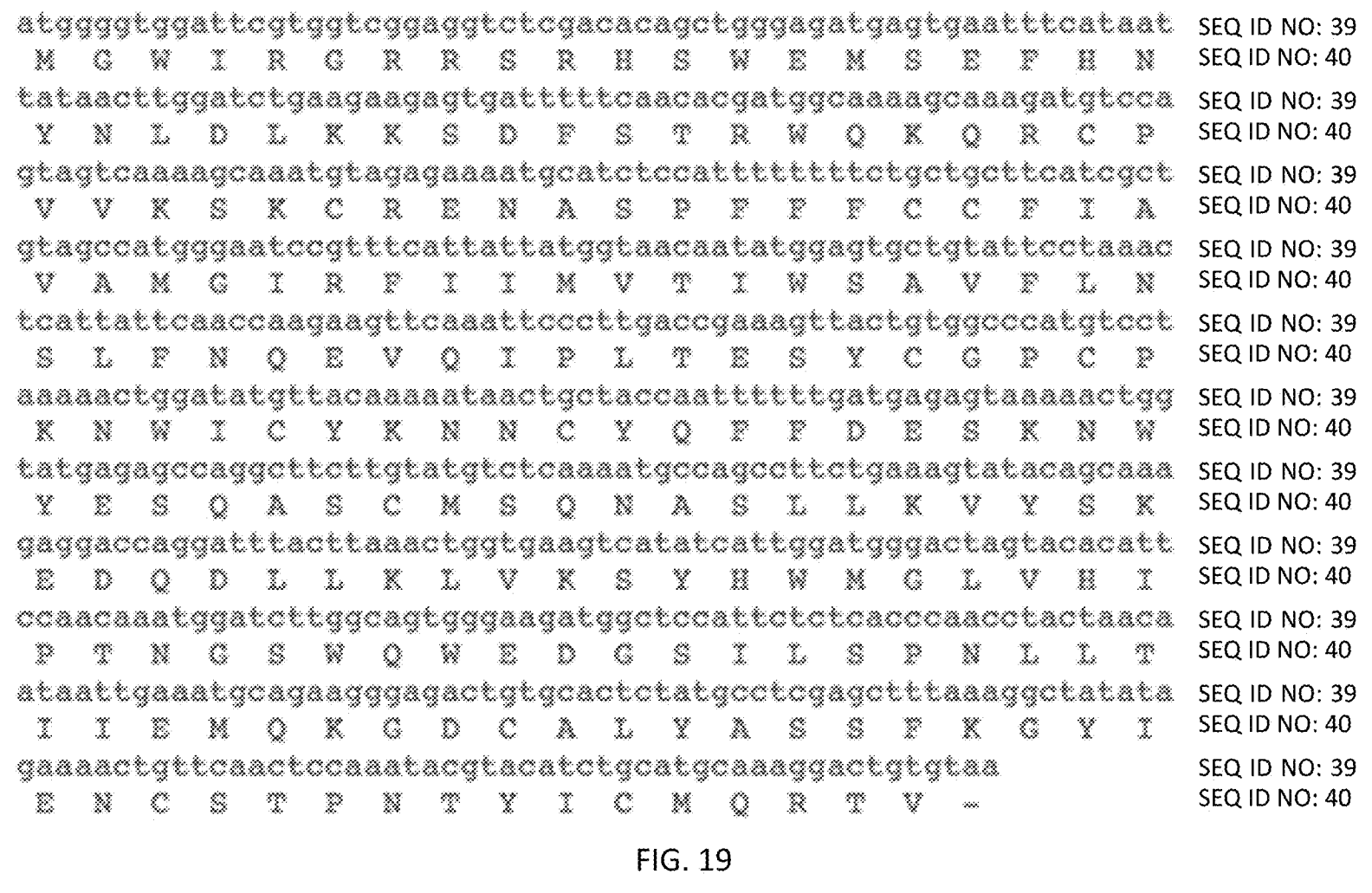

FIG. 19 depicts the nucleotide and peptide sequence of human NKG2D.

Figure 20:
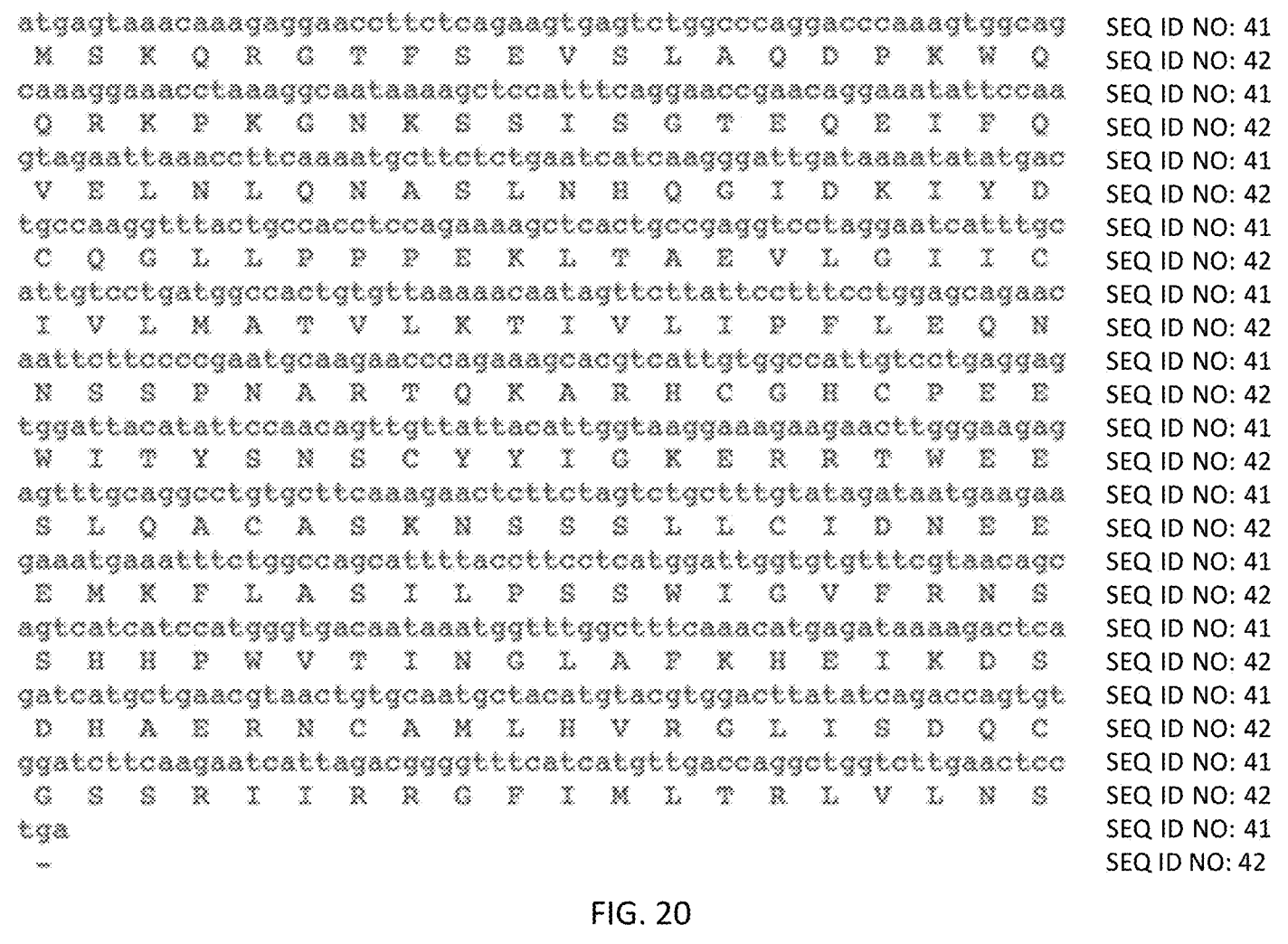

FIG. 20 depicts the nucleotide and peptide sequence of human NKG2E.

FIG. 21 depicts the nucleotide and peptide sequence of human NKG2F.

Figure 22:
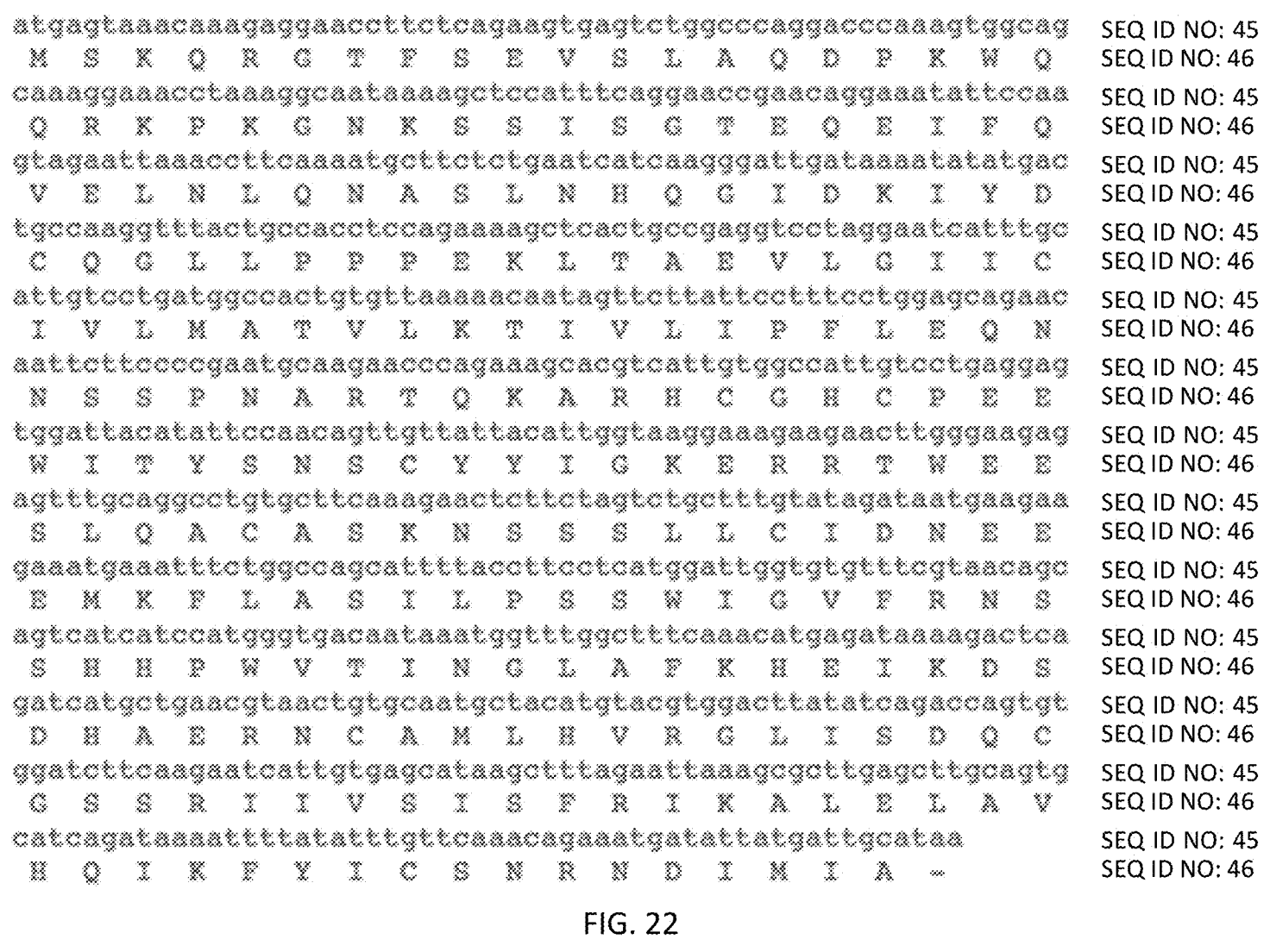

FIG. 22 depicts the nucleotide and peptide sequence of human NKG2H.

DETAILED DESCRIPTION

Embodiments herein relate to compositions, methods, and kits comprising one or more therapeutic compounds that modulate signaling by at least one γc-cytokine family member for inhibiting, ameliorating, reducing a severity of, treating, delaying the onset of, or preventing autoimmune diseases such as alopecia, and alopecia associated disorders. Cytokines of the γc-family comprise a group of mammalian cytokines that are mainly produced by epithelial, stromal and immune cells and control the normal and pathological activation of a diverse array of lymphocytes. Description of target diseases, as well as methods of administration, production, and commercialization of the therapeutic compounds are disclosed.

Overview

More than 100 cytokines have been identified so far and are considered to have developed by means of gene duplications from a pool of primordial genes (See Bazan, J. F. 1990, Immunol. Today 11:350-354). In support of this view, it is common for a group of cytokines to share a component in their multi-subunit receptor system. The most well-documented shared cytokine subunit in T cells is the common γ subunit (γc-subunit).

The γc-subunit is shared by 6 known cytokines (Interleukin-2 (IL-2), Interleukin-4 (IL-4), Interleukin-7 (IL-7), Interleukin-9 (IL-9), Interleukin-15 (IL-15), and Interleukin-21 (IL-21), collectively called the "γc-cytokines" or "γc-family cytokines" and plays an indispensable role in transducing cell activation signals for all these cytokines. Additionally, for each of the γc-cytokines, there are one or two private cytokine-specific receptor subunits that when complexed with the γc-subunit, give rise to a fully functional receptor. (See Rochman et al., 2009, Nat Rev Immunol. 9: 480-90.)

The γc-family cytokines are a group of mammalian cytokines that are mainly produced by epithelial, stromal and immune cells and control the normal and pathological activation of a diverse array of lymphocytes. These cytokines are critically required for the early development of T cells in the thymus as well as their homeostasis in the periphery. For example, in the absence of the γc-subunit, T, B and NK cells do not develop in mice. (See Sugamura et al., 1996, Annu. Rev. Immunol. 14:179-205).

The γc-cytokines are important players in the development of the lymphoid cells that constitute the immune system, particularly T, B, and NK cells. Further, γc-cytokines have been implicated in various human diseases. Thus, factors that inhibit γc-cytokine activity would provide useful tools to elucidate the developmental mechanism of subsets of lymphocytes and to treat immune disorders and γc-cytokine-mediated diseases.

Germ line depletion of the genes encoding the γc-subunit in mice or mutations of γc-subunit in humans are known to cause severe combined immunodeficiency (SCID) by disrupting the normal appearance or function of NK, T, and B cells. The importance of the γc-subunit in the signal transduction of the γc-cytokines, IL-2, -4, -7, -9, 15, -21, is indicated in studies demonstrating the lack of response of lymphocytes from these mice and human patients to the γc-cytokines (reviewed in Sugamura et al., 1995 Adv. Immunol. 59:225-277). This indicates that disruption of the interaction between the γc-subunit and a γc-cytokine would efficiently block the intracellular signaling events by the γc-cytokine family members. Therefore, antagonist peptides according to the present embodiments are expected to effectively block the pathogenic changes in humans suffering from the diseases mediated by misregulation of the γc-cytokine family members.

Applicants present novel compositions, methods, and kits comprising one or more therapeutic compounds that modulate signaling by at least one γc-cytokine family member for inhibiting, ameliorating, reducing a severity of, treating, delaying the onset of, or preventing autoimmune diseases such as alopecia, and alopecia associated disorders. Applicants have also devised novel, low molecular weight therapeutic compounds herein referred to as "Simul-Block", which suppress the activity of multiple γc-cytokines. These low molecular weight therapeutic compounds, which include both chemicals and peptides, are often less immunogenic than antibodies, and can be used as a stand-alone approach, or complementary to antibody-mediated approaches, for modulating γc-cytokine activity in clinical interventions.

Pathologies Associated with the γc-Cytokines

Recent studies have indicated that dysregulation of expression and dysfunction of the γc-cytokines could lead to a wide variety of human immunologic and hematopoietic diseases.

IL-2

While IL-2 was historically considered a prototype T cell growth factor, the generation of a knockout mouse lacking IL-2 expression revealed that IL-2 is not critical for the growth or developmental of conventional T cells in vivo. Over-expression of IL-2, however, leads to a preferential expansion of a subset of T-cells; the regulatory T cells (T-regs). (See Antony et al., 2006, J. Immunol. 176:5255-66.) T-regs suppress the immune responses of other cells and thus act to maintain peripheral tolerance (reviewed in Sakaguchi et al., 2008, Cell 133:775-87). Breakdown of peripheral tolerance is thought to cause autoimmune diseases in humans.

Thus, the immunosuppressive function of T-regs is thought to prevent the development of autoimmune diseases (See Sakaguchi et al., 2008, Cell 133:775-87). T-regs have also been implicated in cancer, where solid tumors and hematologic malignancies have been associated with elevated numbers of T-regs (See De Rezende et al., 2010, Arch. Immunol. Ther. Exp. 58:179-190).

IL-4

IL-4 is a non-redundant cytokine involved in the differentiation of T helper cells into the Th2 (T-helper type 2) subset, which promotes the differentiation of premature B cells into IgE producing plasma cells. IgE levels are elevated in allergic asthma. Thus, IL-4 is implicated in the development of allergic Asthma. Antibodies targeting IL-4 can be used to treat or even prevent the onset of allergic asthma. (See Le Buanec et al., 2007, Vaccine 25:7206-16.)

IL-7

IL-7 is essential for B cell development and the early development of T cells in the thymus. In mice, the abnormal expression of IL-7 causes T-cell-associated leukemia. (See Fisher et al., 1993, Leukemia 2:S66-68.) However, in humans, misregulation of IL-7 does not appear to cause T-cell-associated leukemia. In humans, up-regulation of IL-7 either alone or in combination with another γc-cytokine family member, IL-15, has been implicated in Large Granular Lymphocyte (LGL) leukemia.

IL-9

The role of IL-9 is still rather uncharacterized compared to other γc-cytokine family members. Mice depleted of the IL-9 gene appear normal and do not lack any subsets of cells in the lymphoid and hematopoietic compartments. Recent studies, however, reveal an in vivo role for IL-9 in the generation of Th17 (T-helper induced by interleukin-17) cells (See Littman et al., 2010, Cell 140(6):845-58; and Nowak et al., 2009, J. Exp. Med. 206: 1653-60).

IL-15

IL-15 is critically involved in the development of NK cells, NK-T cells, some subsets of intraepithelial lymphocytes (IELs), γδ-T cells, and memory-phenotype CD8 T-cells (See Waldmann, 2007, J. Clin. Immunol. 27:1-18; and Tagaya et al., 1996, EMBO J. 15:4928-39.) Over-expression of IL-15 in mice leads to the development of NK-T cell and CD8 cell type T cell leukemia (See Fehniger et al., 2001, J. Exp. Med. 193:219-31; Sato et al. 2011 Blood in press). These experimentally induced leukemias appear similar to LGL (large-granular lymphocyte) leukemia in humans, since in both instances the leukemic cells express CD8 antigen.

It is also suspected that IL-15-mediated autocrine mechanisms may be involved in the leukemic transformation of CD4 T lymphocytes. (See Azimi et al., 1998, Proc. Natl. Acad. Sci. 95:2452-7; Azimi et al., 1999, J. Immunol. 163:4064-72; Azimi et al., 2000, AIDS Res. Hum. Retroviruses 16:1717-22; and Azimi et al., 2001, Proc. Natl. Acad. Sci. 98:14559-64). For example, CD4-tropic HTLV-I, which causes Adult T cell leukemia in humans, induces autocrine growth of virus-transformed T cells through the production of IL-15 and IL-15Rα (Azimi et al., 1998, Proc. Natl. Acad. Sci. 95:2452-7).

In addition to leukemic transformation, recent studies implicate IL-15 in the pathological development of Celiac disease (CD), an autoimmune disease. IL-15 is known to stimulate the differentiation of NK, CD8 and intestinal intraepithelial lymphocyte (IEL) cells into lymphokine-activated killer (LAK) cells by inducing the expression of cytolytic enzymes (i.e., Granzyme and Perforin) as well as interferon-γ. Celiac Disease (denoted CD from herein) is an immune-mediated enteropathy that is triggered by the consumption of gluten-containing food in individuals that express specific HLA-DQ alleles.

The prevalence of this disease is 1% in the western population. The only current treatment for CD is the complete elimination of gluten from the patient's diet. The pathology of CD is mainly caused by extensive damage to the intestinal mucosa, which is caused by activated CD8 T cells that have infiltrated to the intestinal lamina propria. These CD8 T cells appear to be activated through mechanisms involving IL-15. One recent publication demonstrated in mice that ectopic over-expression of IL-15 by enterocytes leads to the development of enteropathy, which closely resembles the lesions in CD patients. Neutralization of IL-15 activity dramatically diminished the pathological changes. Thus, an intervention blocking the activation of CD8 T cells by IL-15 appears to provide an alternative strategy in managing CD to the conventional gluten-free diet.

IL-21

IL-21 is the most recently discovered member of the γc-family. Unlike other family members, IL-21 does not appear to have potent growth-promoting effects. Instead, IL-21 is thought to function more as a differentiation factor than a factor controlling cellular proliferation (See Tagaya, 2010, J. Leuk. Biol. 87:13-15).

Current Strategies for Treating γc-Cytokine-Mediated Disorders

Because the γc-cytokines are thought to be involved in numerous human diseases, several methods of treating γc-cytokine-implicated diseases by inhibiting γc-cytokine family activities have been proposed. These methods include the use of cytokine-specific monoclonal antibodies to neutralize the targeted cytokine's activity in vivo; use of monoclonal antibodies targeting the private cytokine-specific receptor subunits (subunits other than the shared γc-subunit) to selectively inhibit cytokine activity; and use of chemical inhibitors that block the downstream intracellular cytokine signal transduction pathway.

While cytokine-specific antibodies are often the first choice in designing therapeutics, cytokines that share receptor components display overlapping functions (See Paul, W. E., 1989, Cell 57:521-24) and more than one cytokine can co-operate to cause a disease (See Examples described herein). Thus, antibody approaches involving neutralization of a single cytokine may not always be optimal in the treatment of cytokine-implicated human diseases. Alternative therapeutic strategies may involve the use of more than one antibody, where each target a specific cytokine implicated in disease pathogenesis, and/or targeting a specific protein receptor implicated in disease pathogenesis whose activity and/or abundance is directly modulated by γc-cytokine signaling.

Strategies for designing therapeutics that inhibit the function of multiple cytokines via antibodies which recognize a shared receptor component have also been proposed. However, the multi-subunit nature of cytokine receptor systems and the fact that functional receptors for a single cytokine can assume different configurations makes this approach difficult.

For example, a functional IL-15 receptor can be either IL-15Rβ/γc or IL-15Rα/β/γc. (See Dubois et al., 2002, Immunity 17:537-47.) An antibody against the IL-15Rβ receptor (TMβ1), is an efficient inhibitor of the IL-15 function, but only when the IL-15Rα molecule is absent from the receptor complex. (See Tanaka et al., 1991, J. Immunol. 147:2222-28.) Thus, the effectiveness of a monoclonal anti-receptor antibody, whether raised against a shared or a private subunit, can be context-dependent and is unpredictable in vivo.

The polypeptides of the therapeutic compounds, their fragments or other derivatives, or analogs thereof, or cells expressing them can be used as an immunogen to produce antibodies thereto. The term "immunogen" or "epitope", as used herein, refers to portions of a polypeptide having antigenic or immunogenic activity in an animal, preferably a mammal. In a preferred embodiment, the therapeutic compounds of the present invention encompass a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. The term "antigenic epitope," as used herein, is defined as a portion of a protein to which an antibody can immune-specifically bind its antigen as determined by any method well known in the art, for example, by immunoassays (Cox et al. 2004 "Immunoassay methods", in Assay Guidance Manual [internet]). Immuno-specific binding excludes non-specific binding but does not necessarily exclude cross-reactivity with other antigens. Antigenic epitopes need not necessarily be immunogenic. Either the full-length polypeptide or an antigenic peptide fragment of the therapeutic compounds in the present disclosure can be used.

Epitope-bearing polypeptide regions of the therapeutic compounds in the present disclosure can be determined by any method known in the art, for example, by multiple software programs freely available for use, including but not limited to: BepiPred-2.0 (Jespersen et al. 2017 Nucleic Acids Res, 45:W24-W29), SVMTriP (Yao et al. 2012 PLoS One, 7:e45152), and ABCpred (Saha et al. 2006 Proteins, 65:40-8). Antibodies are preferably prepared from these regions or from discrete fragments in these regions. However, antibodies can be prepared from any region of the peptide as described herein. Antibodies may also be developed against specific functional sites, such as the site of ligand binding or sites that are glycosylated, phosphorylated, myristoylated, or amidated. Peptide fragments which function as epitopes may be produced by any conventional means, such as biological production using recombinant technology or chemically through manual or automated peptide synthesis technologies.

Various procedures known in the art may be used for the production of such antibodies and fragments. Epitope-bearing polypeptides of the present invention may be used to induce antibodies according to methods well known in the art including, but not limited to, in vivo immunization, in vitro immunization (Tomimatsu et al. 2014 Methods Mol Biol, 1060:297-307), and phage display methods (Hammers et al. 2014 J Invest Dermatol., 134:e17). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Antibodies generated against the polypeptides corresponding to each of the therapeutic compounds of the present invention can be obtained by direct injection of the polypeptides into an animal or by administering the polypeptides to an animal, preferably a nonhuman. Animals such as rabbits, rats, mice, and goats can be immunized with either free or carrier-coupled peptides, or artificially branched forms known as multiple antigenic peptides (MAPs), for instance, by intraperitoneal and/or intradermal injection of emulsions containing about 100 ug of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

For preparation of monoclonal antibodies, any technique which provides antibodies produced by continuous cell line cultures can be used. Examples include the hybridoma technique (Kohler et al. 1975 Nature, 256:495-7), the trioma technique, the human B-cell hybridoma technique (Kozbor et al. 1983 Immunology Today, 4:72-9), and the EBV-hybridoma technique to produce human monoclonal antibodies (Kozbor et al. 1982 Proc Natl Acad Sci, 79:6651-55). Techniques described for the production of single chain antibody fragments (scFv) (Blažek et al. 2003 Folia Microbiol, 48:687-98) can be adapted to produce single chain antibodies to immunogenic polypeptides derived from the therapeutic compounds in the present invention.

Humanized antibodies are antibody molecules derived from a non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (Riechmann et al. 1988 Nature 332:323-7). Antibodies can be humanized using a variety of techniques known in the art including, for example, CDR-grafting (Williams et al. 2010 "Humanising Antibodies by CDR Grafting", in Antibody Engineering), veneering or resurfacing (Padlan 1991 Mol Immunol 28:489-98; Studnicka et al. 1994 Protein Eng 7:805-14; Roguska et al. 1994 Proc Natl Acad Sci 91:969-73), and chain shuffling (Guo-Qiang et al. 2009 Methods Mol Biol 562:133-42).

Completely human antibodies are particularly desirable for therapeutic treatment of human patients. Human antibodies can be made by a variety of methods known in the art including phage display using antibody libraries derived from human immunoglobulin sequences (Frenzel, et al. 2017 Transfus Med Hemother 44:312-18, Vaughan, et al. 1996 Nature 14:309-14). Human antibodies which recognize a selected epitope can also be generated using a technique referred to as "guided selection." In this approach, a selected non-human monoclonal antibody, e.g., a mouse antibody, is used to guide the selection of a completely human antibody recognizing the same epitope. (Jespers et al. 1994 Biotechnology 12:899-903).

Also, transgenic mice may be used to express human antibodies to immunogenic polypeptides derived from the therapeutic compounds in the present invention (Laffleur et al. 2012 Methods Mol Biol, 901:149-59). Transgenic mice, which are incapable of expressing functional endogenous immunoglobulins, can be used to express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide corresponding to a therapeutic compound of the present invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. 1995 Int Rev Immunol. 13:65-93.

Antibodies of the present invention include, but are not limited to, polyclonal, monoclonal, multi-specific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immune-specifically binds an antigen. The immunoglobulin molecules of the invention can be of any type (e.g., IgG, IgE, IgM, Ig|D, IgA and IgY), class (e.g., IgG1, IgG2, IgG3, IgG4, IgA1 and IgA2) or subclass of immunoglobulin molecule. In a preferred embodiment, the immunoglobulin is an IgG1 isotype. In another preferred embodiment, the immunoglobulin is an IgG2 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Targeting JAK3, as an Existing Alternative Example for the Inhibition of Multiple γc-Cytokines The interaction between the γc-subunit and a γc-cytokine leads to the activation of an intracellular protein tyrosine kinase called Janus kinase 3 (Jak3). Jak3, in turn, phosphorylates multiple signaling molecules including STAT5, and PI3 kinase. The interaction of the γc-subunit and Jak3 is very specific. In fact, there is no other receptor molecule that recruits Jak3 for signal transduction. (See O'Shea, 2004, Ann. Rheum. Dis. 63:(suppl. II):ii67-7.) Thus, the inhibition of cytokine signaling through the γc-subunit can be accomplished by blocking the activity of Jak3 kinase. Accordingly, multiple small molecule chemical inhibitors that target the kinase activity of Jak3 have been introduced to the market. (See Pesu et al., 2008, Immunol. Rev. 223:132-142.) One such example is CP690,550.

The major shortcoming of these protein kinase inhibitors is the lack of specificity to Jak3 kinase. These drugs intercept the binding of ATP (adenosine-triphosphate) molecules to Jak3 kinase, a common biochemical reaction for many protein kinases, and thus tend to block the action of multiple intracellular protein kinases that are unrelated to Jak3 kinase whose actions are critically needed for the well-being of normal cells in various tissues. Thus, more specific inhibitors of signaling through the γc-subunit are needed.

There is therefore a great need for an alternative non-small molecule chemical strategy for treating γc-cytokine-implicated diseases.

Discovery of the γc-Box

The C-terminus (the D-helix) of the γc-cytokines contains the proposed site for interacting with the common γc-subunit of the multi-unit cytokine receptors. (Bernard et al., 2004 J. Biol. Chem. 279:24313-21.) Comparison of the biochemical properties of the amino acids of all γc-cytokines identified in mice and humans revealed that the chemical nature of the amino acids, for example, hydrophobicity, hydrophilicity, base/acidic nature, are conserved, if not identical, at many positions in the D-helix across the members of the γc-cytokine family.

In contrast, the sequence of IL-13, which is related to the γc-cytokine, IL-4, but does not bind to the γc-subunit, does not exhibit significant homology in the D-helix region to the γc-cytokines, suggesting that the sequence homology in the D-helix region is correlated with binding to the γc-subunit. As shown in FIG. 1A, alignment of the amino acid sequences of the D-helix region of γc-cytokine family members in humans reveals a motif of moderate sequence homology in these cytokines referred to herein as "the γc-box".

The γc-box (SEQ ID NO: 9) comprises 19 amino acids where out of the 19 positions, positions 4, 5, and 13 are fully conserved as Phenylalanine, Leucine, and Glutamine, respectively. Less conservation is observed at positions 6, 7 and 11 of the γc-box where the amino acid is one of two or three related amino acids that share physico-chemical properties: position 6 may be occupied by the polar amino acids Glutamate, Asparagine or Glutamine; non-polar amino acids Serine or Arginine can occupy position 7; and position 11 is occupied by either of the non-polar aliphatic amino acids Leucine or Isoleucine. Positions 9 and 16 may be occupied by the either the non-polar amino acid Isoleucine or the polar amino acid Lysine. See FIG. 1B. Some differences in the amino acid composition of the γc-box are observed at positions 9 and 16 amongst subfamilies of the γc-cytokines. Comparison of the γc-cytokines across species indicates that Isoleucine is often present at the 9 and 16 positions in the IL-2/15 subfamily, whereas the other γc-family members often possess Lysine in these positions. Not wishing to be bound by a particular theory, Isoleucine and Lysine are biochemically different and thus may impart specific conformational differences between the IL-2/15 subfamily and other γc-cytokines.

Conservation of the γc-box motif between γc-cytokines is supported by findings that a Glutamine (Gln, Q) residue located in the D-helix region is critical for the binding of the γc-cytokines to the γc-subunit. (Bernard et al., 2004 J. Biol. Chem. 279: 24313-21.)

Modulators of γc-Cytokine Activity

The activity of γc-family cytokines may be blocked by disrupting the interaction between the γc-cytokine and the γc-subunit, for example by introducing a competitive inhibitor which can interact with the γc-subunit without stimulating signaling through the multi-subunit cytokine receptors. Not to be bound by a particular theory, the conserved γc-box motif, which participates in binding of the γc-family cytokines to the γc-subunit, presents a core base amino acid sequence which can be utilized to design peptide modulators of γc-cytokine signaling.

Figure 2:
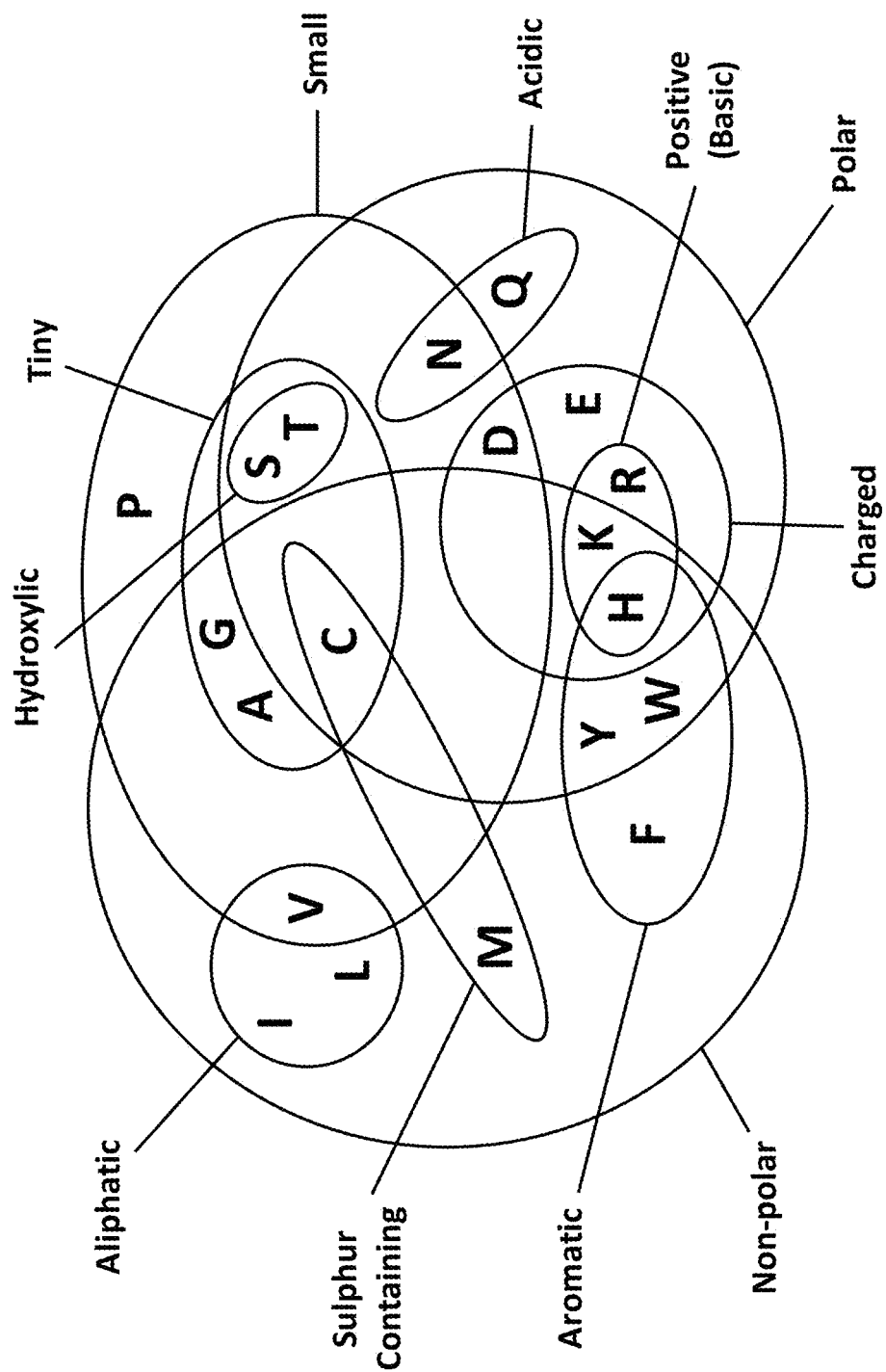
FIG. 2 depicts a diagramed representation of the biochemical properties of amino acids.

The core γc-box amino acid sequence comprises: D/E-F-L-E/Q/N-S/R-X-I/K-X-L/I-X-Q (SEQ ID NO: 2) (where X denotes any amino acid). Embodiments described herein relate to custom peptide derivatives of the core γc-box amino acid sequence which can modulate the activity of one or more γc-cytokines. Custom peptide derivatives include any peptide whose partial amino acid sequence shows approximately 50%, 50-60%, 60-70%, 70-80%, 80%, 90%, 95%, 97%, 98%, 99% or 99.8% identity to the core γc-box amino acid sequence. Custom peptide derivatives further include any peptide wherein a partial amino acid sequence of that peptide derivative comprises amino acids with similar physico-chemical properties to the amino acids of the core γc-box. For example, amino acids with similar physico-chemical properties would include Phenylalanine, Tyrosine, Tryptophan, and Histidine, which are aromatic amino acids. FIG. 2 shows a diagrammed representation of amino acids with similar physico-chemical properties which may be may be substituted for the amino acids comprising the core γc-box. Peptide derivatives of the core γc-box may be 11, 12, 13, 14, 15, 16, 17, 18, 19, 20, 21, 22, 23, 24, 25-30, 30-35, 35-40, 40-45, 45-50, or more than 50 amino acids in length. In some embodiments, the custom peptide derivatives may be conjugated to the N-termini, C-termini and/or to the side residues of existing biological proteins/peptides.

Based on the identification of the conserved γc-box motif in cytokines which bind to the γc-subunit, Applicants have devised a novel, 19-mer custom derivative peptide which is an artificial composite peptide combining the amino acid sequence of the human IL-2 and IL-15 γc-box. The 19-mer peptide, herein referred to as BNZ-γ, consists of the amino acid sequence: I-K-E-F-L-Q-R-F-I-H-I-V-Q-S-I-I-N-T-S (SEQ ID NO: 1), where the amino acids depicted by bold characters are conserved between IL-2 and IL-15 and the underlined amino acids represent positions where the physico-chemical properties of the amino acids are conserved.

Applicants discovered that the 19-mer BNZ-γ, suppresses IL-15 and IL-9 induced cellular proliferation, but not IL-3 or IL-4 induced cellular proliferation. See FIG. 3A and EXAMPLE 2. Applicants further demonstrated that BNZ-γ inhibits IL-15 mediated phosphorylation of the intracellular cytokine signal transduction molecule, STAT-5. See FIG. 4 and EXAMPLE 5. These results demonstrate that custom peptide derivatives of the conserved γc-box motif can modulate the activity of multiple γc-cytokines.

Several embodiments relate to one or more therapeutic compounds that modulate signaling by at least one γc-cytokine family member for inhibiting, ameliorating, reducing a severity of, treating, delaying the onset of, or preventing autoimmune diseases such as alopecia, and alopecia associated disorders. In some embodiments, the therapeutic compound is one or more of a γc-cytokine antagonist peptide, a γc-cytokine antagonist peptide derivative, anti-CD8 antibody, anti-IL-2 antibody, anti-IL-15 antibody, anti-NKG2A antibody, or a combination thereof.

In some embodiments, γc-cytokine antagonist peptides and derivatives thereof, which are also referred to herein as custom derivative peptides or composite peptide derivatives of the 19-mer BNZ-γ amino acid sequence, I-K-E-F-L-Q-R-F-I-H-I-V-Q-S-I-I-N-T-S (SEQ ID NO: 1), can inhibit the activity of one or more γc-cytokines. Custom peptide derivatives of the 19-mer BNZ-γ amino acid sequence include any peptide whose partial amino acid sequence shows approximately 50%, 50-60%, 60-70%, 70-80%, 80%, 90%, 95%, 97%, 98%, 99% or 99.8% identity to amino acid sequence: I-K-E-F-L-Q-R-F-I-H-I-V-Q-S-I-I-N-T-S (SEQ ID NO: 1). Custom peptide derivatives further include any peptide wherein a partial amino acid sequence of that peptide derivative comprises amino acids with similar physico-chemical properties to the amino acids of sequence: I-K-E-F-L-Q-R-F-I-H-I-V-Q-S-I-I-N-T-S (SEQ ID NO: 1).

In several embodiments, the amino acid residues of the custom derivative peptides retain similar physico-chemical properties with the amino acid residues of BNZ-γ, but exhibit different biological inhibition specificity to the 6 γc-cytokine family members from that of the original 19-mer peptide. Peptide derivatives of BNZ-γ may be 19, 20, 21, 22, 23, 24, 25-30, 30-35, 35-40, 40-45, 45-50, or more than 50 amino acids in length.

In some embodiments, the custom peptide derivatives may be conjugated to the N-termini, C-termini and/or to the side residues of existing biological proteins/peptides. In some embodiments, peptide derivatives of BNZ-γ may be conjugated to other moieties through the N-terminus, C-terminus, or side chains of the composite peptide. The other moieties may include proteins or peptides that stabilize the composite peptide, or other moieties, including without limitation, bovine serum albumin (BSA), albumin, Keyhole Limpet Hemocyanin (KLH), Fc region of IgG, a biological protein that functions as scaffold, an antibody against a cell-specific antigen, a receptor, a ligand, a metal ion and Poly Ethylene Glycol (PEG).

In some embodiments, any of the custom peptide derivatives disclosed herein can comprise one or more intra-peptide hydrocarbon linker elements. In some embodiments, the 19-mer BNZ-γ (SEQ ID NO: 1) comprises one or more intra-peptide hydrocarbon linker elements. In some embodiments, the 19-mer BNZ-γ (SEQ ID NO: 1) comprises one or more intra-peptide hydrocarbon linker elements that connect two separate amino acids positioned 4 residues apart on SEQ ID NO: 1. In some embodiments, the 19-mer BNZ-γ (SEQ ID NO: 1) comprises one or more intra-peptide hydrocarbon linker elements that connect two separate amino acids positioned 7 residues apart on SEQ ID NO: 1. In some embodiments, the 19-mer BNZ-γ (SEQ ID NO: 1) comprises one or more intra-peptide hydrocarbon linker elements that connect two separate amino acids positioned 4 residues apart on SEQ ID NO: 1 and 7 residues apart on SEQ ID NO: 1.

Several embodiments relate to custom derivative peptides of the amino acid sequence, I-K-E-F-L-Q-R-F-I-H-I-V-Q-S-I-I-N-T-S (SEQ ID NO: 1), which can inhibit the activity of one or more γc-cytokines. Custom peptide derivatives of the amino acid sequence include any peptide whose partial amino acid sequence shows approximately 50%, 50-60%, 60-70%, 70-80%, 80%, 90%, 95%, 97%, 98%, 99% or 99.8% identity to amino acid sequence: I-K-E-F-L-Q-R-F-I-H-I-V-Q-S-I-I-N-T-S (SEQ ID NO: 1). Custom peptide derivatives further include any peptide wherein a partial amino acid sequence of that peptide derivative comprises amino acids with similar physico-chemical properties to the amino acids of sequence: I-K-E-F-L-Q-R-F-I-H-I-V-Q-S-I-I-N-T-S (SEQ ID NO: 1).

In several embodiments, the amino acid residues of the custom derivative peptides retain similar physico-chemical properties with the amino acid residues of SEQ ID NO: 1, but exhibit different biological inhibition specificity to the 6 γc-cytokine family members from that of the original 19-mer peptide. Peptide derivatives of SEQ ID NO: 1 may be less than 19, 20, 21, 22, 23, 24, 25-30, 30-35, 35-40, 40-45, 45-50, or more than 50 amino acids in length.

In some embodiments, the custom peptide derivatives may be conjugated to the N-termini, C-termini and/or to the side residues of existing biological proteins/peptides. In some embodiments, the composite peptide of SEQ ID NO: 1 may be conjugated to other moieties through the N-terminus, C-terminus, or side chains of the composite peptide. In some embodiments, the other moieties may include proteins or peptides that stabilize the composite peptide, or other moieties, including without limitation, bovine serum albumin (BSA), albumin, Keyhole Limpet Hemocyanin (KLH), Fc region of IgG, a biological protein that functions as scaffold, an antibody against a cell-specific antigen, a receptor, a ligand, a metal ion and Poly Ethylene Glycol (PEG).

In some embodiments, any of the custom peptide derivatives disclosed herein can comprise one or more intra-peptide hydrocarbon linker elements. In some embodiments, the composite peptide of SEQ ID NO: 1 comprises one or more intra-peptide hydrocarbon linker elements. In some embodiments, the composite peptide of SEQ ID NO: 1 comprises one or more intra-peptide hydrocarbon linker elements that connect two separate amino acids positioned 4 residues apart on SEQ ID NO: 1. In some embodiments, the composite peptide of SEQ ID NO: 1 comprises one or more intra-peptide hydrocarbon linker elements that connect two separate amino acids positioned 7 residues apart on SEQ ID NO: 1. In some embodiments, the composite peptide of SEQ ID NO: 1 comprises one or more intra-peptide hydrocarbon linker elements that connect two separate amino acids positioned 4 residues apart on SEQ ID NO: 1 and 7 residues apart on SEQ ID NO: 1.

Several embodiments relate to custom peptide derivatives of the γc-box motifs of IL-15, IL-2, IL-21, IL-4, IL-9, or IL-7, which are depicted in FIG. 1A. Other embodiments relate to custom derivative peptides which are artificial composite peptides combining the amino acid sequence of two or more of the human IL-15, IL-2, IL-21, IL-4, IL-9, and IL-7 γc-box motifs. Several embodiments relate to custom peptide derivatives of the of the γc-box motifs of IL-15, IL-2, IL-21, IL-4, IL-9, or IL-7 having a partial amino acid sequence that shows approximately 50%, 50-60%, 60-70%, 70-80%, 80%, 90%, 95%, 97%, 98%, 99% or 99.8% identity to amino acid sequences of the of the γc-box motifs of IL-15, IL-2, IL-21, IL-4, IL-9, or IL-7. Custom peptide derivatives of the of the γc-box motifs of IL-15, IL-2, IL-21, IL-4, IL-9, or IL-7 further include any peptide wherein a partial amino acid sequence of that peptide derivative comprises amino acids with similar physico-chemical properties to the amino acids of sequence of the γc-box motifs of IL-15, IL-2, IL-21, IL-4, IL-9, or IL-7.

Several embodiments relate to custom peptide derivatives that would inhibit the function of one, all, or selective members of the γc-cytokines. In some embodiments, the custom peptide derivatives selectively target individual γc-cytokine family members. For example, a custom peptide derivative can selectively inhibit the function of IL-2, IL-4, IL-7, IL-9, IL-15, or IL-21. In other embodiments, a custom peptide derivative can inhibit 2 or more γc-cytokine family members.

For example, the custom peptide derivatives of the present embodiments can selectively inhibit the function of IL-2 in combination with one or more of IL-4, IL-7, IL-9, IL-15, and IL-21; IL-4 in combination with one or more of IL-2, IL-7, IL-9, IL-15, and IL-21; IL-7 in combination with one or more of IL-2, IL-4, IL-9, IL-15, and IL-21; IL-9 in combination with one or more of IL-2, IL-4, IL-7, IL-15, and IL-21; IL-15 in combination with one or more of IL-2, IL-4, IL-7, IL-9, and IL-21; or IL-21 in combination with one or more of IL-2, IL-4, IL-7, IL-9, and IL-15. In other embodiments, custom peptide derivatives can comprehensively target all γc-cytokine family members.

Not wishing to be bound by a particular theory, the custom peptide derivatives can inhibit the function of all or selective members of the γc-cytokines by diminishing the binding of γc-cytokines to the γc-subunit, for example, as a competitive inhibitor. Such custom peptide derivatives may be used in diverse applications, including as a clinical drug.

Several embodiments relate to custom peptide derivatives that would modulate (including enhance or reduce) the function of one, two, or more of selective members of the γc-cytokines. In some embodiments, the custom peptide derivatives selectively target individual γc-cytokine family members. For example, a custom peptide derivative can selectively enhance or inhibit the function of IL-2, IL-4, IL-7, IL-9, IL-15, or IL-21. In other embodiments, a custom peptide derivative can enhance or inhibit two or more γc-cytokine family members.

In some embodiments, one or more of the custom peptide derivatives of the conserved γc-box motif disclosed herein can inhibit the activity of one or more γc-cytokines. In some embodiments, one or more of the custom peptide derivatives of the conserved γc-box motif disclosed herein can inhibit the activity of one or more γc-cytokines by suppressing cell proliferation induced by the one or more γc-cytokines. In some embodiments, one or more of the custom peptide derivatives of the conserved γc-box motif disclosed herein can inhibit the activity of one or more γc-cytokines by inhibiting phosphorylation of the intracellular cytokine signal transduction molecule mediated by the one or more γc-cytokines. In some embodiments, one or more of the custom peptide derivatives of the conserved γc-box motif disclosed herein can inhibit the activity of one or more γc-cytokines by suppressing cell proliferation induced by the one or more γc-cytokines and by inhibiting phosphorylation of the intracellular cytokine signal transduction molecule mediated by the one or more γc-cytokines. In some embodiments, one or more of the custom peptide derivatives of the conserved γc-box motif disclosed herein can inhibit the activity of one or more γc-cytokines by one or more other mechanisms.

In some embodiments, one or more of the peptide sequences disclosed herein suppress proliferation of one or more cell types induced by one or more of the cytokines disclosed herein (e.g., IL-2, IL-4, IL-7, IL-9, IL-15, and IL-21). In some embodiments, one or more of the peptide sequences disclosed herein suppress proliferation of one or more cell types induced by all of the cytokines disclosed herein. In some embodiments, one or more of the peptide sequences disclosed herein suppress proliferation of one or more cell types induced by some but not all of the cytokines disclosed herein. In some embodiments, SEQ ID NO: 1 suppresses IL-2 IL-9, and IL-15 induced cellular proliferation.

In some embodiments, one or more of the custom peptide derivatives of the conserved γc-box motif disclosed herein can inhibit the activity of one or more γc-cytokines by inhibiting phosphorylation of one or more intracellular cytokine signal transduction molecules mediated by the one or more γc-cytokines disclosed herein (e.g., IL-2, IL-4, IL-7, IL-9, IL-15, and IL-21). In some embodiments, one or more of the custom peptide derivatives of the conserved γc-box motif disclosed herein can inhibit phosphorylation of one or more intracellular cytokine signal transduction molecules mediated by all of the γc-cytokines disclosed herein. In some embodiments, one or more of the custom peptide derivatives of the conserved γc-box motif disclosed herein can inhibit phosphorylation of one or more intracellular cytokine signal transduction molecules mediated by some but not all of the γc-cytokines disclosed herein.

Also, for example, the peptides as disclosed herein may be used to inhibit IL-15 mediated phosphorylation of the intracellular cytokine signal transduction molecule STAT-5.

Provided herein are composite peptides, and compositions, methods, and kits to modulate γc-cytokine signaling. The terms "composite peptide," "composite peptide derivative," "custom peptide," "antagonist peptides," "antagonist peptides derivatives," "oligopeptide," "polypeptide," "peptide," and "protein" can be used interchangeably when referring to the "custom peptide derivatives" provided in accordance with the present embodiments and can be used to designate a series of amino acid residues of any length. The peptides of the present embodiments may be linear or cyclic. The peptides of the present embodiments may include natural amino acids, non-natural amino acids, amino acids in the (D) stereochemical configuration, amino acids in the (L) stereochemical configuration, amino acids in the (R) stereochemical configuration, amino acids in the (S) stereochemical configuration, or a combination thereof.

Peptides of the present embodiments may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions. Side chain modifications, substitutions or a combination thereof that may be present in the custom peptide derivatives of the present embodiments include, but are not limited to, α-methyl, α-alkenyl, alkylation, methylation, benzylation, t-butylation, tosylation, alkoxycarbonylamino, and the like.

Residues other than common amino acids that may be present include, but are not limited to, penicillamine, tetramethylene cysteine, pentamethylene cysteine, mercaptopropionic acid, norleucine, pentamethylene-mercaptopropionic acid, 2-mercaptobenzene, 2-mercaptoaniline, 2-mercaptoproline, ornithine, aminoisobutyric acid, diaminobutyric acid, aminoadipic acid, m-aminomethylbenzoic acid, and diaminopropionic acid.

Peptides of the present embodiments can be produced and obtained by various methods known to those skilled in the art. For example, the peptide may be produced by genetic engineering, based on the nucleotide sequence coding for the peptide of the present embodiments, or chemically synthesized by means of peptide solid-phase synthesis and the like, or produced and obtained in their combination. One skilled in the art of solid-phase peptide synthesis can readily incorporate natural or non-natural amino acids in the (D) as well as (L), or the (R) as well as (S), stereochemical configuration. It will also be apparent to one skilled in the art of solid-phase peptide synthesis to produce and obtain peptides containing one or more intra-peptide hydrocarbon linker elements of the present embodiments utilizing α-substituted (such as α-alkenyl) natural or non-natural amino acids in one or more of (D), (L), (R) or (S), stereochemical configurations, or a combination thereof. In some embodiments, an intra-peptide hydrocarbon linker element linking α-substituted amino acids (e.g., α-alkenyl amino acids) can be generated by catalyzing one or more ring-closing metathesis. In some embodiments, one or more intra-peptide hydrocarbon linker elements can be generated by catalyzing a ring-closing metathesis using benzylidenebis(tricyclohexyl-phosphine)-dichlororuthenium (Grubb's catalyst) on the resin-bound peptide during peptide synthesis. In some embodiments, other ring-closing synthesis reactions and/or mechanisms during one or more known peptide synthesis processes are also contemplated. One skilled in the art can synthesize the custom peptide derivatives based on the present disclosure of the conserved γc-box motif and knowledge of the biochemical properties of amino acids as described in FIG. 2.

Peptides of the present embodiments may also comprise two or more α-alkenyl substituted amino acids. In some embodiments, the two or more α-alkenyl substituted amino acids are linked via one or more intra-peptide hydrocarbon linker elements incorporated at the α-alkenyl substituted amino acids. In some embodiments, the α-alkenyl substituted amino acids are utilized to catalyze the formation of an intra-peptide hydrocarbon linker element by ring-closing metathesis during peptide synthesis. Intra-peptide linker elements join separate amino acids on the same sequence of a custom peptide derivative of the present disclosure. In some embodiments, the peptides of the present disclosure are linear or cyclic.

In some embodiments, one or more intra-peptide hydrocarbon linker elements are incorporated at amino acid positions that correlate with a single α-helical turn in a secondary structure of the composite peptide. In some embodiments, when the composite peptide comprises one or more non-contiguous single α-helical turns, the amino acid positions that correlate with a single α-helical turn of the composite peptide correspond to amino acid positions i and i+4 of the composite peptide, where i is the first amino acid position of the single α-helical turn and i+4 is the last amino acid position of the single α-helical turn, and wherein amino acid positions i and i+4 comprise alpha-alkenyl substituted amino acids, and where i and i+4 are positioned 4 residues apart (4 spaced).

In some embodiments, one skilled in the art of solid-phase peptide synthesis can readily synthesize composite peptides comprising more than one intra-peptide hydrocarbon linker elements such that the composite peptide comprises more than one single α-helical turn. In some embodiments, the more than one single α-helical turns are non-contiguous, i.e., the more than one single α-helical turns do not share a substituted amino acid. For example, in some embodiments, the composite peptide can comprise one or more intra-peptide hydrocarbon linker elements of Formula 1 (See TABLE 1) that span more than one non-contiguous single α-helical turns of the composite peptide.

Not wishing to be bound to any specific peptide containing one or more intra-peptide hydrocarbon linker elements of the present embodiments, a generic peptide example containing one intra-peptide hydrocarbon linker element connecting two separate amino acids positioned 4 residues apart, or one α-helical turn (position i and position i+4), can have S-pentenylalanine (S5Ala) incorporated at each of the positions i and i+4 during solid-phase synthesis of the peptide before catalyzing ring-closing metathesis using Grubb's catalyst while the peptide is still resin-bound on the solid support. This will result in a peptide sequence containing the intra-peptide hydrocarbon linker element depicted below (SEQ ID NO: 23) positioned 4 residues apart:

SEQ ID NO: 23

∿∿X—X—X—S5Ala-X—X—X—X—S5Ala-X—X—X∿∿
    i                              i+4

In some embodiments, one or more intra-peptide hydrocarbon linker elements are incorporated at amino acid positions that correlate with a double α-helical turn in a secondary structure of the composite peptide. In some embodiments, when the composite peptide comprises one or more non-contiguous double α-helical turns, the amino acid positions that correlate with a double α-helical turn of the composite peptide correspond to amino acid positions i and i+7 of the composite peptide, where i is the first amino acid position of the double α-helical turn and i+7 is the last amino acid position of the double α-helical turn, and wherein amino acid positions i and i+7 comprise alpha-alkenyl substituted amino acids, and where i and i+7 are positioned 7 residues apart (7 spaced).

Not wishing to be bound to any specific peptide containing one or more intra-peptide hydrocarbon linker elements of the present embodiments, a generic peptide example containing one intra-peptide hydrocarbon linker element connecting two separate amino acids positioned 7 residues apart, or two α-helical turns (position i and position i+7), can have R-octenylalanine (R8Ala) incorporated at position i and S-pentenylalanine (S5Ala) incorporated at position i+7 during solid-phase synthesis of the peptide before catalyzing ring-closing metathesis using Grubb's catalyst while the peptide is still resin-bound on the solid support. This will result in a peptide sequence containing the intra-peptide hydrocarbon linker elements depicted below (SEQ ID NO: 24) positioned 7 residues apart:

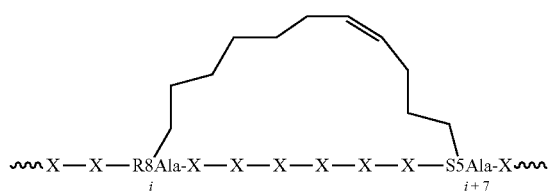

SEQ ID NO: 24

In some embodiments, one skilled in the art of solid-phase peptide synthesis can readily synthesize composite peptides comprising more than one intra-peptide hydrocarbon linker elements such that the composite peptide comprises more than one double α-helical turn. In some embodiments, the more than one double α-helical turns are non-contiguous, i.e., the more than one double α-helical turns do not share a substituted amino acid. For example, in some embodiments, the composite peptide can comprise one or more intra-peptide hydrocarbon linker elements of Formula 2 (See TABLE 1) that span more than one non-contiguous double α-helical turns of the composite peptide.

One skilled in the art of solid-phase peptide synthesis can readily synthesize peptides containing more than one intra-peptide hydrocarbon linker element of the present embodiments by incorporating α-alkenyl substituted amino acids at paired non-overlapping amino acid positions in the peptide, with each α-alkenyl substituted amino acid in the pair positioned a single α-helical turn apart (4 residues apart) or a double α-helical turn apart (7 residues apart) during solid-phase peptide synthesis before catalyzing ring-closing metathesis using Grubb's catalyst while the peptide is still resin-bound on the solid support. In some embodiments, single peptides can comprise more than one intra-peptide hydrocarbon linker element that span a single α-helical turn (4 residues apart), can contain hydrocarbon linker elements that span a double α-helical turn (7 residues apart), or can contain a combination of both a single α-helical turn (4 residues apart) and a double α-helical turn (7 residues apart) intra-peptide hydrocarbon linker elements.

Peptides containing one or more intra-peptide hydrocarbon linker elements of the present embodiments can be produced through solid-phase peptide synthesis utilizing commercially available Boc- or Fmoc-protected α-alkenyl substituted natural or non-natural amino acids in the (D) as well as (L), or the (R) as well as (S), stereochemical configuration. The Fmoc-protected α-alkenyl substituted amino acids and the resultant hydrocarbon linker element following ring-closing metathesis that may be used in the synthesis of the custom peptide derivatives of the present embodiments include, but are not limited to Table 1:

TABLE 1

| α-alkenyl Substituted Amino Acid | α-alkenyl Substituted Amino Acid |
|---|---|
| Peptide Position i S-pentenylalanine (CAS: 288617-73-2; S5Ala) | Peptide Position i+4 S5Ala |
| Hydrocarbon Linker Element Following Ring-Closing Metathesis | |

Formula 1

| Peptide Position i R-octenylalanine (CAS: 945212-26-0; R8Ala) | Peptide Position i+7 S5Ala |
|---|---|
| Hydrocarbon Linker Element Following Ring-Closing Metathesis | |

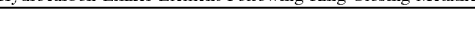

Formula 2

In some embodiments, an intra-peptide hydrocarbon linker can be further functionalized through one or more chemical reactions. In some embodiments, one or more carbon-carbon double bond(s) present in the intra-peptide hydrocarbon linker (e.g., Formula 1-Formula 2 in TABLE 1) can be utilized for organic chemical reactions to add one or more additional chemical functionalities. For example, alkene reactions may be utilized for custom peptide derivatives that contain one or more intra-peptide hydrocarbon linker elements of the present embodiments. Non-limiting examples of alkene reactions include hydroboration, oxymercuration, hydration, chlorination, bromination, addition of HF, HBr, HCl or HI, dihydroxylation, epoxidation, hydrogenation, and cyclopropanation. In some embodiments, one or more additional chemical functionalities of the intra-peptide hydrocarbon linker elements can be achieved subsequent to the alkene reaction. Non-limiting examples include covalent addition of one or more chemical group substituents, such as nucleophilic reactions with epoxide and hydroxyl groups, and the like. In some embodiments, alkene reactions may be utilized to attach biotin, radioisotopes, therapeutic agents (non-limiting examples include rapamycin, vinblastine, taxol, etc.), non-protein fluorescent chemical groups (non-limiting examples include FITC, hydrazide, rhodamine, maleimide, etc.), and protein fluorescent groups (non-limiting examples include GFP, YFP, mCherry, etc.) to one or more inter- and/or intra-peptide hydrocarbon linker elements of the present embodiments.

Non-limiting examples of composite peptides comprising one or more intra-peptide hydrocarbon linker elements are provided in TABLE 2. The examples in TABLE 2 are not limiting with respect to any specific α-alkenyl substituted amino acid useful for the synthesis of single α-helical turn (4 spaced) and/or double α-helical turn (7 spaced) intra-peptide hydrocarbon linker elements of the present embodiments and/or to any specific amino acid stereochemical configuration (e.g., (D) stereochemical configuration denoted with "d" in TABLE 2) in the custom peptide derivatives of the present embodiments.

TABLE 2

| | SEQ ID NO: |
|---|---|
| {S5Ala}-I-K-E-{S5Ala}-L-Q-R-F-I-H-I-V-Q-S-I-I-N-T-S | 11 |
| I-K-E-F-L-Q-R-{S5Ala}-I-H-I-{S5Ala}-Q-S-I-I-N-T-S | 12 |

TABLE 2-continued

| | SEQ ID NO: |
|---|---|
| I-K-E-F-L-Q-R-{R8Ala}-I-H-I-V-Q-S-{S5Ala}-I-N-T-S | 13 |
| I-K-E-F-L-Q-R-F-I-H-I-{S5Ala}-Q-S-I-{S5Ala}-N-T-S | 14 |
| I-K-E-F-L-Q-R-F-I-H-I-{R8Ala}-Q-S-I-I-N-T-{S5Ala} | 15 |
| {S5Ala₁}-I-K-E-{S5Ala₁}-L-Q-R-{S5Ala₂}-I-H-I-{S5Ala₂}-Q-S-I-I-N-T-S | 16 |
| {S5Ala₁}-I-K-E-{S5Ala₁}-L-Q-R-{R8Ala₂}-I-H-I-V-Q-S-{S5Ala₂}-I-N-T-S | 17 |
| {S5Ala₁}-I-K-E-{S5Ala₁}-L-Q-R-F-I-H-I-{S5Ala₂}-Q-S-I-{S5Ala₂}-N-T-S | 18 |
| {S5Ala₁}-I-K-E-{S5Ala₁}-L-Q-R-F-I-H-I-{R8Ala₂}-Q-S-I-I-N-T-{S5Ala₂} | 19 |
| {S5Ala₁}-I-K-E-{S5Ala₁}-L-Q-R-{S5Ala₂}-I-H-I-{S5Ala₂}-Q-S-I-I-{dN}-{dT}-{dS} | 20 |
| {S5Ala₁}-I-K-E-{S5Ala₁}-L-Q-R-{R8Ala₂}-I-H-I-V-Q-S-{S5Ala₂}-I-{dN}-{dT}-{dS} | 21 |
| {S5Ala₁}-I-K-E-{S5Ala₁}-L-Q-R-F-I-H-I-{S5Ala₂}-Q-S-I-{S5Ala₂}-{dN}-{dT}-{dS} | 22 |

*Subscript denotes corresponding pairs of hydrocarbon-linked α-alkenyl substituted amino acids In some embodiments, the therapeutic compound can be an antibody. The antibody can be developed to target a γc-cytokine, such as IL-2 or IL-15, or to a specific protein receptor whose activity and/or abundance is directly modulated by cytokine signaling, such as the transmembrane glycoprotein CD8 or proteins of the NKG2 C-type lectin receptor family, both of which are expressed on T-lymphocytes.

Some embodiments also relate to polynucleotides comprising nucleotide sequences encoding the peptides and antibodies of the present invention. "Nucleotide sequence," "polynucleotide," or "nucleic acid" can be used interchangeably, and are understood to mean either double-stranded DNA, a single-stranded DNA or products of transcription of the said DNAs (e.g., RNA molecules). Polynucleotides can be administered to cells or subjects and expressed by the cells or subjects, rather than administering the peptides themselves. Several embodiments also relate to genetic constructs comprising a polynucleotide sequence encoding the peptides of the present invention. Genetic constructs can also contain additional regulatory elements such as promoters and enhancers and, optionally, selectable markers.

Methods of Treating γc-Cytokine Mediated Diseases

Several embodiments relate to the use of therapeutic compounds, such as γc-antagonist peptides, cytokine targeted antibodies, and/or antibodies targeting a specific protein receptor whose activity and/or abundance is directly modulated by cytokine signaling in the treatment of γc-cytokine mediated diseases. Use of the therapeutic compounds according to the present embodiments allows for flexibility in the design and combination, which enables more comprehensive outcomes that would not be accomplished by conventional strategies employing small-molecule chemical inhibitors or anti-cytokine receptor antibodies.

Described herein is a novel method of modulating the action of γc-family cytokines. Such manipulations can yield effective methods of clinical interventions in treating autoimmune diseases such as alopecia, and alopecia associated disorders.

In some embodiments, compositions, methods, and kits for inhibiting, ameliorating, reducing a severity of, treating, delaying the onset of, or preventing at least one alopecia related disorder are described. In some embodiments, the therapeutic compounds described herein may be used for inhibiting, ameliorating, reducing a severity of, treating, delaying the onset of, or preventing one or more of alopecia areata, alopecia totalis, alopecia subtotalis, alopecia universalis, alopecia diffusa, ophiasis-type alopecia areata, and other immune-mediated diseases associated with alopecia such as lichen planus, lichen sclerosus, lichen sclerosus et atrophicus, atopy, atopic dermatitis, psoriasis, psoriasis vugaris, psoriasis capitis, psoriasis guttate, psoriasis inversa, psoriatic arthritis, eczema, pemphigus, pemphigus vulgaris, pemphigus foliaceus, pemphigus vegetans, pemphigus erythematosus, mucous membrane pemphigoid, scarring mucous membrane pemphigoid, bullous pemphigoid, myasthenia gravis, thyroid disorders, Hashimoto's thyroiditis, hypothyroidism, endemic goiter, Addison's disease, morphea scleroderma, urticaria, prurigo, rosacea vitiligo, vitiligo, and graft-versus-host disease (GvHD).

Several embodiments relate to therapeutic compounds that would modulate the signaling of all or selective members of the γc-cytokines. In some embodiments, therapeutic compounds selectively modulate the signaling of individual γc-cytokine family members. In other embodiments, therapeutic compounds can comprehensively modulate the signaling of all γc-cytokine family members (Simul-Block). In some embodiments, therapeutic compounds can selectively modulate the signaling of subsets of the γc-cytokines. Not wishing to be bound by a particular theory, the therapeutic compounds can modulate the function of all or selective members of the γc-cytokines by diminishing the binding of γc-cytokines to the γc-subunit, for example, as a competitive inhibitor, or by modulating the activity and/or abundance of a specific protein receptor that is itself directly modulated by γc-cytokine signaling.

Several members of the γc-cytokine family have been implicated as being involved in alopecia disease progression. Alopecia is an immune-mediated disorder of the skin where there exists a T-cell hyperproliferative environment supporting T-cell targeting of hair follicle autoantigens ultimately resulting in hair loss. IL-2 and IL-15 expression is elevated in the lesional scalp biopsies of patients (Fuentes-Duculan et al. 2016 Exp Dermatol 4:282-6, Suarez-Farinas et al. 2015 J. Allergy Clin. Immunol. 136:1277-87, Waldmann 2013 J Investig Dermatol Symp Proc 16:S28-30.), and antibodies targeting the γc-cytokines IL-2 and IL-15 each showed inhibitory activity in an alopecia mouse model, but none of the blocking antibodies alone could reverse the established disorder (Xing et al. 2014 Nat Med 9:1043-9.). IL-21 expression is elevated in the serum of alopecia patients versus healthy controls (Atwa et al. 2016 Int J Dermatol 55:666-72.), and genome-wide association studies have also positively correlated IL-2 and IL-21 with alopecia (Jagielska et al. 2012 J Invest Dermatol 132:2192-7, Petukhova et al. 2010 Nature 466:113-7.).

Vitiligo is an immune-mediated disorder of the skin associated with an influx of T-cells in the epidermis which results in melanocyte destruction and the appearance of white patches on the body surface. A recent study showed that blocking IL-15 signaling via antibody treatment was an effective therapeutic strategy in mice with established vitiligo (Richmond et al. 2018 Sci Transl Med 10:450). Interestingly, the antibody used in the study targeted CD122, the private cytokine-specific receptor subunit common to both IL-15 and IL-2. Indeed IL-2 expression has been shown to be elevated in the serum of localized vitiligo and generalized vitiligo patients and is positively correlated with disease severity (Sushama et al. 2018 J Cosmet Dermatol 00:1-5).

Pemphigoid and pemphigus are immune-mediated disorders of the skin characterized by the presence of large fluid-filled blisters on the body surface. In early studies both pemphigoid and pemphigus blister fluid from human patients showed elevated IL-2 activity (Grando et al., 1989, Arch Dermatol. 125:925-30). Pemphigoid patients also displayed increased T-cell activation and elevated IL-2 levels (Schaller et al., 1990, Arch Dermatol. Res. 282:223-6). A separate study assessed the IL-15 level in both pemphigoid and pemphigus patients, and found that patients of either disease displayed increased IL-15 serum levels that were positively correlated with disease severity (D'Auria et al., 1999, Arch Dermatol. Res. 291:354-6).

Certain γc-cytokines have been shown to be positively correlated with psoriasis. Psoriasis is an immune-mediated disorder of the skin characterized by scaly red patches of extra skin cells that are often dry, itchy, and sometimes painful. The expression of IL-15 is elevated in skin lesions in psoriasis patients (Waldmann 2013 J Investig Dermatol Symp Proc 16:S28-30.). An IL-15 specific antibody, which potently interfered with the assembly of the IL-15 cytokine-receptor signaling complex, reduced the severity of the disease in a human psoriasis xenograft model (Villadsen et al., 2003, J. Clin. Invest. 112:1571-80). Another γc-cytokine, IL-21, has also been shown to be elevated in psoriatic patients and positively correlated with disease severity (Caruso et al. 2009 Cell Cycle 8: 3629-30, Botti et al. 2012 Curr Pharm Biotechnol 13: 1861-7, He et al. 2012, Br. J. Dermatol. 167:191-3). Blockade of the cytokine via anti-IL-21 antibody treatment resulted in a significant reduction in keratinocyte proliferation and inflammation in a human psoriasis xenograft mouse model (Caruso et al., 2009 Nat. Med. 15:1013-5).

Graft versus host disease (GvHD) can often result following hematopoietic cell transplantation in a patient as host cells are recognized as foreign entities by a donor's T-lymphocytes. GvHD manifests itself by host organ tissue damage as the donor-derived T-cells differentiate into CD4 and CD8 effector cells with the production of pro-inflammatory cytokines and direct CD8 T-cell cytotoxic effects. As it is well known that members of the γc-cytokine family are involved in the activation of CD4 and CD8 T-cells, the positive association of a number of γc-cytokines with GvHD pathogenesis has been reported. The prophylactic use of two IL-2 receptor antagonistic antibodies showed beneficial effects on GvHD in hematologic malignancy patients following donor-peripheral blood stem cell transplantation (Fang et al., 2012 Biol Blood Marrow Transplant. 18:754-62). Serum levels of IL-15 have also been shown to elevate sharply in GvHD patients within the first month of post-transplantation (Chik et al. 2003, J Pediatr Hematol Oncol. 25:960-4), and donor-derived IL-15 was shown to be critical for acute GvHD in a murine GvHD model (Blaser et al., 2005 Blood 105:894-901). Lastly, IL-21 expression was observed in skin and colon samples of GvHD patients, but not in GvHD-free control samples, and in GvHD murine models, serum IL-21 levels were elevated, and use of anti-human IL-21 antibodies reduced weight-loss and mortality associated with GvHD after administration (Hippen et al. 2012 Blood 119:619-28, Bucher et al. 2009 Blood 114:5375-84).

Several embodiments relate to the use of therapeutic antagonist peptides that selectively inhibit the activity of IL-15, either alone or in combination with the other γc-cytokine family members, as a therapeutic agent for alopecia and/or alopecia associated disorders. In some embodiments, custom derivative antagonist peptides that selectively inhibit IL-2, IL-15, IL-9, a combination of IL-2 and IL-15, a combination of IL-2 and IL-9, and/or a combination of IL-15 and IL-9 activities are used as a therapeutic agent for treating alopecia and/or alopecia associated diseases. In some embodiments, the effect of custom derivative antagonist peptides that selectively inhibit a combination of IL-2 and IL-15, a combination of IL-2 and IL-9, and/or a combination of IL-15 and IL-9 can be additive or synergistic. Several embodiments relate to the use of SEQ ID NO: 2 to treat alopecia and/or alopecia associated disorders. Several embodiments relate to the use of BNZ-γ to treat alopecia and/or alopecia associated disorders. Several embodiments relate to the use of SEQ ID NO: 1 to treat alopecia and/or alopecia associated disorders.

Several embodiments relate to the use of therapeutic compounds, either alone or in combination, as a therapeutic agent for alopecia and/or alopecia associated disorders. In some embodiments, the therapeutic compound is SEQ ID NO: 2. In some embodiments, the therapeutic compound is BNZ-γ. In some embodiments, the therapeutic compound is SEQ ID NO: 1. In some embodiments, the therapeutic compound is an anti-CD8 antibody. In some embodiments, the therapeutic compound is an anti-IL-2 antibody. In some embodiments, the therapeutic compound is an anti-IL-15 antibody. In some embodiments, the therapeutic compound is an anti-NKG2A antibody.

An additive effect is observed when the effect of a combination is equal to the sum of the effects of the individuals in the combination (e.g., the effect of a combination of two or more therapeutic compounds is equal to the sum of the effects of each therapeutic compound individually). A synergistic effect is observed when the effect of a combination is greater than the sum of the effects of the individuals in the combination (e.g., the effect of a combination of two or more therapeutic compounds is greater than the sum of the effects of each therapeutic compound individually). A synergistic effect is greater than an additive effect. Additive effect, synergistic effect, or both can occur in human patients, non-human patients, non-patient human volunteers, in vivo models, ex vivo models, in vitro models, etc.

In some embodiments, two or more therapeutic compounds disclosed herein can be used in combination. In some embodiments, two or more therapeutic compounds disclosed herein when used in combination yield an additive effect. In some embodiments, two or more therapeutic compounds disclosed herein when used in combination yield a synergistic effect. Synergistic effect can range from about >1 to about 100-fold. In some embodiments, the synergistic effect is about 2 to about 20-fold. In some embodiments, the synergistic effect is about 20 to about 100-fold. In some embodiments, the synergistic effect is from >1, 2, 3, 4, 5, 6, 7, 8, 9, 10, 20, 30, 40, 50, 60, 70, 80, 90, or 100-fold, or within a range defined by any two of the aforementioned values.

Another embodiment relates to the development of chemical compounds (non-peptide, non-protein) that have a spatial structure which resembles the 19-mer amino acid sequence I-K-E-F-L-Q-R-F-I-H-I-V-Q-S-I-I-N-T-S (SEQ ID NO: 1) and can fit into the pocket of the γc-subunit to structurally hinder the access of a γc-cytokine to the γc-subunit for binding. Some embodiments relate to the use of structurally similar chemical compounds as inhibitors of γc-cytokine activity. Such molecular mimicry strategy to further refine the development of synthetic compounds resembling in structure to existing biological peptide/proteins is described in Orzaez et al., 2009 Chem. Med. Chem. 4:146-160. Another embodiment relates to administration of chemical compounds (non-peptide, non-protein) that have a resembling 3D structure as the 19-mer amino acids sequence I-K-E-F-L-Q-R-F-I-H-I-V-Q-S-I-I-N-T-S (SEQ ID NO: 1) for inhibiting, ameliorating, reducing a severity of, treating, delaying the onset of, or preventing one or more alopecia and/or alopecia associated disorders.

Several embodiments relate to the administration of a peptide of amino acid sequence I-K-E-F-L-Q-R-F-I-H-I-V-Q-S-I-I-N-T-S (SEQ ID NO: 1) for inhibiting, ameliorating, reducing a severity of, treating, delaying the onset of, or preventing one or more alopecia and/or alopecia associated disorders. Another embodiment relates to the administration of derivative peptides of amino acid sequence I-K-E-F-L-Q-R-F-I-H-I-V-Q-S-I-I-N-T-S (SEQ ID NO: 1), wherein the amino acid sequence of the derivative peptide has similar physico-chemical properties as a peptide of the amino acid sequence I-K-E-F-L-Q-R-F-I-H-I-V-Q-S-I-I-N-T-S (SEQ ID NO: 1), but has distinct biological activity, for inhibiting, ameliorating, reducing a severity of, treating, delaying the onset of, or preventing one or more alopecia and/or alopecia associated disorders. Another embodiment relates to administration of a peptide of amino acid sequence I-K-E-F-L-Q-R-F-I-H-I-V-Q-S-I-I-N-T-S (SEQ ID NO: 1) conjugated to the N- and C-termini or to the side residues of existing biological proteins/peptides into patients for inhibiting, ameliorating, reducing a severity of, treating, delaying the onset of, or preventing one or more alopecia and/or alopecia associated disorders.

Several embodiments relate to the administration of a peptide of amino acid sequence I-K-E-F-L-Q-R-F-I-H-I-V-Q-S-I-I-N-T-S (SEQ ID NO: 1) for inhibiting, ameliorating, reducing a severity of, treating, delaying the onset of, or preventing one or more alopecia and/or alopecia associated disorders. Another embodiment relates to the administration of peptide derivatives of amino acid sequence I-K-E-F-L-Q-R-F-I-H-I-V-Q-S-I-I-N-T-S (SEQ ID NO: 1), wherein the amino acid sequence of the derivative peptide has similar physico-chemical properties as a peptide of the amino acid sequence I-K-E-F-L-Q-R-F-I-H-I-V-Q-S-I-I-N-T-S (SEQ ID NO: 1), but has distinct biological activity, for inhibiting, ameliorating, reducing a severity of, treating, delaying the onset of, or preventing one or more alopecia and/or alopecia associated disorders. Another embodiment relates to administration of a peptide of amino acid sequence I-K-E-F-L-Q-R-F-I-H-I-V-Q-S-I-I-N-T-S (SEQ ID NO: 1) conjugated to the N- and C-termini or to the side residues of existing biological proteins/peptides into patients for inhibiting, ameliorating, reducing a severity of, treating, delaying the onset of, or preventing one or more alopecia and/or alopecia associated disorders.

Several embodiments relate to administration of polyclonal and monoclonal antibodies raised against a peptide comprising of amino acid sequence I-K-E-F-L-Q-R-F-I-H-I-V-Q-S-I-I-N-T-S (SEQ ID NO: 1) into patients as an immunogen for inhibiting, ameliorating, reducing a severity of, treating, delaying the onset of, or preventing one or more alopecia and/or alopecia associated disorders. Another embodiment relates to administration of polyclonal and monoclonal antibodies that were raised against derivative peptides of amino acid sequence I-K-E-F-L-Q-R-F-I-H-I-V-Q-S-I-I-N-T-S (SEQ ID NO: 1), wherein the amino acid sequence of the derivative peptide has similar physico-chemical properties as a peptide of the amino acid sequence I-K-E-F-L-Q-R-F-I-H-I-V-Q-S-I-I-N-T-S (SEQ ID NO: 1), but has distinct biological activity, into patients as an immunogen for inhibiting, ameliorating, reducing a severity of, treating, delaying the onset of, or preventing one or more alopecia and/or alopecia associated disorders.

Several embodiments relate to administration of polyclonal and monoclonal antibodies raised against IL-2 into patients as an immunogen for inhibiting, ameliorating, reducing a severity of, treating, delaying the onset of, or preventing one or more alopecia and/or alopecia associated disorders. Another embodiment relates to administration of polyclonal and monoclonal antibodies raised against IL-15 into patients as an immunogen for inhibiting, ameliorating, reducing a severity of, treating, delaying the onset of, or preventing one or more alopecia and/or alopecia associated disorders. Another embodiment relates to administration of polyclonal and monoclonal antibodies raised against the transmembrane glycoprotein T-cell co-receptor CD8 into patients as an immunogen for inhibiting, ameliorating, reducing a severity of, treating, delaying the onset of, or preventing one or more alopecia and/or alopecia associated disorders. Another embodiment relates to administration of polyclonal and monoclonal antibodies raised against members of the C-type lectin receptor NKG2 family, for example NKG2D, NKG2A, into patients as an immunogen for inhibiting, ameliorating, reducing a severity of, treating, delaying the onset of, or preventing one or more alopecia and/or alopecia associated disorders.

Administration of Therapeutic Compounds

The present embodiments also encompass the use of one or more therapeutic compounds selected from the group consisting of a γc-cytokine antagonist peptide, a γc-cytokine antagonist peptide derivative, anti-CD8 antibody, anti-IL-2 antibody, anti-IL-15 antibody, anti-NKG2A antibody, or a combination thereof for the manufacture of a medicament for inhibiting, ameliorating, reducing a severity of, treating, delaying the onset of, or preventing one or more alopecia and/or alopecia associated disorders. The present embodiments also encompass a pharmaceutical composition that includes one or more therapeutic compounds in combination with a pharmaceutically acceptable carrier. The pharmaceutical composition can include a pharmaceutically acceptable carrier and a non-toxic therapeutically effective amount of therapeutic compounds, or other compositions of the present embodiments.

The present embodiments provide methods of using pharmaceutical compositions comprising an effective amount of therapeutic compounds in a suitable diluent or carrier. A therapeutic compound of the present embodiments can be formulated according to known methods used to prepare pharmaceutically useful compositions. A therapeutic compound can be combined in admixture, either as the sole active material or with other known active materials, with pharmaceutically suitable diluents (e.g., phosphate, acetate, Tris-HCl), preservatives (e.g., thimerosal, benzyl alcohol, parabens), emulsifying compounds, solubilizers, adjuvants, and/or carriers such as bovine serum albumin.

In some embodiments, one or more compositions and kits comprising one or more of the therapeutic compounds disclosed herein are contemplated. In some embodiments, one or more compositions and kits are used for preventing and/or treating one or more diseases. In some embodiments, one or more compositions and kits are used for inhibiting, ameliorating, reducing a severity of, treating, delaying the onset of, or preventing one or more alopecia and/or an alopecia associated disorder.

In some embodiments, the one or more compositions and kits comprising one or more of the therapeutic compounds are administered to a subject in need thereof via any of the routes of administration provided herein. In some embodiments, the one or more compositions and kits comprises one or more of the therapeutic compounds at a therapeutically effective amount to modulate the signaling of one or more γc-cytokines selected from the group consisting of IL-2, IL-4, IL-7, IL-9, IL-15, and IL-21. In some embodiments, the one or more compositions and kits comprises one or more of the therapeutic compounds at a therapeutically effective amount to prevent and/or treat one or more diseases. In some embodiments, the one or more compositions and kits comprising one or more of the therapeutic compounds additionally comprise one or more pharmaceutically acceptable carriers, diluents, excipients or combinations thereof.

In some embodiments, one or more therapeutic compounds in the one or more compositions and kits are formulated as suitable for administration to a subject for preventing and/or treating one or more diseases. In some embodiments, one or more therapeutic compounds in the one or more compositions and kits are formulated as suitable for administration to a subject for preventing and/or treating alopecia and/or an alopecia associated disorder.

In some embodiments, one or more therapeutic compounds selected from the group consisting of SEQ ID NO: 1, SEQ ID NO: 2, an anti-CD8 antibody, an anti-IL-2 antibody, an anti-IL-15 antibody, and an anti-NKG2A antibody in the one or more compositions and kits are formulated as suitable for administration to a subject for preventing and/or treating one or more diseases. In some embodiments, one or more composite peptides selected from the group consisting of SEQ ID NO: 1, SEQ ID NO: 2, an anti-CD8 antibody, an anti-IL-2 antibody, an anti-IL-15 antibody, and an anti-NKG2A antibody in the one or more compositions and kits are formulated as suitable for administration to a subject for inhibiting, ameliorating, reducing a severity of, treating, delaying the onset of, or preventing one or more alopecia and/or an alopecia associated disorder.

In some embodiments, one or more derivatives of the one or more composite peptides selected from the group consisting of SEQ ID NO: 1, SEQ ID NO: 2; and an anti-CD8 antibody, an anti-IL-2 antibody, an anti-IL-15 antibody, and an anti-NKG2A antibody in the one or more compositions and kits are formulated as suitable for administration to a subject for preventing and/or treating one or more diseases. In some embodiments, one or more derivatives of the one or more composite peptides selected from the group consisting of SEQ ID NO: 1, SEQ ID NO: 2; and an anti-CD8 antibody, an anti-IL-2 antibody, an anti-IL-15 antibody, and an anti-NKG2A antibody in the one or more compositions and kits are formulated as suitable for administration to a subject for inhibiting, ameliorating, reducing a severity of, treating, delaying the onset of, or preventing one or more alopecia and/or an alopecia associated disorder.

The terms "disease," "disorder," and "biological condition" can be used interchangeably when referring to "inhibiting, ameliorating, reducing a severity of, treating, delaying the onset of, or preventing one or more diseases" provided in accordance with the present embodiments.

In some embodiments, the one or more derivatives of the one or more composite peptides comprise amino acid sequences that shares about 50% to about 99% identity with the one or more composite peptides. In some embodiments, the one or more derivatives of the one or more composite peptides comprise amino acid sequences that shares 50%, 50-60%, 60-70%, 70-80%, 80%, 90%, 95%, 97%, 98%, 99% or 99.8% identity with the one or more composite peptides, or within a range defined by any two of the aforementioned values.

In some embodiments, one or more alopecia associated disorder is selected from the group consisting of alopecia areata, alopecia totalis, alopecia subtotalis, alopecia universalis, alopecia diffusa, ophiasis-type alopecia areata, lichen planus, lichen sclerosus, lichen sclerosus et atrophicus, atopy, atopic dermatitis, psoriasis, psoriasis vugaris, psoriasis capitis, psoriasis guttate, psoriasis inversa, psoriatic arthritis, eczema, pemphigus, pemphigus vulgaris, pemphigus foliaceus, pemphigus vegetans, pemphigus erythematosus, mucous membrane pemphigoid, scarring mucous membrane pemphigoid, bullous pemphigoid, myasthenia gravis, thyroid disorders, Hashimoto's thyroiditis, hypothyroidism, endemic goiter, Addison's disease, morphea scleroderma, urticaria, prurigo, rosacea vitiligo, vitiligo, and graft-versus-host disease (GvHD).

Suitable carriers and their formulations are described in Remington's Pharmaceutical Sciences, 16$^{th}$ ed. 1980 Mack Publishing CO, and Overview of Antibody Drug Delivery (Awwad et al. 2018 Pharmaceutics 10:83). Additionally, such compositions can contain a therapeutic compound complexed with polyethylene glycol (PEG), metal ions, or incorporated into polymeric compounds such as polyacetic acid, polyglycolic acid, hydrogels etc., or incorporated into liposomes, microemulsions, micelles, unilamellar or multilamellar vesicles, erythrocyte ghosts, or spheroblasts. Such compositions will influence the physical state, solubility, stability, rate of in vivo release, and rate of in vivo clearance of a therapeutic compound. A therapeutic compound can be conjugated to antibodies against cell-specific antigens, receptors, ligands, or coupled to ligands for tissue-specific receptors.

Methods of administrating therapeutic compounds of the present embodiments may be selected as appropriate, depending on factors, such as the type of diseases, the condition of subjects, and/or the site to be targeted. The therapeutic compounds can be administered topically, orally, parenterally, rectally, or by inhalation. Topical administration of therapeutic compounds can be achieved through formulation into lotions, liniments (balms), solutions, ointments, creams, pastes, gels, or other suitable topical delivery systems as appropriate (Gupta et al. 2016 Indo Amer J Pharm Res 6:6353-69.). Topical formulation components can include emollient and/or stiffening agents such as cetyl alcohol, cetyl ester wax, carnauba wax, lanolin, lanolin alcohols, paraffin, petrolatum, polyethylene glycol, stearic acid, stearyl alcohol, white or yellow wax; emulsifying and/or solubilizing agents such as polysorbate 20, polysorbate 80, polysorbate 60, poloxamer, sorbitan monostearate, sorbitan monooleate, sodium lauryl sulfate, propylene glycol monostearate; humectants such as glycerin, propylene glycol, polyethylene glycol; thickening/gelling agents such as carbomer, methyl cellulose, sodium carboxyl methyl cellulose, carrageenan, colloidal silicon dioxide, guar gum, hydroxypropyl cellulose, hydroxypropyl methyl cellulose, gelatin, polyethylene oxide, alginic acid, sodium alginate, fumed silica; preservative agents such as benzoic acid, propyl paraben, methyl paraben, imidurea, sorbic acid, potassium sorbate, benzalkonium chloride, phenyl mercuric acetate, chlorobutanol, phenoxyethanol; permeation enhancing agents such as propylene glycol, ethanol, isopropyl alcohol, oleic acid, polyethylene glycol; antioxidant agents such as butylated hydroxyanisole, butylated hydroxytoluene; buffering agents such as citric acid, phosphoric acid, sodium hydroxide, monobasic sodium phosphate; and vehicle agents such as purified water, propylene glycol, hexylene glycol, oleyl alcohol, propylene carbonate, and mineral oil (Chang et al. 2013 AAPS J 15:41-52.). Oral formulation components can include fatty acids and derivatives such as lauric acid, caprylic acid, oleic acid; bile salts such as sodium cholate, sodium deoxycholate, sodium taurodeoxycholate, sodium glycocholate; chelators such as citric acid, sodium salicylate; alkylglycoside containing polymers, cationic polymers, anionic polymers, and nanoparticles; and surfactants such as sodium dodecyl sulfate, sodium laurate dodecylmaltoside, polaxamer, sodium myristate, sodium laurylsulfate, quillayasaponin, and sucrose palmitate (Liu et al. 2018 Expert Opin Drug Del 15:223-33, Aguirre et al. 2016 Adv Drug Deliv Rev 106: 223-41.). The term "parenteral" includes subcutaneous injections, intravenous, intramuscular, intraperitoneal, intracisternal injection, or infusion techniques. These compositions will typically include an effective amount of a therapeutic compound, alone or in combination with an effective amount of any other active material. Several non-limiting routes of administrations are possible including parenteral, subcutaneous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

The one or more therapeutic compounds disclosed herein can be administered at any dose, via any of the routes of administration, and at any frequency of administration as determined by one of ordinary skill in the art based on various parameters. Non-limiting examples of which include the condition being treated, the severity of the condition, patient compliance, efficacy of treatment, side effects, etc.

The amount of the therapeutic compound contained in pharmaceutical compositions of the present embodiments, dosage form of the pharmaceutical compositions, frequency of administration, and the like may be selected as appropriate, depending on factors, such as the type of diseases, the condition of subjects, and/or the site to be targeted. Such dosages and desired drug concentrations contained in the compositions may vary affected by many parameters, including the intended use, patient's body weight and age, and the route of administration. Pilot studies will first be conducted using animal studies and the scaling to human administration will be performed according to art-accepted practice.

In one embodiment, host cells that have been genetically modified with a polynucleotide encoding at least one therapeutic compound are administered to a subject for inhibiting, ameliorating, reducing a severity of, treating, delaying the onset of, or preventing one or more alopecia and/or an alopecia associated disorder. The polynucleotide is expressed by the host cells, thereby producing the therapeutic compound within the subject. Preferably, the host cells are allogeneic or autogeneic to the subject.

In a further aspect, the one or more therapeutic compounds selected from the group consisting of a γc-cytokine antagonist peptide, a γc-cytokine antagonist peptide derivative, anti-CD8 antibody, anti-IL-2 antibody, anti-IL-15 antibody, anti-NKG2A antibody, or a combination thereof can be used in combination with other therapies, for example, therapies inhibiting cancer cell proliferation and growth. The phrase "combination therapy" embraces the administration of the one or more therapeutic compounds selected from the group consisting of a γc-cytokine antagonist peptide, a γc-cytokine antagonist peptide derivative, anti-CD8 antibody, anti-IL-2 antibody, anti-IL-15 antibody, anti-NKG2A antibody, or a combination thereof and one or more additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected).

A combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by an appropriate route including, but not limited to, oral routes, intravenous routes, intramuscular routes, and direct absorption through mucous membrane tissues. There therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporarily removed from the administration of the therapeutic agents, perhaps by days or even weeks.

In certain embodiments, the one or more therapeutic compounds selected from the group consisting of a γc-cytokine antagonist peptide, a γc-cytokine antagonist peptide derivative, anti-CD8 antibody, anti-IL-2 antibody, anti-IL-15 antibody, anti-NKG2A antibody, or a combination thereof can be administered in combination with at least one anti-proliferative agent selected from the group consisting of chemotherapeutic agent, an antimetabolite, and antitumorgenic agent, and antimitotic agent, and antiviral agent, and antineoplastic agent, an immunotherapeutic agent, and a radiotherapeutic agent.

In certain embodiments, the one or more therapeutic compounds selected from the group consisting of a γc-cytokine antagonist peptide, a γc-cytokine antagonist peptide derivative, anti-CD8 antibody, anti-IL-2 antibody, anti-IL-15 antibody, anti-NKG2A antibody, or a combination thereof can be administered in combination with at least one anti-inflammatory agent selected from the group consisting of steroids, corticosteroids, and nonsteroidal anti-inflammatory drugs.

Also provided are kits for performing any of the above methods. Kits may include the one or more therapeutic compounds selected from the group consisting of a γc-cytokine antagonist peptide, a γc-cytokine antagonist peptide derivative, anti-CD8 antibody, anti-IL-2 antibody, anti-IL-15 antibody, anti-NKG2A antibody, or a combination thereof according to the present embodiments. In some embodiments, the kit may include instructions. Instructions may be in written or pictograph form, or may be on recorded media including audio tape, audio CD, video tape, DVD, CD-ROM, or the like. The kits may comprise packaging.

Additional Embodiments

In some embodiments of the method, the composite peptide comprises the amino acid sequence D/E-F-L-E/Q/N-S/R-X-I/K-X-L/I-X-Q (SEQ ID NO: 2), wherein X denotes any amino acid. In some embodiments of the method, the composite peptide derivative shares at least about 50% identity with a peptide of SEQ ID NO: 2. In some embodiments of the method, the composite peptide derivative shares at least about 90% identity with a peptide of SEQ ID NO: 2. In some embodiments of the method, the composite peptide derivative shares at least about 95% identity with a peptide of SEQ ID NO: 2. In some embodiments of the method, the composite peptide and the composite peptide derivative have similar physico-chemical properties but distinct biological activities.

In some embodiments of the method, the composite peptide comprises the amino acid sequence I-K-E-F-L-Q-R-F-I-H-I-V-Q-S-I-I-N-T-S (SEQ ID NO: 1) (BNZ-γ). In some embodiments of the method, the composite peptide derivative shares at least about 50% identity with a peptide of SEQ ID NO: 1. In some embodiments of the method, the composite peptide derivative shares at least about 90% identity with a peptide of SEQ ID NO: 1. In some embodiments of the method, the composite peptide derivative shares at least about 95% identity with a peptide of SEQ ID NO: 1. In some embodiments of the method, the composite peptide and the composite peptide derivative have similar physico-chemical properties but distinct biological activities.

In some embodiments of the method, the composite peptide comprises the amino acid sequence I-K-E-F-L-Q-R-F-I-H-I-V-Q-S-I-I-N-T-S (SEQ ID NO: 1). In some embodiments of the method, the composite peptide derivative shares at least about 50% identity with a peptide of SEQ ID NO: 1. In some embodiments of the method, the composite peptide derivative shares at least about 90% identity with a peptide of SEQ ID NO: 1. In some embodiments of the method, the composite peptide derivative shares at least about 95% identity with a peptide of SEQ ID NO: 1. In some embodiments of the method, the composite peptide and the composite peptide derivative have similar physico-chemical properties but distinct biological activities.

In some embodiments of the method, the composite peptide or composite peptide derivative inhibits the activity of one or more γc-cytokines. In some embodiments of the method, the one or more γc-cytokines are selected from the group consisting of IL-2, IL-4, IL-7, IL-9, IL-15 and IL-21. In some embodiments of the method, the composite peptide or composite peptide derivative inhibits the activity of IL-2, IL-15 and IL-9. In some embodiments of the method, the composite peptide or composite peptide derivative inhibits the activity of IL-2 and IL-15. In some embodiments of the method, the composite peptide or composite peptide derivative inhibits the activity of IL-15 and IL-9. In some embodiments of the method, the composite peptide or composite peptide derivative inhibits the activity of IL-15 and IL-21.

In some embodiments, the composite peptide or composite peptide derivative comprises a signal peptide. In some embodiments, the composite peptide or composite peptide derivative is further conjugated to one or more additional moieties at the N terminus, C terminus or a side residue of the composite peptide or composite peptide derivative. In some embodiments of the composite peptide or composite peptide derivative, the one or more additional moieties are selected from the group consisting of bovine serum albumin (BSA), albumin, Keyhole Limpet Hemocyanin (KLH), Fc region of IgG, a biological protein that functions as scaffold, an antibody against a cell-specific antigen, a receptor, a ligand, a metal ion, and Poly Ethylene Glycol (PEG).

In some embodiments, the composite peptide or composite peptide derivative comprises at least two alpha-alkenyl substituted amino acids, and wherein the at least two alpha-alkenyl substituted amino acids are linked via at least one intra-peptide hydrocarbon linker element is provided. In some embodiments of the composite peptide, the at least two alpha-alkenyl substituted amino acids are linked to form the at least one intra-peptide hydrocarbon linker element by ring closing metathesis, wherein the ring closing metathesis is catalyzed by Grubb's catalyst.

In some embodiments, an amino acid in the composite peptide is selected from the group consisting of natural amino acids, non-natural amino acids, (D) stereochemical configuration amino acids, (L) stereochemical configuration amino acids, (R) stereochemical configuration amino acids and (S) stereochemical configuration amino acids, and wherein the at least two alpha-alkenyl substituted amino acids are selected from S-pentenylalanine (CAS: 288617-73-2; S5Ala) and R-octenylalanine (CAS: 945212-26-0; R8Ala).

In some embodiments of the composite peptide, the at least two alpha-alkenyl substituted amino acids linked by the at least one intra-peptide hydrocarbon are separated by n−2 amino acids, wherein n represents the number of amino acids encompassed by the intra-peptide linkage.

In some embodiments of the composite peptide, when the at least two alpha-alkenyl substituted amino acids linked by the at least one intra-peptide hydrocarbon are separated by three amino acids, the at least one intra-peptide hydrocarbon linker element spans a single α-helical turn of the composite peptide.

In some embodiments of the composite peptide, when the composite peptide comprises one or more non-contiguous single α-helical turns, the amino acid positions that correlate with a single α-helical turn of the composite peptide correspond to amino acid positions i and i+4 of the composite peptide, where i is the first amino acid position of the single α-helical turn and i+4 is the last amino acid position of the single α-helical turn, and wherein amino acid positions i and i+4 comprise alpha-alkenyl substituted amino acids. In some embodiments of the composite peptide, when the alpha-alkenyl substituted amino acid at position i is S5Ala, the alpha-alkenyl substituted amino acid at position i+4 is also S5Ala, the hydrocarbon linker element formed by the ring-closing metathesis is represented by Formula 1.

In some embodiments of the composite peptide, when the at least two alpha-alkenyl substituted amino acids linked by the at least one intra-peptide hydrocarbon are separated by six residues, the at least one intra-peptide hydrocarbon linker element spans a double α-helical turn of the composite peptide.

In some embodiments of the composite peptide, when the composite peptide comprises one or more non-contiguous double α-helical turns, the amino acid positions that correlate with a double α-helical turn of the composite peptide correspond to amino acid positions i and i+7 of the composite peptide, where i is the first amino acid position of the double α-helical turn and i+7 is the last amino acid position of the double α-helical turn, and wherein amino acid positions i and i+7 comprise alpha-alkenyl substituted amino acids. In some embodiments of the composite peptide, when the alpha-alkenyl substituted amino acid at position i is R8Ala, the alpha-alkenyl substituted amino acid at position i+7 is S5Ala, the hydrocarbon linker element formed by the ring-closing metathesis is represented by Formula 2.

In some embodiments, the composite peptide comprises amino acid sequences of at least two interleukin (IL) protein gamma-c-box D-helix regions, wherein the composite peptide comprises the amino acid sequence I-K-E-F-L-Q-R-F-I-H-I-V-Q-S-I-I-N-T-S (SEQ ID NO: 1), and wherein the composite peptide comprises at least two alpha-alkenyl substituted amino acids, and wherein the at least two alpha-alkenyl substituted amino acids are linked via at least one intra-peptide hydrocarbon linker element.

In some embodiments, the composite peptide comprises amino acid sequences of at least two interleukin (IL) protein gamma-c-box D-helix regions, wherein the composite peptide comprises the amino acid sequence I-K-E-F-L-Q-R-F-I-H-I-V-Q-S-I-I-N-T-S (SEQ ID NO: 1), and wherein the composite peptide comprises at least two alpha-alkenyl substituted amino acids, and wherein the at least two alpha-alkenyl substituted amino acids are linked via at least one intra-peptide hydrocarbon linker element.

In some embodiments of the composite peptide, the one or more carbon-carbon double bonds present in the intra-peptide hydrocarbon linker are utilized for one or more organic chemical reactions to add one or more additional chemical functionalities. In some embodiments of the composite peptide, the one or more organic chemical reactions comprises an alkene reaction. In some embodiments of the composite peptide, the alkene reaction is selected from the group consisting of hydroboration, oxymercuration, hydration, chlorination, bromination, addition of HF, HBr, HCl or HI, dihydroxylation, epoxidation, hydrogenation, and cyclopropanation. In some embodiments of the composite peptide, one or more additional chemical functionalities can be added subsequent to the alkene reaction wherein the one or more additional chemical functionalities comprise a covalent addition of one or more chemical group substituents, wherein the covalent addition of one or more chemical group substituents comprises nucleophilic reactions with epoxide and hydroxyl groups. In some embodiments of the composite peptide, the one or more additional chemical functionalities are selected from the group consisting of biotin, radioisotopes, therapeutic agents, rapamycin, vinblastine, taxol, non-protein fluorescent chemical groups, FITC, hydrazide, rhodamine, maleimide, protein fluorescent groups, GFP, YFP, and mCherry.

In some embodiments, a pharmaceutical composition is provided. In some embodiments, the pharmaceutical composition comprises a therapeutically effective amount of a peptide conjugate or a derivative thereof, and a pharmaceutically acceptable carrier, diluent, excipient or combination thereof, wherein the peptide conjugate or the derivative thereof modulates the activity of two or more γc-cytokines selected from the group consisting of IL-2, IL-4, IL-7, IL-9, IL-15, and IL-21, wherein the peptide conjugate comprises the amino acid sequence D/E-F-L-E/Q/N-S/R-X-I/K-X-L/I-X-Q (SEQ ID NO: 2), wherein X denotes any amino acid, and wherein the derivative thereof comprises a peptide sequence sharing at least 90% identity with the amino acid sequence of SEQ ID NO: 2.

In some embodiments, a pharmaceutical composition is provided. In some embodiments, the pharmaceutical composition comprises a therapeutically effective amount of a peptide conjugate or a derivative thereof, and a pharmaceutically acceptable carrier, diluent, excipient or combination thereof, wherein the peptide conjugate or the derivative thereof modulates the activity of two or more γc-cytokines selected from the group consisting of IL-2, IL-4, IL-7, IL-9, IL-15, and IL-21, wherein the peptide conjugate comprises the amino acid sequence I-K-E-F-L-Q-R-F-I-H-I-V-Q-S-I-I-N-T-S (SEQ ID NO: 1), and wherein the derivative thereof comprises a peptide sequence sharing at least 90% identity with the amino acid sequence of SEQ ID NO: 1.

In some embodiments, a pharmaceutical composition is provided. In some embodiments, the pharmaceutical composition comprises a therapeutically effective amount of a peptide conjugate or a derivative thereof, and a pharmaceutically acceptable carrier, diluent, excipient or combination thereof, wherein the peptide conjugate or the derivative thereof modulates the activity of two or more γc-cytokines selected from the group consisting of IL-2, IL-4, IL-7, IL-9, IL-15, and IL-21, wherein the peptide conjugate comprises the amino acid sequence I-K-E-F-L-Q-R-F-I-H-I-V-Q-S-I-I-N-T-S (SEQ ID NO: 1), and wherein the derivative thereof comprises a peptide sequence sharing at least 90% identity with the amino acid sequence of SEQ ID NO: 1.

In some embodiments of the pharmaceutical composition, the peptide conjugate or the derivative thereof inhibits the activity of two or more γc-cytokines selected from the group consisting of IL-2, IL-4, IL-7, IL-9, IL-15, and IL-21. In some embodiments of the pharmaceutical composition, the peptide conjugate or the derivative thereof further comprises an additional conjugate at the N termini, C termini or a side residues thereof.

In some embodiments of the pharmaceutical composition, the peptide conjugate or the derivative thereof further comprises a signal peptide. In some embodiments, the pharmaceutical composition further comprises a protein that stabilizes the structure of the peptide conjugate or the derivative thereof and improves its biological activity, wherein the protein is selected from the group consisting of bovine serum albumin (BSA), albumin, Fc region of immunoglobulin G (IgG), biological proteins that function as scaffold, Poly Ethylene Glycol (PEG), and derivatives thereof. In some embodiments of the pharmaceutical composition, the derivative thereof comprises a peptide sequence sharing at least 95% identity with the amino acid sequence of SEQ ID NO: 2. In some embodiments of the pharmaceutical composition, the derivative thereof comprises a peptide sequence sharing at least 95% identity with the amino acid sequence of SEQ ID NO: 1.

In some embodiments, a method of treating an alopecia associated disease is provided. In some embodiments, the method comprises administering a pharmaceutical composition provided herein to a subject in need thereof, wherein the alopecia associated disease is selected from the group consisting of alopecia areata, alopecia totalis, alopecia sub-totalis, alopecia universalis, alopecia diffusa, ophiasis-type alopecia areata, lichen planus, lichen sclerosus, lichen sclerosus et atrophicus, atopy, atopic dermatitis, psoriasis, psoriasis vugaris, psoriasis capitis, psoriasis guttate, psoriasis inversa, psoriatic arthritis, eczema, pemphigus, pemphigus vulgaris, pemphigus foliaceus, pemphigus vegetans, pemphigus erythematosus, mucous membrane pemphigoid, scarring mucous membrane pemphigoid, bullous pemphigoid, myasthenia gravis, thyroid disorders, Hashimoto's thyroiditis, hypothyroidism, endemic goiter, Addison's disease, morphea scleroderma, urticaria, prurigo, rosacea vitiligo, vitiligo, and graft-versus-host disease (GvHD).

In some embodiments, a kit for treating an alopecia associated disease in a patient is provided.

In some embodiments, the kit comprises a pharmaceutical composition, wherein the pharmaceutical composition comprises a therapeutically effective amount of a peptide conjugate, or a derivative thereof, and a pharmaceutically acceptable carrier, diluent, excipient or combination thereof, wherein the peptide conjugate or the derivative thereof modulates the activity of two or more γc-cytokines selected from the group consisting of IL-2, IL-4, IL-7, IL-9, IL-15, and IL-21, wherein the peptide conjugate comprises the amino acid sequence D/E-F-L-E/Q/N-S/R-X-I/K-X-L/I-X-Q (SEQ ID NO: 2), wherein X denotes any amino acid, and wherein the derivative thereof comprises a peptide sequence sharing at least 90% identity with the amino acid sequence of SEQ ID NO: 2.

In some embodiments, the kit comprises a pharmaceutical composition, wherein the pharmaceutical composition comprises a therapeutically effective amount of a peptide conjugate, or a derivative thereof, and a pharmaceutically acceptable carrier, diluent, excipient or combination thereof, wherein the peptide conjugate or the derivative thereof modulates the activity of two or more γc-cytokines selected from the group consisting of IL-2, IL-4, IL-7, IL-9, IL-15, and IL-21, wherein the peptide conjugate comprises the amino acid sequence I-K-E-F-L-Q-R-F-I-H-I-V-Q-S-I-I-N-T-S (SEQ ID NO: 1), and wherein the derivative thereof comprises a peptide sequence sharing at least 90% identity with the amino acid sequence of SEQ ID NO: 1.

In some embodiments, the kit comprises a pharmaceutical composition, wherein the pharmaceutical composition comprises a therapeutically effective amount of a peptide conjugate, or a derivative thereof, and a pharmaceutically acceptable carrier, diluent, excipient or combination thereof, wherein the peptide conjugate or the derivative thereof modulates the activity of two or more γc-cytokines selected from the group consisting of IL-2, IL-4, IL-7, IL-9, IL-15, and IL-21, wherein the peptide conjugate comprises the amino acid sequence I-K-E-F-L-Q-R-F-I-H-I-V-Q-S-I-I-N-T-S (SEQ ID NO: 1), and wherein the derivative thereof comprises a peptide sequence sharing at least 90% identity with the amino acid sequence of SEQ ID NO: 1.

In some embodiments of the kit, the condition is one or more of alopecia areata, alopecia totalis, alopecia subtotalis, alopecia universalis, alopecia diffusa, ophiasis-type alopecia areata, lichen planus, lichen sclerosus, lichen sclerosus et atrophicus, atopy, atopic dermatitis, psoriasis, psoriasis vugaris, psoriasis capitis, psoriasis guttate, psoriasis inversa, psoriatic arthritis, eczema, pemphigus, pemphigus vulgaris, pemphigus foliaceus, pemphigus vegetans, pemphigus erythematosus, mucous membrane pemphigoid, scarring mucous membrane pemphigoid, bullous pemphigoid, myasthenia gravis, thyroid disorders, Hashimoto's thyroiditis, hypothyroidism, endemic goiter, Addison's disease, morphea scleroderma, urticaria, prurigo, rosacea vitiligo, vitiligo, or graft-versus-host disease (GvHD).

Definitions

As used herein, the term "patient" or "subject" refers to the recipient of any of the embodiments of the composite peptides disclosed herein and includes all organisms within the kingdom animalia. In some embodiments, any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, etc.) are included. In preferred embodiments, the animal is within the family of mammals, such as humans, bovine, ovine, porcine, feline, buffalo, canine, goat, equine, donkey, deer, and primates. The most preferred animal is human. In some embodiments, the patient is a male or a female.

As used herein, the term "treat" or any variation thereof (e.g., treatment, treating, etc.), refers to any treatment of a patient diagnosed with a biological condition, such as alopecia areata, alopecia totalis, alopecia subtotalis, alopecia universalis, alopecia diffusa, ophiasis-type alopecia areata, lichen planus, lichen sclerosus, lichen sclerosus et atrophicus, atopy, atopic dermatitis, psoriasis, psoriasis vugaris, psoriasis capitis, psoriasis guttate, psoriasis inversa, psoriatic arthritis, eczema, pemphigus, pemphigus vulgaris, pemphigus foliaceus, pemphigus vegetans, pemphigus erythematosus, mucous membrane pemphigoid, scarring mucous membrane pemphigoid, bullous pemphigoid, myasthenia gravis, thyroid disorders, Hashimoto's thyroiditis, hypothyroidism, endemic goiter, Addison's disease, morphea scleroderma, urticaria, prurigo, rosacea vitiligo, vitiligo, and graft-versus-host disease (GvHD).

The term treat, as used herein, includes: (i) preventing or delaying the presentation of symptoms associated with the biological condition of interest in an at-risk patient who has yet to display symptoms associated with the biological condition; (ii) ameliorating the symptoms associated with the biological condition of interest in a patient diagnosed with the biological condition; (iii) preventing, delaying, or ameliorating the presentation of symptoms associated with complications, conditions, or diseases associated with the biological condition of interest in either an at-risk patient or a patient diagnosed with the biological condition; (iv) slowing, delaying or halting the progression of the biological condition; and/or (v) preventing, delaying, slowing, halting or ameliorating the cellular events of inflammation; and/or (vi) preventing, delaying, slowing, halting or ameliorating the histological abnormalities and/or other clinical measurements of the biological condition.

The term "symptom(s)" as used herein, refers to common signs or indications that a patient is suffering from a specific condition or disease.

The term "effective amount," as used herein, refers to the amount necessary to elicit the desired biological response. In accordance with the present embodiments, an effective amount of a γc-antagonist is the amount necessary to provide an observable effect in at least one biological factor for use in treating a biological condition.

"Recombinant DNA technology" or "recombinant" refers to the use of techniques and processes for producing specific polypeptides from microbial (e.g., bacterial, yeast), invertebrate (insect), mammalian cells or organisms (e.g., transgenic animals or plants) that have been transformed or transfected with cloned or synthetic DNA sequences to enable biosynthesis of heterologous peptides. Native glycosylation pattern will only be achieved with mammalian cell expression system. Prokaryotic expression systems lack the ability to add glycosylation to the synthesized proteins.

Yeast and insect cells provide a unique glycosylation pattern that may be different from the native pattern.

A "nucleotide sequence" refers to a polynucleotide in the form of a separate fragment or as a component of a larger DNA construct that has been derived from DNA or RNA isolated at least once in substantially pure form, free of contaminating endogenous materials and in a quantity or concentration enabling identification, manipulation, and recovery of its component nucleotide sequences by standard molecular biology methods (as outlined in Current Protocols in Molecular Biology).

"Recombinant expression vector" refers to a plasmid comprising a transcriptional unit containing an assembly of (1) a genetic element or elements that have a regulatory role in gene expression including promoters and enhances, (2) a structure or coding sequence that encodes the polypeptide according to the present embodiments, and (3) appropriate transcription and translation initiation sequence and, if desired, termination sequences. Structural elements intended for use in yeast and mammalian system preferably include a signal sequence enabling extracellular secretion of translated polypeptides by yeast or mammalian host cells.

"Recombinant microbial expression system" refers to a substantially homogenous monoculture of suitable hot microorganisms, for example, bacteria such as E. coli, or yeast such as S. cerevisiae, that have stably integrated a recombinant transcriptional unit into chromosomal DNA or carry the recombinant transcriptional unit as a component of a residual plasmid. Generally, host cells constituting a recombinant microbial expression system are the progeny of a single ancestral transformed cell. Recombinant microbial expression systems will express heterologous polypeptides upon induction of the regulatory elements linked to a structural nucleotide sequence to be expressed.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure.

It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

It should be understood, however, that this detailed description, while indicating preferred embodiments of the invention, is given by way of illustration only, since various changes and modifications within the spirit and scope of the invention will become apparent to those skilled in the art.

EXAMPLES

The following Examples are presented for the purposes of illustration and should not be construed as limitations.

Example 1—Method for Assessing the Inhibitory Activity of γc-Antagonist Peptide The capacity of any custom derivative peptide prepared according to the present embodiments for inhibiting the action of one γc-cytokine family member is determined using mammalian cellular assays to measure their proliferative response to the γc-cytokine family member.

For each of the six γc-cytokines, indicator cell lines: NK92, a human NK cell line NK92 available by American Type Culture Collection (ATCC) (catalog #CRL-2407), CTLL-2, a murine CD8 T cells line available from ATCC, and PT-18, a murine mast cell line and its subclone PT-18β, is transfected with human IL-2Rβ gene to make the cells responsive to IL-2 and IL-15 (Tagaya et al., 1996, EMBO J. 15:4928-39), and is used to quantitatively determine the γc-cytokine's growth-promoting activity (See Current protocols in Immunology from Wiley and Sons for a methodological reference). The indicator cells demonstrate semi-linear dose-dependent response when measured by a colorimetric WST-1 assay over a range of concentrations (See Clontech PT3946-1 and associated user manual, incorporated herein by reference, for a detailed description of the reagents and methods).

Once the appropriate doses of the cytokine that yield the 50% and 95% maximum response from the indicator cell line is determined, various concentrations (ranging from 1 pM to 10 μM) of the purified or synthesized custom derivative peptide is added to each well containing the cytokine and indicator cells. The reduction in light absorbance at 450 nm is used as an indicator of inhibition of cytokine-stimulated cellular proliferation. Typically, the cells are stimulated by the cytokines such that the absorbance of the well containing indicator cell line and the cytokine is between 2.0 and 3.0, which is reduced to a range of 0.1 to 0.5 by the addition of inhibitory peptides.

Example 2—the Selective Inhibition of the Growth-Promoting Activities of Certain γc-Cytokines by BNZ-γ

Figure 3A:
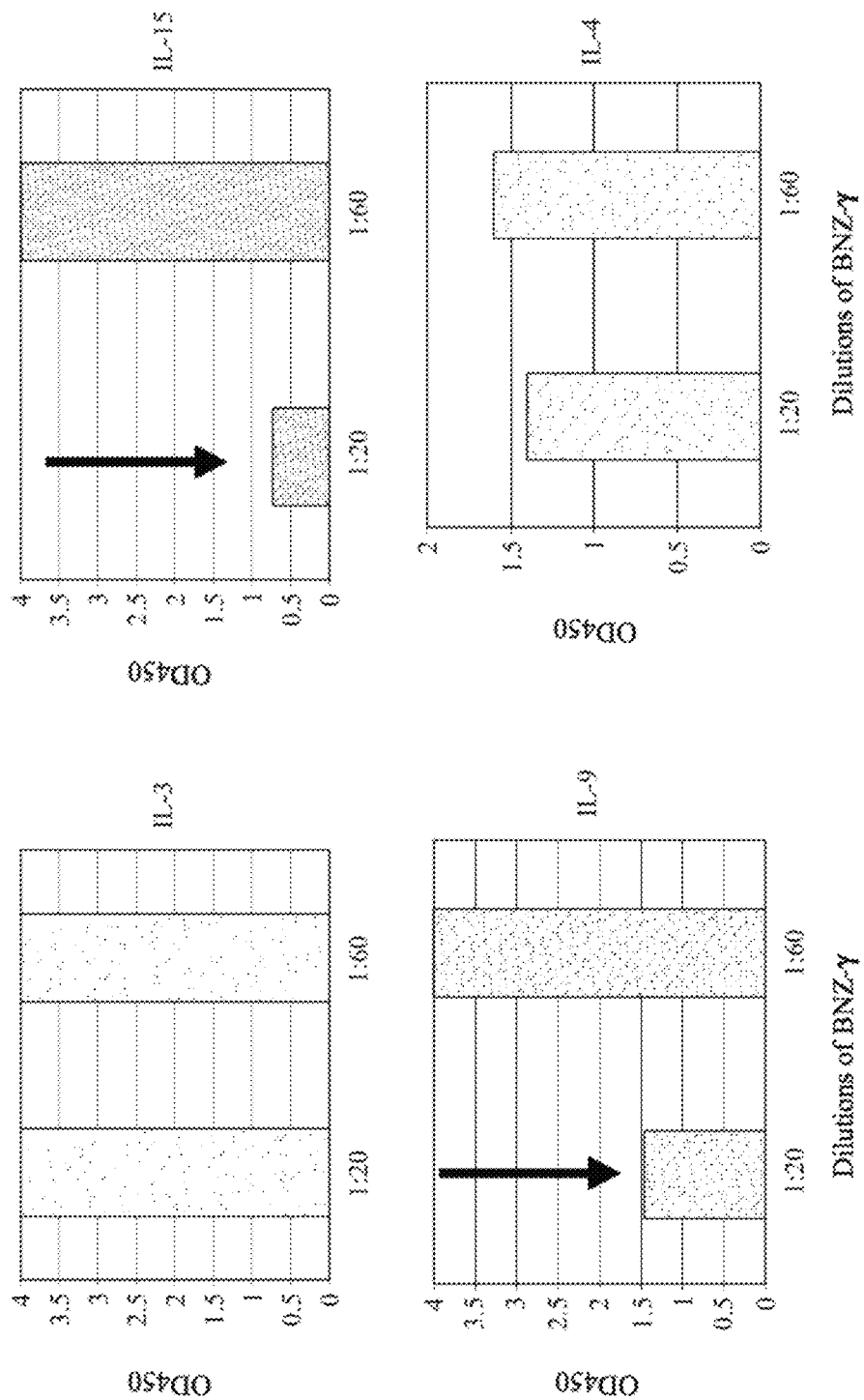
FIG. 3A shows inhibition of IL-15, and IL-9 activity by BNZ-γ in a PT-18 proliferation assay.
Figure 4:
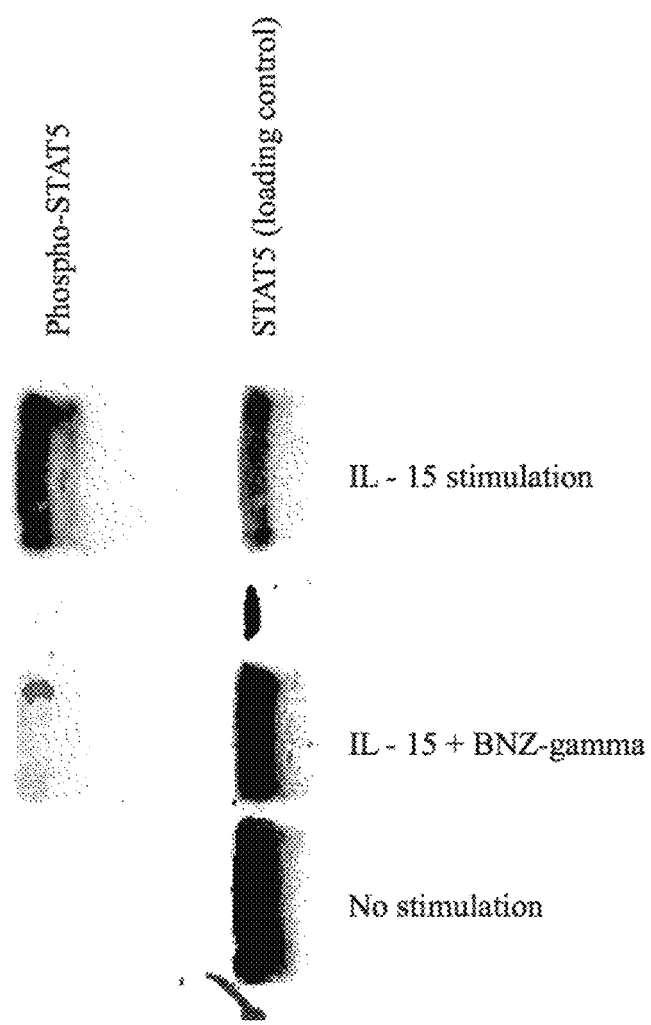
FIG. 4 shows inhibition of IL-15-mediated tyrosine-phosphorylation of STAT5 by BNZ-γ.

Using PT-18β cells as described above, the ability of the BNZ-γ peptide to specifically inhibit the growth-promoting activity of select γc-cytokines was determined (FIG. 3A). IL-3, a non-γc-cytokine that supports the growth of PT-18β cells, was used as a negative control. Briefly, PT-18β cells were incubated either with two different dilutions of BNZ-γ peptide produced by HEK293T cells (1:20 or 1:60 dilution of the original supernatant of HEK293T cells transfected with a BNZ-γ expression construct) or without BNZ-γ peptide in the presence of IL-3, IL-9, IL-15, or IL-4 (1 nM of each cytokine in the culture).

The growth-responses of the cells were determined 2 days after the introduction of BNZ-γ peptide and the cytokine using the WST-1 assay. The growth-promoting activity of IL-3 (a non γc-cytokine) was not inhibited by BNZ-γ. In contrast, the activity of IL-15 and IL-9 were significantly (p<0.01 Student's T test) reduced by the BNZ-γ peptide. Cellular proliferation stimulated by IL-4, another γc-cytokine, was not affected by the by the addition of BNZ-γ peptide. Results for IL-3, IL-9, IL-15, and IL-4 are shown at FIG. 3A.

Figure 3B:
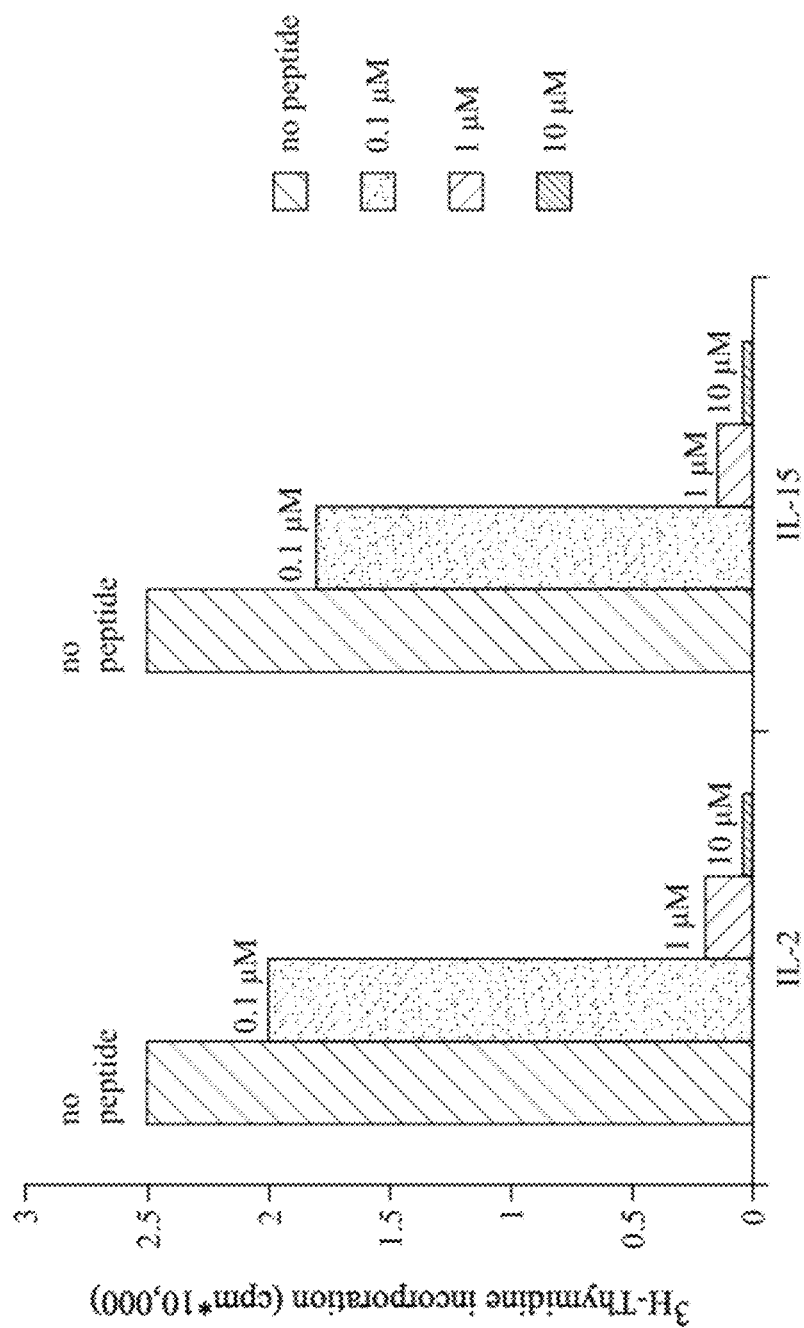
FIG. 3B shows a proliferation assay of CTLL-2 cells grown in the presence of IL-2 or IL-15 and 0, 0.1, 1 or 10 μM BNZ-γ.

In a similar assay, the murine cell line CTTL2 was used. In this assay the cells were cultured with 0.5 nM of recombinant IL-2 in RPMI 10% fetal Calf Serum. To set up the proliferation assay, cells were washed from the cytokines 3 times. Cells were seeded at 1×10(5) cells per well of a 96-well plate with final concentration of 50 pM of IL-2 or IL-15. Various concentration of BNZ-γ peptide (0.1, 1, and 10 µM) was added to each well. Cells were cultured for 20 hours and in the last 4 hours, $^3$H-thymidine was added to the plates. Cells were harvested and radioactivity measured to determine cell proliferation levels. The data are shown in FIG. 3B.

Example 3—Method for Measuring Inhibition γc-Cytokine Activity by Assaying 3H-Thymidine Incorporation of as a Marker of Cellular Proliferation Inhibition of γc-cytokine-induced proliferation of an indicator cell population by antagonist custom derivative peptides is measured by the 3H-thymidine incorporation assay. Briefly, radiolabeled thymidine (1 microCi) is given to 20-50,000 cells undergoing proliferation in the presence of cytokines. The cell-incorporated radioactivity is measured by trapping cell-bound radioactivity to a glass-fiber filter using a conventional harvester machines (Example, Filtermate Universal Harvester from Perkin-Elmer), after which the radioactivity is measured using a b-counter (Example 1450, Trilux microplate scintillation counter).

Example 4—Method for Measuring Inhibition γc-Cytokine Activity by Assaying Incorporation of a Cell-Tracker Dye as a Marker of Cellular Proliferation Indicator cells are incubated in the presence of a selected γc-cytokine or in the presence of a selected γc-cytokine and a selected custom derivative peptide. The cell population is then labeled in vitro using a cell-tracker dye, for example, CMFDA, C2925 from Invitrogen, and the decay of cellular green fluorescence at each cellular division is monitored using a flow-cytometer (for example, Beckton-Dickinson FACScalibur). Typically, in response to γc-cytokine stimulation 7~10 different peaks corresponding to the number of divisions that the cells have undergone will appear on the green fluorescence channel. Incubation of the cells with the selected γc-cytokine and antagonist custom derivative peptide reduces the number of peaks to only 1 to 3, depending on the degree of the inhibition.

Example 5—Inhibition of Intracellular Signaling by Custom Peptide Derivative Antagonists In addition to stimulating cellular proliferation, binding of the γc-cytokines to their receptors causes a diverse array of intracellular events. (Rochman et al. 2009 Nat. Rev. Immunol. 9:480-90, Pesu et al. 2005 Immunol. Rev. 203:127-142.) Immediately after the cytokine binds to its receptor, a tyrosine kinase called Jak3 (Janus-kinase 3) is recruited to the receptor at the plasma membrane. This kinase phosphorylates the tyrosine residues of multiple proteins including the γc-subunit, STAT5 (Signal Transducer and Activator of Transcription 5) and subunits of the PI3 (Phosphatidylinositol 3) kinase. Among these, the phosphorylation of STAT5 has been implicated in many studies as being linked to the proliferation of cells initiated by the γc-cytokine. (Reviewed in Hennighausen and Robinson, 2008 Genes Dev. 22:711-21.) In accordance with these published data, whether or not the BNZ-γ peptide inhibits the tyrosine phosphorylation of STAT5 molecule in PT-18β cells stimulated by IL-15 was examined (results shown in FIG. 4).

PT-18β cells were stimulated by IL-15 in the presence or absence of BNZ-γ peptide. Cytoplasmic proteins were extracted from the cells according to a conventional method as described in Tagaya et al. 1996 EMBO J. 15:4928-39. The extracted cytoplasmic proteins were resolved using a standard SDS-PAGE (Sodium Dodecyl-Sulfate PolyAcrylamide Gel Electrophoresis) and the phosphorylation status was confirmed by an anti-phospho-STAT5 antibody (Cell Signaling Technology, Catalog #9354, Danvers MA) using immunoblotting (See FIG. 4, top panel). To confirm that each lane represented a similar total protein load, the membrane was then stripped, and re-probed with an anti-STAT5 antibody (Cell Signaling Technology, Catalog #9358) (See FIG. 4, bottom panel).

These results demonstrated that tyrosine phosphorylation of STAT5, a marker of signal transduction, was induced by IL-15 in PT-18β cells, and tyrosine phosphorylation of STAT5 was markedly reduced by the BNZ-γ peptide.

Example 6—Rational Design for γc-Antagonist Peptide Derivatives

Derivative peptides are prepared based from the core sequence D/E-F-L-E/Q/N-S/R-X-I/K-X-L/I-X-Q (SEQ ID NO: 2) (where X denotes any amino acid) by substituting the defined amino acids of the core sequence with amino acids having identical physico-chemical properties as designated in FIG. 2.

Alternatively, custom peptides or their derivative peptides can be prepared based on the sequence alignment of the D-helix regions of different γc-cytokine family members.

Example 7—Method of Identifying the Inhibitory Specificity of Antagonistic Custom Derivative Peptides The γc-cytokine inhibitory specificity of antagonistic custom derivative peptides is determined by assaying the ability of a custom derivative peptide to inhibit the proliferative response of a cytokine-responsive cell line to each of the γc-cytokines. For example, a mouse cell line, CTLL-2, is used to determine if a candidate peptide inhibits the function of IL-2 and IL-15. PT-18(β) cells are used to determine if a candidate peptide inhibits the function of IL-4 and IL-9. PT-18 (7α) cells are used to determine if a candidate peptide inhibits the function of IL-7, and PT-18(21α) cells are used to determine if a candidate peptide inhibits the function of IL-21. PT-18(β) denotes a subclone of PT-18 cells that exogenously express human IL-2Rβ by gene transfection (See Tagaya et al. 1996), PT-18(7α) denotes a subclone that expresses human IL-7Rα by gene transfection and PT-18 (21Rα) cells express human IL-21Rα.

Another alternative is to use other cell lines that respond to an array of cytokines. An example of this cell line in a human NK cell line NK92 that is commercially available by ATCC (catalog #CRL-2407). This cell line is an IL-2 dependent cell line that responds to other cytokines including IL-9, IL-7, IL-15, IL-12, IL-18, IL-21 (Gong et al. 1994 Leukemia 8: 652-658, Kingemann et al., 1996, Biol Blood Marrow Transplant 2:68; 75, Hodge D L et al., 2002 J. Immunol. 168:9090-8).

Example 8—Preparation of γc-Antagonist Peptides

Custom derivative γc-antagonist peptides are synthesized chemically by manual and automated processes.

Manual synthesis: Classical liquid-phase synthesis is employed, which involves coupling the carboxyl group or C-terminus of one amino acid to the amino group or N-terminus of another. Alternatively, solid-phase peptide synthesis (SPPS) is utilized.

Automated synthesis: Many commercial companies provide automated peptide synthesis for a cost. These companies use various commercial peptide synthesizers, including synthesizers provided by Applied Biosystems (ABI). Custom derivative γc-antagonist peptides are synthesized by automated peptide synthesizers.

Example 9—Biological Production of Custom Derivative γc-Antagonist Peptides Using Recombinant Technology A custom derivative γc-antagonist peptide is synthesized biologically as a pro-peptide that consists of an appropriate tagging peptide, a signal peptide, or a peptide derived from a known human protein that enhances or stabilizes the structure of the BNZ-γ peptide and improves their biological activities. If desired, an appropriate enzyme-cleavage sequence proceeding to the N-terminus of the peptide shall be designed to remove the tag or any part of the peptide from the final protein.

A nucleotide sequence encoding the custom derivative peptide with a stop codon at the 3' end is inserted into a commercial vector with a tag portion derived from thioredoxin of E. coli and a special peptide sequence that is recognized and digested by an appropriate proteolytic enzyme (for example, enterokinase) intervening between the tag portion and the nucleotide sequence encoding the custom derivative peptide and stop codon. One example of a suitable vector is the pThioHis plasmid available from Invitrogen, CA. Other expression vectors may be used.

Example 10—Conjugation of Custom Peptides and Derivative to Carrier Proteins for Immunization Purposes and Generation of Antibody Against the Custom Peptides BNZ-γ or a derivative thereof are used to immunize animals to obtain polyclonal and monoclonal antibodies. Peptides are conjugated to the N- or the C-terminus of appropriate carrier proteins (for example, bovine serum albumin, Keyhole Limpet Hemocyanin (KLH), etc.) by conventional methods using Glutaraldehyde or m-Maleimidobenzoyl-N-Hydroxysuccinimide Ester. The conjugated peptides in conjunction with an appropriate adjuvant are then used to immunize animals such as rabbits, rodents, or donkeys. The resultant antibodies are examined for specificity using conventional methods. If the resultant antibodies react with the immunogenic peptide, they are then tested for the ability to inhibit individual γc-cytokine activity according to the cellular proliferation assays described in Examples 1-3. Due to the composite nature of the derivative peptides it is possible to generate a single antibody that recognizes two different cytokines simultaneously, because of the composite nature of these peptides.

Example 11—Method for Large Scale Production of Custom Derivative γc-Antagonist Peptides Recombinant proteins are produced in large scale by the use of cell-free system as described elsewhere. (See Takai et al., 2010 Curr. Pharm. Biotechnol. 11(3):272-8.) Briefly, cDNAs encoding the γc-antagonist peptide and a tag are subcloned into an appropriate vector (See Takai et al., 2010 Curr. Pharm. Biotechnol. 11(3):272-8), which is subjected to in vitro transcription, followed immediately by an in vitro translation to produce the tagged peptide. The pro-polypeptide is then purified using an immobilized antibody recognizing the tagged epitope, treated by the proteolytic enzyme and the eluate (which mostly contains the custom derivative peptide of interest) is tested for purity using conventional 18% Tricine-SDS-PAGE (Invitrogen) and conventional comassie staining. Should the desired purity of the peptide not be met (>98%), the mixture is subjected to conventional HPLC (high-performance liquid chromatography) for further purification.

Example 12—Use of Humanized NSG Mouse Model for the Therapeutic Investigation of Immune-mediated Alopecia and Alopecia Associated Disorders A major advancement for the in vivo study of human immunological systems was the development that a functional human immune system can be established in a severely immunodeficient mouse such as an immuno compromised NOD/Scid/Il2rg$^{-/-}$ (NSG) mouse. (Shultz et al., 2012 Nat. Rev. Immunol. 12:786-98.) NSG mice lack a functioning γc-subunit required for γc-cytokine signaling, are extremely deficient in lymphoid cells, and allow for very efficient human immune system engraftment after intraperitoneal administration of Ficoll-gradient purified human peripheral blood mononuclear cells (huPBMCs). The subsequent expansion of human immune cells results in a humanized mouse model of systemic graft versus host disease (GvHD) as the human T cells target murine tissues including the skin (Sonntag et al., 2015 J. Autoimmun. 62:55-66.) The humanized NSG mice develop a progressive hair loss (alopecia) as one symptom of systemic GvHD, with bald patches appearing after about 3-4 weeks, which progress to a complete loss of hair by about day 45-50. Animals die shortly after due to GvHD.

Figure 5:
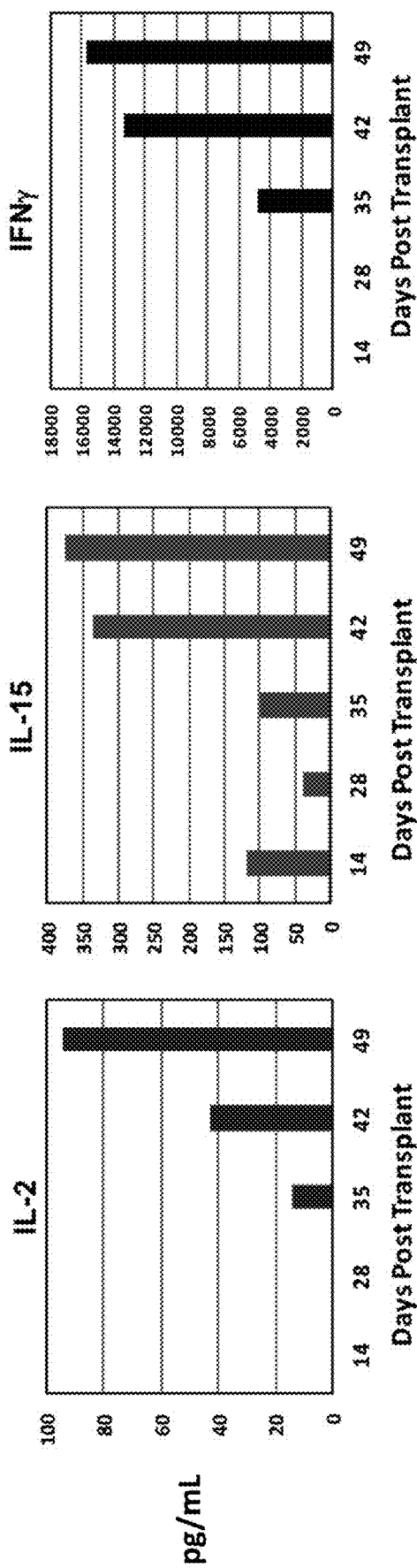
FIG. 5 shows circulating levels of the human cytokines IL-2, IL-15, and IFNγ following huPBMC transplant to NSG mice.

To further understand the mechanisms underlying alopecia in the humanized mouse model, the expression profiles of three key circulating human cytokines (IL-2, IL-15, and IFNγ) were characterized for alopecia following the administration of 2 million huPBMCs intraperitoneally into five 3-week-old NSG mice. Increases in IL-15 were earliest and evident at day 14, while IL-2 and IFNγ were not elevated until day 35, with all three cytokines increasing out to day 49 (results shown in FIG. 5), which was the last time point available due to the death of the mice in the experimental group. This indicates that IL-15 is a key driver of disease. By day 35, mice showed symptoms of GvH responses including loss of body weight and moderate to severe alopecia.

Example 13—Effects of an Anti-Human CD8 Antibody on Humanized NSG Mice with Immune-Mediated Hair Loss Members of the NKG2 family have been implicated in the cytotoxicity process of NK and CD8+ T cells and are regulated by multiple cytokines including the γc-cytokine IL-15 (Borrego et al. 1998 J Exp Med 187:813-18, Brumbaugh et al. 1996 J Immunol 157:2804-12, Cantoni et al. 1998 Eur J Immunol 28:327-38, Mingari et al. 1998 Proc Natl Acad Sci 95:1172-7). Each NKG2 receptor dimerizes with the lectin protein CD94 to form a heterodimeric receptor complex (Lazetic et al. 1996 J Immunol 157:4741-5), except NKG2D which exists as a homodimer (Garrity et al. 2005 Proc Natl Acad Sci 102:7641-6). Previous reports suggest that hair loss in patients with alopecia is mediated by cytotoxic CD8+ T-cells that express the NKG2D receptor (Xing et al. 2014 Nat Med 9:1043-9, Gilhar et al. 2016 Autoimmun. Rev. 15:726-35.) To characterize the importance of CD8+ T-cells in this disease model, animals were treated with the anti-human CD8 antibody (OKT8) (BD Biosciences), which depletes human CD8+ T-cells. Within 4 weeks after transplantation of 2 million huPBMCs, a cohort of five mice developed weight loss and patchy to complete hair loss. Three humanized mice were then selected for treatment with two injections (twice/week) of 50 μg/mouse of the anti-CD8 antibody.

Figure 6A:
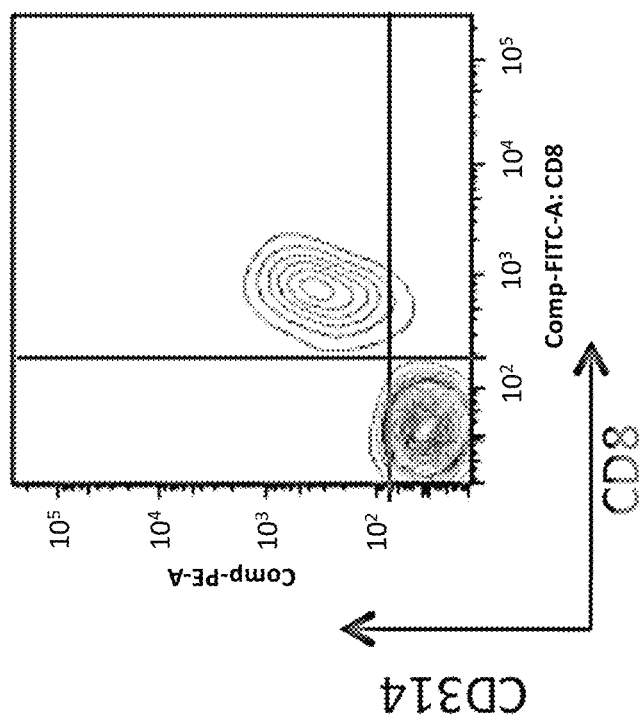
FIG. 6A shows that human CD8+ T-cells from a representative NSG mouse 4-weeks post-huPBMC transplantation fully express NKG2D (CD314).
Figure 6B:
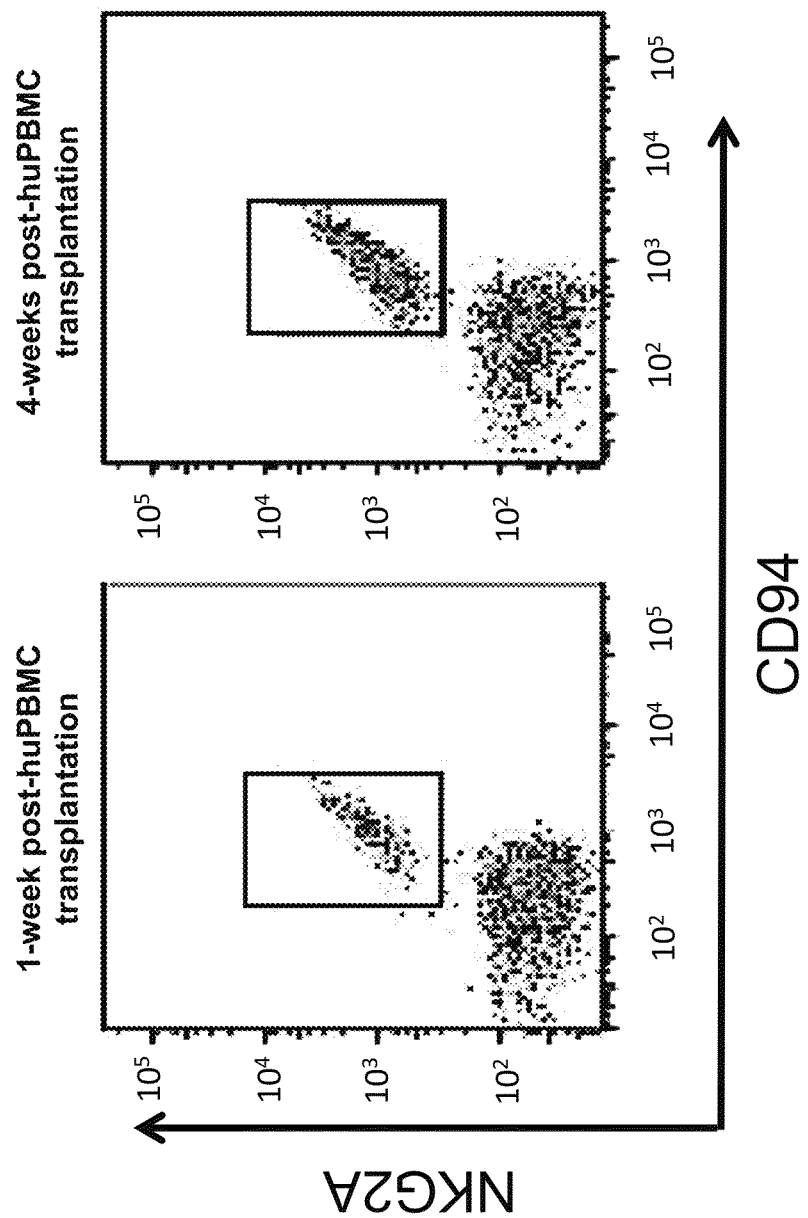
FIG. 6B shows the expansion of NKG2A+ human CD8+ T-cells (boxed) in a representative NSG mouse from 1-week to 4-weeks post-huPBMC transplantation.

Prior to treatment with the anti-human CD8 antibody, human CD8+ T cells were isolated from a blood sample collected from a representative humanized NSG mouse, and stained for the expression of the NKG2D (CD314) receptor, and receptors in the NKG2 family (NKG2A and NKG2C) to facilitate measurement by flow cytometry. The cytotoxic CD8+ T cells in alopecia disease progression have also been characterized as positive for the expression of the activating NKG2D receptor (Xing et al. 2014 Nat Med 9:1043-9.) Flow cytometry showed that almost the entire human CD8+ T-cell population isolated from the humanized NSG mouse was NKG2D+ (see FIG. 6A). Interestingly, whereas it was observed that the human NKG2C+ CD8+ T-cells diminish after huPBMC transplantation, the human NKG2A+ CD8+ T-cells showed a marked increase after huPBMC transplantation that only expanded as GvHD symptoms worsened and the disease progressed (See FIG. 6B).

Figure 7A:
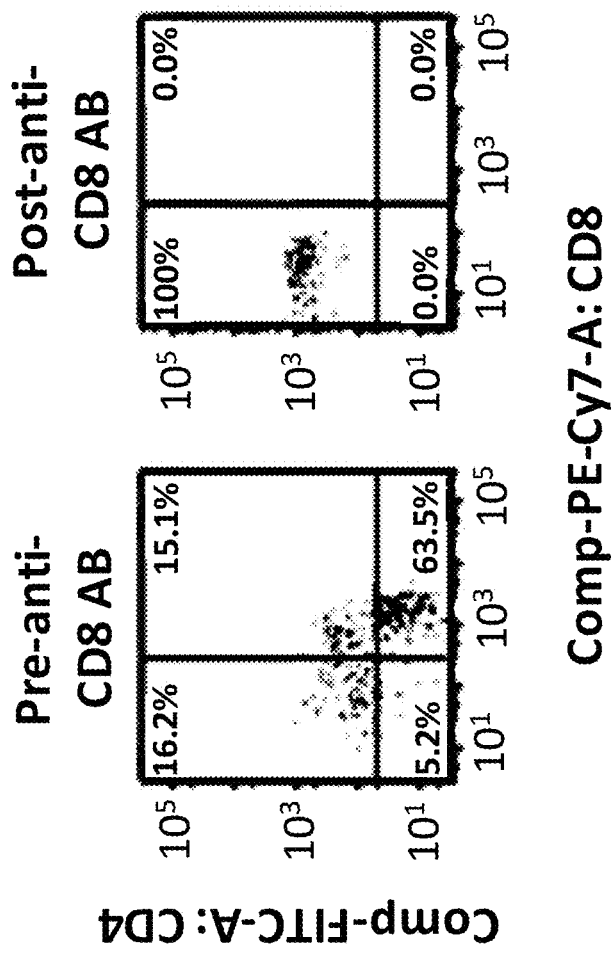
FIG. 7A shows specific depletion of human CD8+ T-cells following injection of an anti-CD8 antibody in a representative NSG mouse that was 4-weeks post-huPBMC transplantation. Post-anti-CD8 AB graph is 8-days post antibody injection.
Figure 7B:
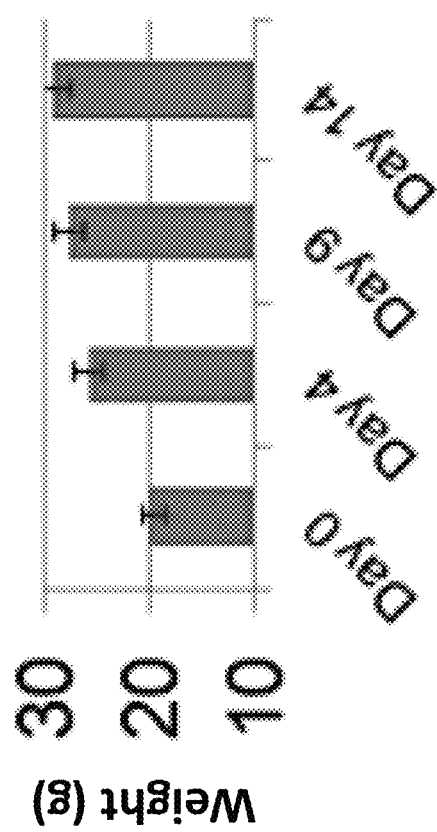
FIG. 7B shows the average recovery of body weight in grams in days following anti-CD8 antibody-mediated human CD8+ T-cell depletion in three NSG mice that were antibody treated at 4-weeks post-huPBMC transplantation.
Figure 7C:
FIG. 7C shows the regrowth of body hair following anti-CD8 antibody-mediated human CD8+ T-cell depletion in a representative NSG mouse 14-days post antibody injection and 42-days post-huPBMC transplantation.

Following treatment with the anti-human CD8 antibody, all human CD8+ T-cells were significantly and specifically depleted (See FIG. 7A), which did not re-emerge post treatment. Within 4 days-post depletion of CD8+ T-cells, all three humanized mice showed weight gain (See FIG. 7B), with re-growth of body hair evident by two weeks-post treatment (see FIG. 7C).

Figure 8:
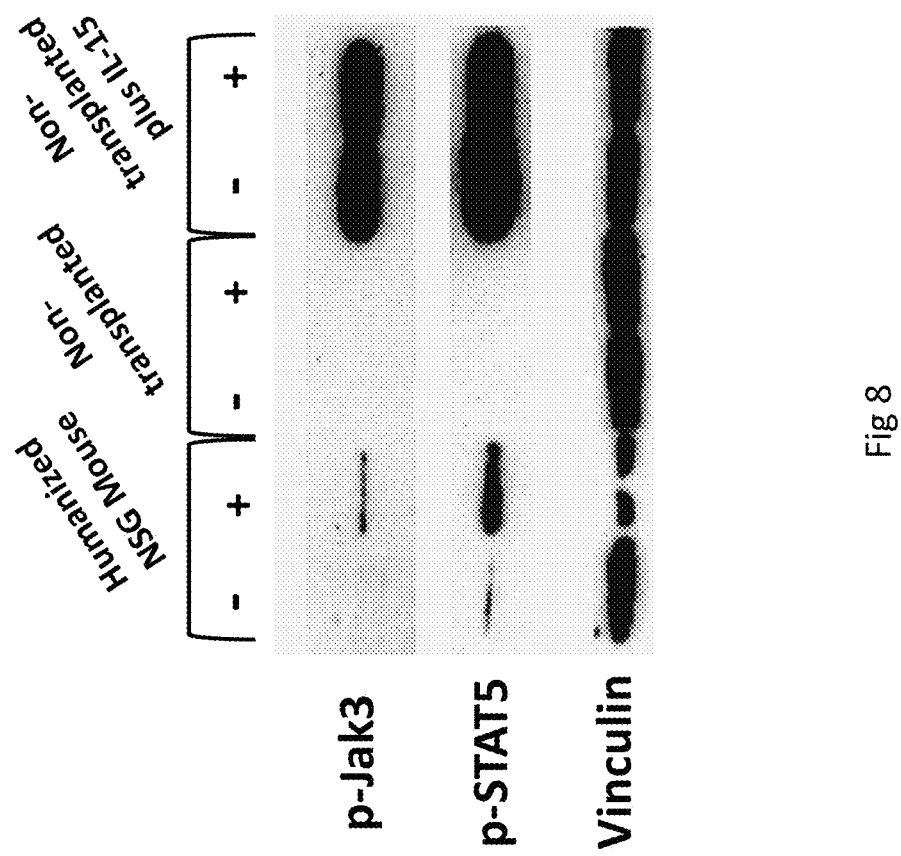
FIG. 8 shows the positive phosphorylation of Jak3 and STAT5 in NKG2A+ (+), but not NKG2A– (–) CD8+ T-cells isolated from representative NSG mouse 4-weeks post-huPBMC transplantation indicative of constitutive activation of γc-cytokine signaling.

Example 14—Constitutive γc-Signaling of Human NKG2A+ CD8+ T-Cells in Humanized NSG Mice with Immune-Mediated Hair Loss The interaction between the γc-subunit and a γc-cytokine leads to the activation and phosphorylation of Jak3. Considering the interaction of the γc-subunit and Jak3 is very specific in that there is no other receptor molecule that recruits Jak3 for signal transduction, it was next tested whether human NKG2A+ CD8+ T-cells isolated from humanized NSG mice 4 weeks after transplantation of 2 million huPBMCs were positive for the phosphorylation of Jak3 and the downstream phosphorylation of STAT5. Human NKG2A+ and NKG2A− CD8+ T-cells were Ficoll-purified from blood and spleen of three representative humanized NSG mice. Cells were then stained by a mixture of FITC-anti-CD4, PE-anti-CD8, and PE/Cy7-anti-NKG2A, and fluorescence-activated cell sorted (FACSAria II, BD Biosciences) into CD4− CD8+ NKG2A+ and CD4− CD8+ NKG2A− subpopulations. As a control, non-transplanted NKG2A+ and NKG2A− CD8+ T-cells were left unstimulated, or stimulated by the addition of IL-15 ex vivo. Cytoplasmic proteins were extracted from the cells according to a conventional method as described in Tagaya et al. 1996 EMBO J. 15:4928-39. The extracted cytoplasmic proteins were resolved using a standard SDS-PAGE (Sodium Dodecyl-Sulfate PolyAcrylamide Gel Electrophoresis) and the phosphorylation status was confirmed by an anti-phospho-Jak3 antibody (Cell Signaling Technology, Catalog #5031, Danvers MA) or an anti-phospho-STAT5 antibody (Cell Signaling Technology, Catalog #9354, Danvers MA) using immunoblotting (see FIG. 8). Vinculin was probed as a control. Results show constitutive γc-signaling of human NKG2A+, but not NKG2A− CD8+ T-cells in humanized NSG mice 4 weeks after transplantation of 2 million huPBMCs.

Example 15—Antibody-Mediated Depletion of Members of the Human C-Type Lectin Receptor NKG2 Family in CD8+ T-Cells on Humanized NSG Mice with Immune-Mediated Hair Loss To test the causative involvement of members of the human C-type lectin receptor NKG2 family (NKG2A, B, C, D, E, F, and H) in CD8+ T-cells in the pathogenesis of systemic GvHD in the humanized NSG mouse, antibody-mediated depletion of each individual human NKG2 protein member in CD8+ T-cells is performed by injecting 50 μg/mouse of the anti-NKG2 antibody specific to the NKG2 protein member under study twice per week in three representative humanized NSG mice at 3- to 5-weeks post-transplantation of 2 million huPBMCs. The successful depletion of the specific NKG2 family member in CD8+ T-cells is then correlated with major systemic GvHD symptoms, such as loss of body weight, immune-mediated hair loss, and circulating levels of the cytokines IL-2, IL-15, and IFNγ.

Figure 9A:
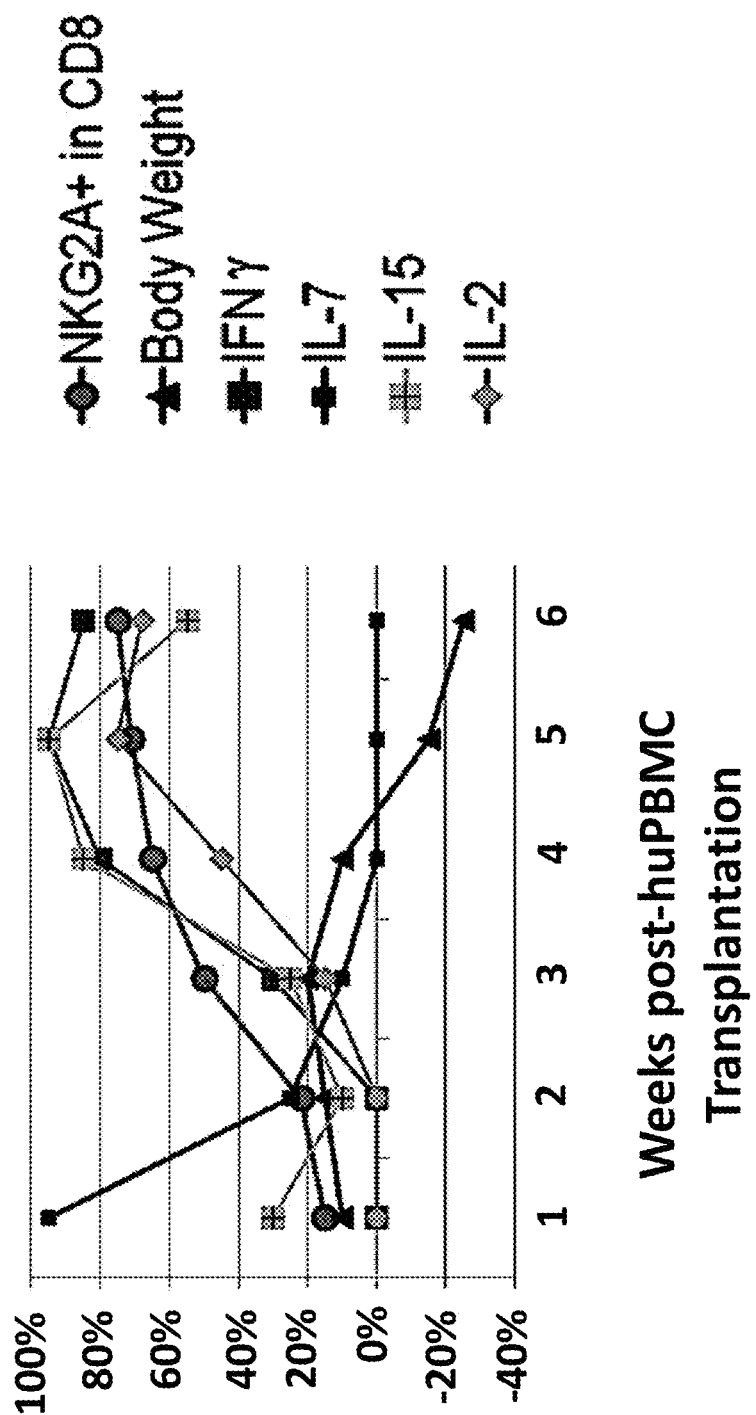
FIG. 9A shows the positive correlation between the expansion of NKG2A+ human CD8+ T-cells and the levels of inflammatory cytokine IFNγ and the γc-cytokines IL-2 and IL-15 from three representative humanized NSG mice over the course of 1-week to 6-weeks post-huPBMC transplantation.

Example 16—Effects of Antibody-Mediated Depletion of Human NKG2A+ CD8+ T-Cells on Humanized NSG Mice with Immune-Mediated Hair Loss To further examine if NKG2A+ CD8+ T-cells are causatively linked to the systemic GvHD symptoms such as loss of body weight and hair loss observed following huPBMC transplantation in NSG mice, a compilation was generated of the kinetics of the expansion of NKG2A+ CD8+ T-cells with those of body weight and the levels of the inflammatory cytokine IFNγ and the γc-cytokines IL-2, IL-7, and IL-15 weekly from three representative humanized NSG mice 1-week to 6-weeks post-transplantation of 2 million huPBMCs. A clear correlation was observed between the increase of NKG2A+ cells in the CD8+ T-cell compartment with an increase of IL-2, IL-15, and IFNγ (see FIG. 9A).

Figure 9B:
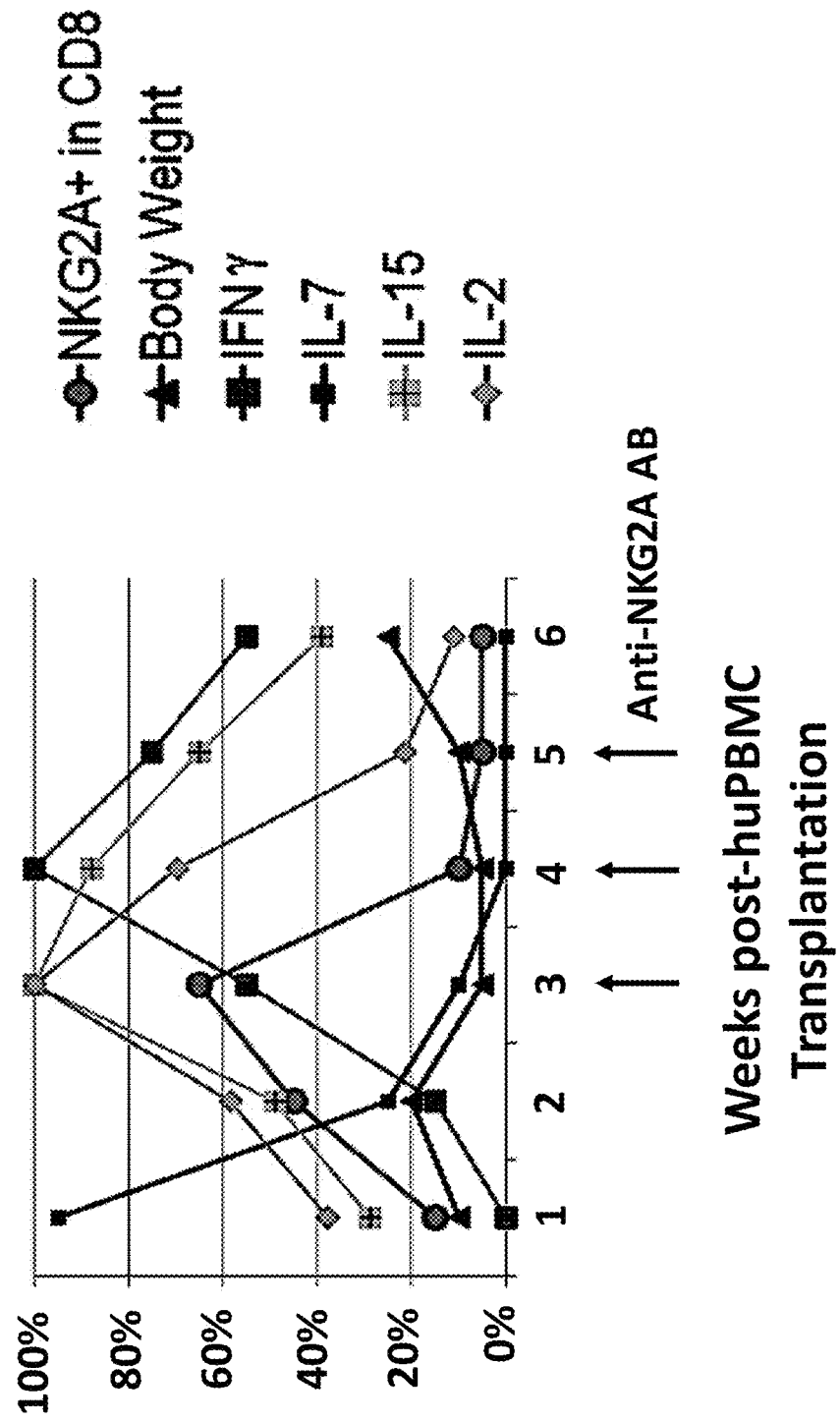
FIG. 9B shows the effective depletion of human NKG2A+ CD8+ T-cells via administration of an anti-NKG2A antibody twice per week in three representative humanized NSG mice at 3- to 5-weeks post-huPBMC transplantation results in an improvement of GvHD symptoms such as loss in body weight, and a significant reduction of the γc-cytokines IL-2, IL-15, and the inflammatory cytokine IFNγ.

To test the causative involvement of NKG2A+ CD8+ T-cells in the pathogenesis of systemic GvHD in the humanized NSG mouse, antibody-mediated depletion of human NKG2A+ CD8+ T-cells was performed by injecting 50 μg/mouse of an anti-NKG2A antibody (R & D Systems, Catalog #MAB1059, Clone 131411, Minneapolis, MN) twice per week in three representative humanized NSG mice at 3- to 5-weeks post-transplantation of 2 million huPBMCs. The successful depletion of NKG2A+ CD8+ T-cells (See FIG. 9B, weeks 4-6 post-huPBMC transplantation) was positively associated with the mitigation of major systemic GvHD symptoms, with the loss of body weight and immune-mediated hair loss improving after the first week of anti- NKG2A antibody treatment. It was observed that a decrease of IL-2, IL-15, and IFNγ directly correlated with the antibody-mediated depletion of human NKG2A+ CD8+ T-cells (see FIG. 9B).

Example 17—Effects of BNZ-γ on Humanized NSG Mice with Immune-Mediated Hair Loss To test the effects of BNZ-γ, five humanized NSG mice were allowed to develop extensive GvHD with widespread hair loss prior to initiating treatment (approximately 4-weeks post 2 million huPBMC transplant). At the start of twice weekly intravenous (IV) treatment with a PEGylated BNZ-γ (Day 0, 2 mg/kg) for 2 weeks, all animals appeared very sick. Control PBS-treated animals died within approximately 1-2 weeks. By day 21, BNZ-γ-treated animals gained significant weight, had healthier-looking skin, and visible regrowth of their fur coat. The effect of BNZ-γ continued ~2 weeks after completing the two-week treatment, with the BNZ-γ-treated animals showing significant regrowth of their fur (results shown in FIG. 10A). In support of the clinical observations, BNZ-γ resulted in a statistically significant reduction in the levels of circulating inflammatory cytokines (IL-6 and IFNγ), back to/towards the normal physiological range in the NSG mouse following completion of the twice weekly BNZ-γ dosing regimen for a treatment duration of two weeks (see FIG. 10B).

Example 18—Comparison of BNZ-γ, Anti-IL-2 Antibody, Anti-IL-15 Antibody, and Combination Anti-IL-2 and Anti-IL-15 Antibody Treatment on Survival, Immune-Mediated Hair Loss and Cytokine Levels in Humanized NSG Mice In this experiment, NSG mice were transplanted with 2 million huPBMCs on study day 0, with therapeutic treatment beginning 35-days post-transplant. Mice were treated twice weekly with IV injections of PBS control (n=5), BNZ-γ at 2 mg/kg (n=5), anti-IL-2 antibody at 5 mg/kg (n=3), anti-IL-15 antibody at 5 mg/kg (n=3), or combination anti-IL-2 and anti-IL-15 antibody each at 5 mg/kg (n=3) starting on day 35 for a treatment duration of 4 weeks. PBS control mice began dying shortly after treatment initiation, while the single antibody-treated animals began to die after treatment was stopped, which was not statistically different from untreated controls (p>0.05). The combination of anti-IL-2 and anti-IL-15 antibodies was significantly more effective as compared to single antibody treatment (p=0.014) with a survival benefit that lasted several weeks after cessation of treatment, but was less effective than BNZ-γ (p=0.001) (results shown in FIG. 11A).

At the beginning of treatment on post-transplant day 35, mice had significant hair loss. Approximately two weeks after treatment was completed (~day 63), there was a noticeable improvement in the regrowth of hair in animals treated with the anti-IL-15 antibody, which appeared to be more effective as compared to the anti-IL-2 antibody. The combination antibody treatment did not appear significantly different for hair regrowth as compared to the anti-IL-15 antibody alone. However, the BNZ-γ-treated mice appeared to have the greatest degree of hair regrowth of all 4 treatment groups, which suggests that blockade of IL-9 may be important to achieve the maximum therapeutic response. (results shown in FIG. 11B).

Levels of IL-6 and IFNγ were also measured in this experiment. Both inflammatory cytokines showed significant elevations in the PBS control NSG mice. All 4 active treatments reduced the levels of each cytokine to varying degrees, with BNZ-γ and the combination antibody being most effective. These data are consistent with previous reports that IFNγ is a downstream cytokine regulated by IL-15, with IL-15 blockade shutting down IFNγ expression (Fehniger et al. 2000 J. Immunol. 164:1643-7). Cytokine levels were determined using sera collected on day 50, except for one animal in the anti-IL-2 antibody treatment group (collected on day 45), one mouse in the PBS control untreated group (collected on day 45), and two mice from the PBS control untreated group (collected on day 40) to ensure a blood sample was collected before each became fatally ill. (results shown in FIG. 11C).

Example 19—Immunohistochemistry of Humanized NSG Mouse Skin Tissue Treated with BNZ-γ

In order to characterize the nature of immune attack in the skin tissue and around the hair follicles, immunohistochemistry studies were conducted of the skin tissue of humanized NSG mice 3-weeks (pre-BNZ-γ) and 7-weeks (with or without BNZ-γ treatment) after transplantation of 2 million huPBMCs. The tissue was fixed for 24 hours in 4% formalin (Sigma) and then moved to 70% ethanol for at least 24 hours before being processed. Tissue was then embedded in paraffin following dehydration for two washes of two hours each in 70%, 90%, and 100% ethanol, then cleared in xylene twice for two hours each, and infiltrated with melted paraplast plus at 60 C two times for two hours. Paraffin embedded tissues were stored at room temperature prior to sectioning and staining. An anti-human CD8 antibody (BioCare Medical CRM 311C) or isotype control was used for staining of the tissues based on the standard procedure for IHC.

An influx of human CD8 T cells in the skin tissue of humanized NSG mice at 3-weeks post-transplant was observed. CD8 T cells remained at comparable levels at 7-weeks post-transplant without BNZ-γ treatment. However, at 7-weeks post-transplant with BNZ-γ treatment, a significant reduction in the number of infiltrated CD8 cells was observed. The data are shown in FIG. 12.

Example 20—Method of Treating Alopecia in a Human Patient by Administration of a Therapeutic Compound A human patient suffering from alopecia (alopecia areata, alopecia totalis, alopecia subtotalis, alopecia universalis, alopecia diffusa, ophiasis-type alopecia areata) is identified. An effective dose, as determined by the physician, of a therapeutic compound, for example, an anti-CD8 antibody, anti-IL-2 antibody, anti-IL-15 antibody, anti-NKG2A antibody, a custom derivative γc-antagonist peptide, for example, a composite peptide comprising the sequence of BNZ-γ, or a derivative thereof, or a combination of said therapeutic compounds is administered to the patient for a period of time determined by the physician. Treatment is determined to be effective if patient's symptoms improve or if the progression of the disease has been stopped or slowed down.

Example 21—Method of Treating Vitiligo in a Human Patient by Administration of a Therapeutic Compound A human patient suffering from vitiligo (vitiligo and rosacea vitiligo) is identified. An effective dose, as determined by the physician, of a therapeutic compound, for example, an anti-CD8 antibody, anti-IL-2 antibody, anti-IL-15 antibody, anti-NKG2A antibody, a custom derivative γc-antagonist peptide, for example, a composite peptide comprising the sequence of BNZ-γ, or a derivative thereof, or a combination of said therapeutic compounds is administered to the patient for a period of time determined by the physician. Treatment is determined to be effective if patient's symptoms improve or if the progression of the disease has been stopped or slowed down.

Example 22—Method of Treating Psoriasis in a Human Patient by Administration of a Therapeutic Compound A human patient suffering from psoriasis (psoriasis, psoriasis vugaris, psoriasis capitis, psoriasis guttate, psoriasis inversa, psoriatic arthritis) is identified. An effective dose, as determined by the physician, of a therapeutic compound, for example, an anti-CD8 antibody, anti-IL-2 antibody, anti-IL-15 antibody, anti-NKG2A antibody, a custom derivative γc-antagonist peptide, for example, a composite peptide comprising the sequence of BNZ-γ, or a derivative thereof, or a combination of said therapeutic compounds is administered to the patient for a period of time determined by the physician. Treatment is determined to be effective if patient's symptoms improve or if the progression of the disease has been stopped or slowed down.

Example 23—Method of Treating Pemphigus in a Human Patient by Administration of a Therapeutic Compound A human patient suffering from pemphigus (pemphigus, pemphigus vulgaris, pemphigus foliaceus, pemphigus vegetans, pemphigus erythematosus) is identified. An effective dose, as determined by the physician, of a therapeutic compound, for example, an anti-CD8 antibody, anti-IL-2 antibody, anti-IL-15 antibody, anti-NKG2A antibody, a custom derivative γc-antagonist peptide, for example, a composite peptide comprising the sequence of BNZ-γ, or a derivative thereof, or a combination of said therapeutic compounds is administered to the patient for a period of time determined by the physician. Treatment is determined to be effective if patient's symptoms improve or if the progression of the disease has been stopped or slowed down.

Example 24—Method of Treating Pemphigoid in a Human Patient by Administration of a Therapeutic Compound A human patient suffering from pemphigoid (mucous membrane pemphigoid, scarring mucous membrane pemphigoid, bullous pemphigoid) is identified. An effective dose, as determined by the physician, of a therapeutic compound, for example, an anti-CD8 antibody, anti-IL-2 antibody, anti-IL-15 antibody, anti-NKG2A antibody, a custom derivative γc-antagonist peptide, for example, a composite peptide comprising the sequence of BNZ-γ, or a derivative thereof, or a combination of said therapeutic compounds is administered to the patient for a period of time determined by the physician. Treatment is determined to be effective if patient's symptoms improve or if the progression of the disease has been stopped or slowed down.

Example 25—Method of Treating GvHD in a Human Patient by Administration of a Therapeutic Compound A human patient suffering from GvHD is identified. An effective dose, as determined by the physician, of a therapeutic compound, for example, an anti-CD8 antibody, anti-IL-2 antibody, anti-IL-15 antibody, anti-NKG2A antibody, a custom derivative γc-antagonist peptide, for example, a composite peptide comprising the sequence of BNZ-γ, or a derivative thereof, or a combination of said therapeutic compounds is administered to the patient for a period of time determined by the physician. Treatment is determined to be effective if patient's symptoms improve or if the progression of the disease has been stopped or slowed down.

REFERENCES

All references disclosed herein as well as listed below are incorporated by reference in their entireties.

Antony, P. A., Paulos, C. M., Ahmadzadeh, M., Akpinarli, A., Palmer, D. C., Sato, N., Kaiser A., Heinrichs, C. S., Klebanoff, C. A., Tagaya, Y., and Restifo, N P., Interleukin-2-dependent mechanisms of tolerance and immunity in vivo. 2006 J. Immunol. 176:5255-66.

Atwa M. A., Youssef N., Bayoumy N. M. T-helper cytokines (interleukins 17, 21, 22, and 6, and tumor necrosis factor-a) in patients with alopecia areata: association with clinical type and severity. 2016 Int J Dermatol 55:666-72.

Awwad, S. and Angkawinitwong, U., Overview of Antibody Drug Delivery. 2018 Pharmaceutics 10:83.

Azimi, N., Nagai, M., Jacobson, S., Waldmann, T. A., IL-15 plays a major role in the persistence of Tax-specific CD8 cells in HAM/TSP patients. 2001 Proc. Natl. Acad. Sci. 98:14559-64.

Azimi, N., Mariner J., Jacobson S., Waldmann T. A., How does interleukin 15 contribute to the pathogenesis of HTLV type-1 associated myelopathy/tropical spastic paraparesis? 2000 AIDS Res. Hum. Retroviruses 16:1717-22.

Azimi, N., Jacobson, S., Leist, T., Waldmann, T. A., Involvement of IL-15 in the pathogenesis of human T lymphotropic virus type-I-associated myelopathy/tropical spastic paraparesis: implications for therapy with a monoclonal antibody directed to the IL-2/15R beta receptor. 1999 J. Immunol. 163:4064-72.

Azimi, N., Brown, K., Bamford, R. N., Tagaya, Y., Siebenlist, U., Waldmann, T. A., Human T cell lymphotropic virus type I Tax protein trans-activates interleukin 15 gene transcription through an NF-kappaB site. 1998 Proc. Natl. Acad. Sci. USA 95:2452-7.

Bazan, J. F., Hematopoietic receptors and helical cytokines. 1990 Immunol. Today 11:350-354.

Bettini, M., and Vignali, D. A., Regulatory T cells and inhibitory cytokines in autoimmunity. 2009 Curr. Opin. Immunol. 21:612-8.

Blaser, B. W., Roychowdhury, S, Kim, D. J., Schwind, N. R., Bhatt, D., Yuan, W., Kusewitt, D. F., Ferketich, A. K., Caligiuri, M. A., Guimond, M., Donor-derived IL-15 is critical for acute allogeneic graft-versus-host disease. 2005 Blood 105:894-901.

Blažek, D. and Celer, V. The production and application of single-chain antibody fragments. 2003 Folia Microbiol 48:687-98.

Bodd, M., Raki, M., Tollefsen, S., Fallang, L. E., Bergseng, E., Lundin, K. E., Sollid, L. M., HLA-DQ2-restricted gluten-reactive T cells produce IL-21 but not IL-17 or IL-22. 2010 Mucosal Immunol. 3:594-601.

Borrego, F. Ulbrecht, M., Weiss, E. H., Coligan, J. E., Brooks, A. G., Recognition of human histocompatibility leukocyte antigen (HLA)-E complexed with HLA class I signal sequence-derived peptides by CD94/NKG2 confers protection from natural killer cell-mediated lysis. 1998 J Exp Med 187:813-18.

Botti, E., Spallone, G., Caruso, R. Monteleone, G., Chimenti, S., Costanzo, A. Psoriasis, from pathogenesis to therapeutic strategies: IL-21 as a novel potential thereapeutic target. 2012 Curr. Pharm. Biotechnol. 13:1861-1867.

Brumbaugh, K. M., Perez-Villar, J. J., Dick, C. J., Schoon, R. A., Lopez-Botet, M., Leibson, P. J. Clonotypic differences in signaling from CD94 (kp43) on NK cells lead to divergent cellular responses. 1996 J Immunol 157:2804-12.

Bucher, C., Koch, L., Vogtenhuber, C., Goren, E., Munger, M., Panoskaltsis-Mortari, A., Sivakumar, P., Blazar, B. R. IL-21 blockade reduces graft-versus-host disease mortality by supporting inducible T regulatory cell generation. 2009 114:5375-84.

Cantoni, C., Biassoni, R., Pende, D. et al., The activating form of CD94 receptor complex: CD94 covalently associates with the Kp39 protein that represents the product of the NKG2-C gene. 1998 Eur J Immunol 28:327-38.

Caruso, R., Costanzo, A., Monteleone, G. Pathogenic role of interleukin-21 in psoriasis. 2009 Cell Cycle 8:3629-3630.

Caruso, R., Bott, E., Sarra, M., Esposito, M., Stolfi, C., Diluvio, L., Giustizieri, M. L., Pacciani, V., Mazzotta, A., Campione, E. et al. Involvement of interleukin-21 in the epidermal hyperplasia of psoriasis. 2009 Nat. Med. 15:1013-1015.

Chik, K. W., Li, K., Pong, H., Shing, M. M., Li, C. K., Yuen, P. M. Elevated serum interleukin-15 level in acute graft-versus-host disease after hematopoietic cell transplantation. 2003 J Pediatr Hematol Oncol. 25:960-4.

Cox, K. L., Devanarayan, V., Kriauciunas, A., Montrose, C., and Sittampalam, S. "Immunoassay methods", in Assay Guidance Manual [Internet], 2004 eds G. S. Sittampalam, N. P. Coussens, H. Nelson, et al. (Bethesda, MD: Eli Lilly & Company and the National Center for Advancing Translational Sciences).

D'Auria, L., Bonifati, C., Cordiali-Fei, P., Leone, G., Picardo, M., Pietravalle, M., Giacalone, B., Ameglio, F., Increased serum interleukin-15 levels in bullous skin diseases: correlation with disease intensity. 1999 Arch. Dermatol. Res. 291:354-356.

De Rezende, L. C., Silva I. V., Rangel, L. B., Guimaraes, M. C., Regulatory T cells as a target for cancer therapy. 2010 Arch. Immunol. Ther. Exp. 58:179-90.

Dubois, S., Mariner, J., Waldmann, T. A., Tagaya, Y., IL-15Ralpha recycles and presents IL-15 In trans to neighboring cells. 2002 Immunity 17:537-47.

Dodge D L. Et al., IL-2 and IL-12 alter NK cell responsiveness to IFN-gamma-inducible protein 10 by down-regulating CXCR3 expression. J. Immun. 168:6090-8.

Fang J., Hu, C., Hong, M., Wu, Q., You, Y., Zhong, Z., Li, W., Zou, P., Hu, Y., Prophylactic effects of interleukin-2 receptor antagonists against graft-versus-host disease following unrelated donor peripheral blood stem cell transplantation. 2012 Biol Blood Marrow Transplant. 18:754-62.

Fehniger, T. A., Yu, H., Cooper, M. A., Suzuki, K., Shah, M. H., Caligiuri, M. A. IL-15 costimulates the generalized Shwartzman reaction and innate IFN-gamma production in vivo. 2000 J. Immunol. 164:1643-1647.

Fehniger, T. A., Suzuki, K., Ponnappan, A., VanDeusen, J. B., Cooper, M. A., Florea, S. M., Freud, A. G., Robinson, M. L., Durbin, J., Caligiuri, M. A., Fatal leukemia in interleukin 15 transgenic mice follows early expansions in natural killer and memory phenotype CD8+ T cells. 2001 J. Exp. Med. 193:219-31.

Fisher, A. G., Burdet, C., LeMeur, M., Haasner, D., Gerber, P., Cerediq, R., Lymphoproliferative disorders in an IL-7 transgenic mouse line. 1993 Leukemia 2:S66-68.

Frenzel, A., Kugler, J., Helmsing, S., Meier, D., Schirrmann, T., Hust, M., and Dübel, S. Designing Human Antibodies by Phage Display. 2017 Transfus Med Hemother 44:312-18.

Fuentes-Duculan, J., Gulati, N., Bonifacio, K. M., Kunjravia, N., Zheng, X., Suarez-Farinas, M., Shemer, A., Guttman-Yassky, E., Krueger, J. G., Biomarkers of alopecia areata disease activity and response to corticosteroid treatment. 2016 Exp Dermatol 4:282-6.

Garrity, D., Call, M. E., Feng, J., Wucherpfennig, K. W., The activating NKG2D receptor assembles in the membrane with two signaling dimers into a hexameric structure. 2005 Proc Natl Acad Sci 102:7641-6.

Gilhar, A., Schrum, A. G., Etzioni, A., Waldmann, H., Paus, R. Alopecia areata animal models illuminate autoimmune pathogenesis and novel immunotherapeutic strategies. 2016 Autoimmun. Rev. 15:726-735.

Gong J. H. et al. Characterization of a human cell line (NK-92) with phenotypical and functional characteristics of activated natural killer cells. Leukemia 8: 652-658, 1994.

Grando S. A., Glukhenky, B. T., Drannik, G. N., Epshtein, E. V., Kostromin, A. P., Korostash, T. A., Mediators of inflammation in blister fluids from patients with pemphigus vulgaris and bullous pemphigoid. 1989 Arch. Dermatol. 125:925-930.

Guo-Qiang, B., and Xian-Li, H. Guided selection methods through chain shuffling. 2009 Methods Mol Biol 562:133-42.

Hammers, C. M. and Stanley, J. R. Antibody Phage Display: Technique and Applications. 2014 J Invest Dermatol 134:e17.

He, Z., Jin, L., Liu, Z. F., Hu., L., Dang, E. L., Feng, Z. Z., Li, Q. J., Wang, G. Elevated serum levels of interleukin 21 are associated with disease severity in patients with psoriasis. 2012 Br. J. Dermatol. 167:191-193.

Hennighausen, L., Robinson, G. W., Interpretation of cytokine signaling through the transcription factors STAT5A and STAT5B. 2008 Genes Dev. 22:711-21.

Hippen, K. L., Bucher, C., Schirm, D. K., Bearl, A. M., Brender, T., Mink, K. A., Waggie, K. S., Peffault de Latour, R., Janin, A., Curtsinger, J. M. et al. Blocking IL-21 signaling ameliorates xenogeneic GVHD induced by human lymphocytes. 2012 Blood 119:619-28.

Jagielska D., Redler S., Brockschmidt F. F., Herold C., Pasternack S. M., Garcia Bartels N., Hanneken S., Eigelshoven S., Refke M., Barth S., et al. Follow-up study of the first genome-wide association scan in alopecia areata: IL13 and KIAA0350 as susceptibility loci supported with genome-wide significance. 2012 J Invest Dermatol 132:2192-7.

Jespers, L. S., Roberts, A., Mahler, S. M., Winter, G., and Hoogenboom, H. R. Guiding the selection of human antibodies from phage display repertoires to a single epitope of an antigen. 1994 Biotechnology 12:899-903.

Jespersen, M. C., Peters, B., Nielsen, M., and Marcatili, P. BepiPred-2.0: improving sequence-based B-cell epitope prediction using conformational epitopes. 2017 Nucleic Acids Res 45:W24-W29.

Klingemann H G, et al. A cytotoxic NK-cell line (NK-92) for ex vivo purging of leukemia from blood. Biol. Blood Marrow Transplant. 2: 68-75, 1996.

Köhler, G. and Milstein, C. Continuous cultures of fused cells secreting antibody of predefined specificity. 1975 Nature 256:495-7.

Kooy-Winkelaar, Y. M, Bouwer, D., Janssen, G. M., Thompson, A., Brugman, M. H., Schmitz, F., de Ru, A. H., van Gils, T., Bouma, G., van Rood, J. J. et al. CD4 T-cell cytokines synergize to induce proliferation of malignant and nonmalignant intraepithelial lymphocytes. 2017 Proc Natl Acad Sci USA 114: E980-9.

Kozbor, D. and Roder, J. C. The production of monoclonal antibodies from human lymphocytes. 1983 Immunol Today 4:72-9.

Kozbor, D., Lagarde, A., and Roder, J. C. Human hybridomas constructed with antigen-specific, EBV-transformed cell lines. 1982 Proc Natl Acad Sci 79:6651-55.

Krause, C. D. and Pestka, S., Evolution of the Class 2 cytokines and receptors, and discovery of new friends and relatives. 2005 Pharmacol. and Therapeutics 106:299-346.

Kundig, T. M., Schorle, H., Bachmann, M. F., Hengartener, H., Zinkernagel, R. M., Horak, I., Immune Responses of the interleukin-2-deficient mice. 1993 Science 262:1059-61.

Laffleur, B., Pascal, V., Sirac, C., and Cogné, M. Production of human or humanized antibodies in mice. 2012 Methods Mol Biol 901:149-59.

Lazetic, S., Chang, C., Houchins, J. P., Lanier, L. L., Phillips, J. H., Human natural killer cell receptors involved in MEW class I recognition are disulfide-linked heterodimers of CD94 and NKG2 subunits. 1996 J Immunol 157:4741-5.

Le Buanec, H., Paturance, S., Couillin, I., Schnyder-Candrian, S., Larcier, P., Ryffel, B., Bizzini, B., Bensussan, A., Burny, A., Gallo, R., Zagury, D., Peltre, G., Control of allergic reactions in mice by an active anti-murine IL-4 immunization. 2007 Vaccine 25:7206-16.

Littman, D. R., Rudensky, A Y., Th17 and regulatory T cells in mediating and restraining inflammation. 2010 Cell 140(6):845-58.

Lonberg, N. and Huszar, D. Human antibodies from transgenic mice. 1995 Int Rev Immunol 13:65-93.

Mingari, M. C., Ponte, M., Bertone, S. et al. HLA class I-specific inhibitory receptors in human T lymphocytes: interleukin 15-induced expression of CD94/NK62A in superantigen- or alloantigen-activated CD8+ T cells. 1998 Proc Natl Acad Sci 95:1172-7.

Miyagawa, F., Tagaya, Y., Kim, B. S., Patel, H. J., Ishida, K., Ohteki, T., Waldmann, T. A., Katz, S. I., IL-15 serves as a costimulator in determining the activity of autoreactive CD8 T cells in an experimental mouse model of graft-versus-host-like disease. 2008 J. Immunol. 181:1109-19.

Noguchi, M., Yi, H., Rosenblatt, H. M., Filipovich, A. H., Adelstein, S., Modi, W. S., McBride, O. W., Leonard, W. J., Interleukin 2 receptor gamma chain mutation results in X-linked severe combined immunodeficiency in humans. 1993 Cell 73:147-157.

OH, U., Jacobson S., Treatment of HTLV-I-Associated Myelopathy/Tropical Spastic

Padlan, E. A. A possible procedure for reducing the immunogenicity of antibody variable domains while preserving their ligand-binding properties. 1991 Mol Immunol 28:489-98.

Paraparesis: Towards Rational Targeted Therapy 2008 Neurol Clin. 2008 26: 781-785.

Orzaez, M., Gortat, A., Mondragon, L., Perez-Paya, E., Peptides and Peptide Mimics as Modulators of Apototic Pathways. 2009 Chem. Med. Chem. 4:146-160.

O'Shea, J. J., Targeting the Jak/STAT pathway for immunosuppression. 2004 Ann. Rheum. Dis. 63:(suppl II): ii67-71.

Paul, W. E., Pleiotropy and redundancy: T cell-derived lymphokines in the immune response. 1989 Cell 57:521-4.

Pesu M, Candotti F, Husa M, Hofmann S R, Notarangelo L D, and O'Shea J J. Jak3, severe combined immunodeficiency, and a new class of immunosuppressive drugs. 2005 Immunol. Rev. 203:127-142.

Pesu, M., Laurence, A., Kishore, N., Zwillich, S., Chan, G., O'Shea, J. J., Therapeutic targeting of Janus kinases. Immunol. 2008 Rev. 223:132-142.

Petukhova L., Duvic M., Hordinsky M., Norris D., Price V., Shimomura Y., Kim H., Singh P., Lee A., Chen W. V. et al. Genome-wide association study in alopecia areata implicates both innate and adaptive immunity. 2010 Nature 466:113-7.

Richmond J. M., Strassner J. P., Zapata L. Jr., Garg M., Riding R. L., Refat M. A., Fan X., Azzolino V., Tovar-Garza A., Tsurushita N. et al. Antibody blockade of IL-15 signaling has the potential to durably reverse vitiligo. Sci. Transl. Med. 2018 10:450.

Riechmann, L., Clark, M., Waldmann, H., and Winter, G. Reshaping human antibodies for therapy. 1988 Nature 332:323-7.

Rochman, Y., Spolski, R., Leonard, W. J., New Insights into the regulation of T cells by gamma c family cytokines. 2009 Nat. Rev. Immunol. 9:480-90.

Roguska, M. A., Pedersen, J. T., Keddy, C. A., Henry, A. H., Searle, S. J., Lambert, J. M., Goldmacher, V. S., Blättler, W. A., Rees, A. R., and Guild, B. C. Humanization of murine monoclonal antibodies through variable domain resurfacing. 1994 Proc Natl Acad Sci 91:969-73.

Saha, S. and Raghava, G. P. Prediction of continuous B-cell epitopes in an antigen using recurrent neural network. 2006 Proteins 65:40-8.

Sakaguchi, S., Yamaguchi, T., Nomura, T., Ono, M., Regulatory T cells and immune tolerance. 2008 Cell 133: 775-87.

Sato, N., Sabzevari, H., Fu, S., Ju, W., Bamford, R. N., Waldmann, T. A., and Tagaya, Y., Development of an IL-15-Autocrine CD8 T-cell Leukemia in IL-15 Transgenic mice requires the cis-expression of IL-15R alpha. 2011 117:4032-4040.

Schaller, J., Giese, T., Ladusch, M., Haustein, U. F., Interleukin-2 receptor expression and interleukin-2 production in bullous pemphigoid. 1990 Arch. Dermatol. Res. 282: 223-226.

Shultz, L. D., Brehm, M. A., Garcia-Martinez, J. V., Greiner, D. L., Humanized mice for immune system investigation: progress, promise and challenges. 2012 12:786-798.

Sonntag, K., Eckert, F., Welker, C., Müller, H., Müller, F., Zips, D., Sipos, B., Klein, R., Blank, G., Feuchtinger, T. et al. Chronic graft-versus-host-disease in CD34(+)-humanized NSG mice is associated with human susceptibility HLA haplotypes for autoimmune diseases. 2015 J. Autoimmun. 62:55-66.

Studnicka, G. M., Soares, S., Better, M., Williams, R. E., Nadell, R., and Horwitz, A. H. Human-engineered monoclonal antibodies retain full specific binding activity by preserving non-CDR complementarity-modulating residues. 1994 Protein Eng 7:805-14.

Suarez-Farinas, M., Ungar, B., Noda, S., Shroff, A., Mansouri, Y., Fuentes-Duculan, J., Czernik, A., Zheng, X., Estrada, Y. D., Xu, H. et al. Alopecia areata profiling shows TH1, TH2, and IL-23 cytokine activation without parallel TH17/TH22 skewing. 2015 J. Allergy Clin. Immunol. 136:1277-1287.

Sugamura, K., Asao, H., Kondo, M., Tanaka, N., Ishii, N., Nakamura, M., Takeshita, T., The common gamma-chain for multiple cytokine receptors. 1995 Adv. Immunol. 59: 225-277.

Sugamura, K., Asao, H., Kondo, M., Tanaka, N., Ishii, N., Ohbo, K., Nakamura, M., Takeshita, T., The interleukin-2 receptor gamma chain: its role in the multiple cytokine receptor complexes and T cell development in XSCID. 1996 Annu. Rev. Immunol. 14:179-205.

Sushama S., Dixit N., Gautam R. K., Arora P., Khurana A., Anubhuti A., Cytokine profile (IL-2, IL-6, IL-17, IL-22, and TNF-alpha) in vitiligo-New insight into pathogenesis of disease. 2018 J. Cosmet. Dermatol. 00:1-5.

Tagaya, Y., Burton, J. D., Miyamoto, Y., Waldmann, T A., Identification of a novel receptor/signal transduction pathway for IL-15/T in mast cells. 1996 EMBO J. 15:4928-39.

Tagaya, Y., Memory CD8 T cells now join "Club 21". 2010 J. Leuk. Biol. 87:13-15.

Takai, K., Sawasaki, T., and Endo. Y. The Wheat-Germ Cell-Free Expression System, 2010 Curr. Pharm. Biotechnol. 11:272-8.

Tanaka, T., et al., A novel monoclonal antibody against murine IL-2 receptor beta-chain. Characterization of receptor expression in normal lymphoid cells and EL-4 cells. 1991 J. Immunol. 147:2222-2228.

Takeshita, T., Asao, H., Ohtani, K., Ishii, N., Kumaki, S., Tanaka, N., Manukata, H., Nakamura, M., Sugamura, K., Cloning of the Gamma chain of the Human IL2 receptor. 1992 Science 257:379-382.

Tomimatsu, K. and Shirahata, S. Antigen-specific in vitro immunization: a source for human monoclonal antibodies. 2014 Methods Mol Biol 1060:297-307.

Vaughan, T. J., Williams, A. J., Pritchard, K., Osbourn, J. K., Pope, A. R., Earnshaw, J. C., McCafferty, J., Hodits, R. A., Wilton, J., and Johnson, K. S. Human Antibodies with Sub-nanomolar Affinities Isolated from a Large Non-immunized Phage Display Library. 1996 Nature 14:309-14.

Villadsen, L. S., Schuurman, J., Beurskens, F., Dam, T. N., Dagnaes-Hansen, F., Skov, L., Rygaard, J., Voorhorst-Ogink, M. M., Gerritsen, A. F., van Dijk, M. A., et al., Resolution of psoriasis upon blockade of IL-15 biological activity in a xenograft mouse model. 2003 J. Clin. Invest. 112:1571-1580.

Waldmann, T. A., Anti-Tac (daclizumab, Zenapax) in the treatment of leukemia, autoimmune diseases, and in the prevention of allograft rejection: a 25-year personal odyssey. 2007 J. Clin. Immunol. 27: 1-18.

Waldmann T. A. The biology of IL-15: implications for cancer therapy and the treatment of autoimmune disorders. 2013 J Investig Dermatol Symp Proc 16: S28-30.

Williams, D. G., Matthews, D. J., and Jones, T. "Humanising Antibodies by CDR Grafting.", in: Antibody Engineering, 2010 eds R. Kontermann and S. Dübel (Berlin, Heidelberg: Springer).

Xing L., Dai Z., Jabbari A., Cerise J. E., Higgins C. A., Gong W., de Jong A., Harel S., DeStefano G. M., Rothman L. et al. Alopecia areata is driven by cytotoxic T lymphocytes and is reversed by JAK inhibition. 2014 Nat Med 9:1043-9.

Yao, B., Zhang, L., Liang, S., and Zhang, C. SVMTriP: A Method to Predict Antigenic Epitopes Using Support Vector Machine to Integrate Tri-Peptide Similarity and Propensity. 2012 PLoS One 7:e45152.

What is claimed is:

1. A method of inhibiting, ameliorating, reducing a severity of, or treating at least one alopecia related disorder, the method comprising:
administering a composition comprising a pharmaceutically acceptable carrier and a γc cytokine antagonist peptide comprising a sequence comprising amino acids of γc box D-helix regions of at least two interleukin (IL) protein wherein the γc cytokine antagonist peptide comprises a core γc-box amino acid sequence that is 11 amino acids in length wherein the γc cytokine antagonist peptide comprises the sequence of SEQ ID NO: 1, wherein the γc cytokine antagonist peptide is administered in an amount sufficient to inhibit signaling by IL-2, IL-9, and/or IL-15, and/or decrease circulating levels of IL-6 and/or IFNγ to a subject in need thereof, thereby inhibiting, ameliorating, reducing a severity of, or treating alopecia and/or immune-mediated hair loss.

2. The method of claim 1, wherein the γc cytokine antagonist peptide consists of the sequence of SEQ ID NO: 1.

3. The method of claim 1, wherein the γc cytokine antagonist peptide comprises 19 to 50 amino acids.

4. The method of claim 1, wherein the γc cytokine antagonist peptide further comprises a conjugate at the N-termini, C-termini, side residues, or a combination thereof.

5. The method of claim 4, wherein the conjugate comprises one or more additional moieties selected from the group consisting of bovine serum albumin (BSA), albumin, Keyhole Limpet Hemocyanin (KLH), Fc region of IgG, an antibody against a cell-specific antigen, a receptor, a ligand, a metal ion, and Poly Ethylene Glycol (PEG).

6. The method of claim 1, wherein the γc cytokine antagonist peptide further comprises a hydrocarbon linker element.

7. The method of claim 1, wherein the composition is formulated for topical, oral, or parenteral delivery.

* * * * *

```
                        SEQUENCE LISTING

<160> NUMBER OF SEQ ID NOS: 46

<210> SEQ ID NO 1
<211> LENGTH: 19
<212> TYPE: PRT
<213> ORGANISM: Artificial
<220> FEATURE:
<223> OTHER INFORMATION: Synthetic

<400> SEQUENCE: 1

Ile Lys Glu Phe Leu Gln Arg Phe Ile His Ile Val Gln Ser Ile Ile
1               5                   10                  15

Asn Thr Ser

<210> SEQ ID NO 2
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = D or E
<220> FEATURE:
<221> NAME/KEY: MISC_FEATURE
<222> LOCATION: (4)..(4)
<223> OTHER INFORMATION: X = E or Q or N
<220> FEATURE:
<221> NAME/KEY: MISC_FEATURE
```

```
<222> LOCATION: (5)..(5)
<223> OTHER INFORMATION: X = S or R
<220> FEATURE:
<221> NAME/KEY: MISC_FEATURE
<222> LOCATION: (6)..(6)
<223> OTHER INFORMATION: X = Any amino acid
<220> FEATURE:
<221> NAME/KEY: MISC_FEATURE
<222> LOCATION: (7)..(7)
<223> OTHER INFORMATION: X = I or K
<220> FEATURE:
<221> NAME/KEY: MISC_FEATURE
<222> LOCATION: (8)..(8)
<223> OTHER INFORMATION: X = Any amino acid
<220> FEATURE:
<221> NAME/KEY: MISC_FEATURE
<222> LOCATION: (9)..(9)
<223> OTHER INFORMATION: X = L or I
<220> FEATURE:
<221> NAME/KEY: MISC_FEATURE
<222> LOCATION: (10)..(10)
<223> OTHER INFORMATION: X = Any amino acid

<400> SEQUENCE: 2

Xaa Phe Leu Xaa Xaa Xaa Xaa Xaa Xaa Gln
1               5                   10

<210> SEQ ID NO 3
<211> LENGTH: 19
<212> TYPE: PRT
<213> ORGANISM: Artificial
<220> FEATURE:
<223> OTHER INFORMATION: Synthetic

<400> SEQUENCE: 3

Ile Lys Glu Phe Leu Gln Ser Phe Val His Ile Val Gln Met Phe Ile
1               5                   10                  15

Asn Thr Ser

<210> SEQ ID NO 4
<211> LENGTH: 20
<212> TYPE: PRT
<213> ORGANISM: Artificial
<220> FEATURE:
<223> OTHER INFORMATION: Synthetic

<400> SEQUENCE: 4

Ile Val Glu Phe Leu Asn Arg Trp Ile Thr Phe Cys Gln Ser Ile Ile
1               5                   10                  15

Ser Thr Leu Thr
            20

<210> SEQ ID NO 5
<211> LENGTH: 21
<212> TYPE: PRT
<213> ORGANISM: Artificial
<220> FEATURE:
<223> OTHER INFORMATION: Synthetic

<400> SEQUENCE: 5

Pro Lys Glu Phe Leu Glu Arg Phe Lys Ser Leu Leu Gln Lys Met Ile
1               5                   10                  15

His Gln His Leu Ser
            20

<210> SEQ ID NO 6
<211> LENGTH: 21
<212> TYPE: PRT
```

```
<213> ORGANISM: Artificial
<220> FEATURE:
<223> OTHER INFORMATION: Synthetic

<400> SEQUENCE: 6

Leu Glu Asn Phe Leu Glu Arg Leu Lys Thr Ile Met Arg Glu Lys Tyr
1               5                   10                  15

Ser Lys Cys Ser Ser
            20

<210> SEQ ID NO 7
<211> LENGTH: 21
<212> TYPE: PRT
<213> ORGANISM: Artificial
<220> FEATURE:
<223> OTHER INFORMATION: Synthetic

<400> SEQUENCE: 7

Ala Leu Thr Phe Leu Glu Ser Leu Leu Glu Leu Phe Gln Lys Glu Lys
1               5                   10                  15

Met Arg Gly Met Arg
            20

<210> SEQ ID NO 8
<211> LENGTH: 20
<212> TYPE: PRT
<213> ORGANISM: Artificial
<220> FEATURE:
<223> OTHER INFORMATION: Synthetic

<400> SEQUENCE: 8

Asp Leu Cys Phe Leu Lys Arg Leu Leu Gln Glu Ile Lys Thr Cys Trp
1               5                   10                  15

Asn Lys Ile Leu
            20

<210> SEQ ID NO 9
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
<222> LOCATION: (3)..(3)
<223> OTHER INFORMATION: X = D or E
<220> FEATURE:
<221> NAME/KEY: MISC_FEATURE
<222> LOCATION: (6)..(6)
<223> OTHER INFORMATION: X = E or Q or N or polar amino acid
<220> FEATURE:
<221> NAME/KEY: MISC_FEATURE
<222> LOCATION: (7)..(7)
<223> OTHER INFORMATION: X = S or R or polar amino acid
<220> FEATURE:
<221> NAME/KEY: MISC_FEATURE
<222> LOCATION: (8)..(8)
<223> OTHER INFORMATION: X = Non-polar amino acid
<220> FEATURE:
<221> NAME/KEY: MISC_FEATURE
<222> LOCATION: (9)..(9)
<223> OTHER INFORMATION: X = I or K or non-polar amino acid
```

```
<220> FEATURE:
<221> NAME/KEY: MISC_FEATURE
<222> LOCATION: (10)..(10)
<223> OTHER INFORMATION: X = Any amino acid
<220> FEATURE:
<221> NAME/KEY: MISC_FEATURE
<222> LOCATION: (11)..(11)
<223> OTHER INFORMATION: X = L or I or aliphatic amino acid
<220> FEATURE:
<221> NAME/KEY: MISC_FEATURE
<222> LOCATION: (12)..(12)
<223> OTHER INFORMATION: X = Non-polar amino acid
<220> FEATURE:
<221> NAME/KEY: MISC_FEATURE
<222> LOCATION: (14)..(14)
<223> OTHER INFORMATION: X = Charged amino acid
<220> FEATURE:
<221> NAME/KEY: MISC_FEATURE
<222> LOCATION: (15)..(15)
<223> OTHER INFORMATION: X = Any amino acid
<220> FEATURE:
<221> NAME/KEY: MISC_FEATURE
<222> LOCATION: (16)..(16)
<223> OTHER INFORMATION: X = I or K
<220> FEATURE:
<221> NAME/KEY: MISC_FEATURE
<222> LOCATION: (17)..(17)
<223> OTHER INFORMATION: X = Any amino acid
<220> FEATURE:
<221> NAME/KEY: MISC_FEATURE
<222> LOCATION: (18)..(18)
<223> OTHER INFORMATION: X = Any amino acid
<220> FEATURE:
<221> NAME/KEY: MISC_FEATURE
<222> LOCATION: (19)..(19)
<223> OTHER INFORMATION: X = Any amino acid

<400> SEQUENCE: 9

Xaa Xaa Xaa Phe Leu Xaa Xaa Xaa Xaa Xaa Xaa Xaa Gln Xaa Xaa Xaa
1               5                   10                  15

Xaa Xaa Xaa

<210> SEQ ID NO 10
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
<222> LOCATION: (3)..(3)
<223> OTHER INFORMATION: X = D or E
<220> FEATURE:
<221> NAME/KEY: MISC_FEATURE
<222> LOCATION: (6)..(6)
<223> OTHER INFORMATION: X = E or Q or N or polar amino acid
<220> FEATURE:
<221> NAME/KEY: MISC_FEATURE
<222> LOCATION: (7)..(7)
<223> OTHER INFORMATION: X = S or R or polar amino acid
<220> FEATURE:
<221> NAME/KEY: MISC_FEATURE
<222> LOCATION: (8)..(8)
<223> OTHER INFORMATION: X = Non-polar amino acid
<220> FEATURE:
<221> NAME/KEY: MISC_FEATURE
<222> LOCATION: (9)..(9)
<223> OTHER INFORMATION: X = I or K or non-polar amino acid
```

```
<220> FEATURE:
<221> NAME/KEY: MISC_FEATURE
<222> LOCATION: (10)..(10)
<223> OTHER INFORMATION: X = Any amino acid
<220> FEATURE:
<221> NAME/KEY: MISC_FEATURE
<222> LOCATION: (11)..(11)
<223> OTHER INFORMATION: X = L or I or aliphatic amino acid
<220> FEATURE:
<221> NAME/KEY: MISC_FEATURE
<222> LOCATION: (12)..(12)
<223> OTHER INFORMATION: X = Non-polar amino acid
<220> FEATURE:
<221> NAME/KEY: MISC_FEATURE
<222> LOCATION: (14)..(14)
<223> OTHER INFORMATION: X = Charged amino acid
<220> FEATURE:
<221> NAME/KEY: MISC_FEATURE
<222> LOCATION: (15)..(15)
<223> OTHER INFORMATION: X = Any amino acid
<220> FEATURE:
<221> NAME/KEY: MISC_FEATURE
<222> LOCATION: (17)..(17)
<223> OTHER INFORMATION: X = Any amino acid

<400> SEQUENCE: 10

Xaa Xaa Xaa Phe Leu Xaa Xaa Xaa Xaa Xaa Xaa Xaa Gln Xaa Xaa Ile
1               5                   10                  15

Xaa Thr Ser

<210> SEQ ID NO 11
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
<222> LOCATION: (5)..(5)
<223> OTHER INFORMATION: S-pentenylalanine; Linked to S-pentenylalanine
      at position 1

<400> SEQUENCE: 11

Ala Ile Lys Glu Ala Leu Gln Arg Phe Ile His Ile Val Gln Ser Ile
1               5                   10                  15

Ile Asn Thr Ser
            20

<210> SEQ ID NO 12
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: S-pentenylalanine; Linked to S-pentenylalanine
      at position 12
<220> FEATURE:
<221> NAME/KEY: MISC_FEATURE
<222> LOCATION: (12)..(12)
<223> OTHER INFORMATION: S-pentenylalanine; Linked to S-pentenylalanine
      at position 8

<400> SEQUENCE: 12

Ile Lys Glu Phe Leu Gln Arg Ala Ile His Ile Ala Gln Ser Ile Ile
```

```
1               5                   10                  15

Asn Thr Ser

<210> SEQ ID NO 13
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: R-octenylalanine; Linked to S-pentenylalanine
      at position 15
<220> FEATURE:
<221> NAME/KEY: MISC_FEATURE
<222> LOCATION: (15)..(15)
<223> OTHER INFORMATION: S-pentenylalanine; Linked to R-octenylalanine
      at position 8

<400> SEQUENCE: 13

Ile Lys Glu Phe Leu Gln Arg Ala Ile His Ile Val Gln Ser Ala Ile
1               5                   10                  15

Asn Thr Ser

<210> SEQ ID NO 14
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: S-pentenylalanine; Linked to S-pentenylalanine
      at position 16
<220> FEATURE:
<221> NAME/KEY: MISC_FEATURE
<222> LOCATION: (16)..(16)
<223> OTHER INFORMATION: S-pentenylalanine; Linked to S-pentenylalanine
      at position 12

<400> SEQUENCE: 14

Ile Lys Glu Phe Leu Gln Arg Phe Ile His Ile Ala Gln Ser Ile Ala
1               5                   10                  15

Asn Thr Ser

<210> SEQ ID NO 15
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: R-octenylalanine; Linked to S-pentenylalanine
      at position 19
<220> FEATURE:
<221> NAME/KEY: MISC_FEATURE
<222> LOCATION: (19)..(19)
<223> OTHER INFORMATION: S-pentenylalanine; Linked to R-octenylalanine
      at position 12

<400> SEQUENCE: 15

Ile Lys Glu Phe Leu Gln Arg Phe Ile His Ile Ala Gln Ser Ile Ile
1               5                   10                  15

Asn Thr Ala
```

```
<210> SEQ ID NO 16
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
<222> LOCATION: (5)..(5)
<223> OTHER INFORMATION: S-pentenylalanine; Linked to S-pentenylalanine
      at position 1
<220> FEATURE:
<221> NAME/KEY: MISC_FEATURE
<222> LOCATION: (9)..(9)
<223> OTHER INFORMATION: S-pentenylalanine; Linked to S-pentenylalanine
      at position 13
<220> FEATURE:
<221> NAME/KEY: MISC_FEATURE
<222> LOCATION: (13)..(13)
<223> OTHER INFORMATION: S-pentenylalanine; Linked to S-pentenylalanine
      at position 9

<400> SEQUENCE: 16

Ala Ile Lys Glu Ala Leu Gln Arg Ala Ile His Ile Ala Gln Ser Ile
1               5                   10                  15

Ile Asn Thr Ser
            20

<210> SEQ ID NO 17
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
<222> LOCATION: (5)..(5)
<223> OTHER INFORMATION: S-pentenylalanine; Linked to S-pentenylalanine
      at position 1
<220> FEATURE:
<221> NAME/KEY: MISC_FEATURE
<222> LOCATION: (9)..(9)
<223> OTHER INFORMATION: R-octenylalanine; Linked to S-pentenylalanine
      at position 16
<220> FEATURE:
<221> NAME/KEY: MISC_FEATURE
<222> LOCATION: (16)..(16)
<223> OTHER INFORMATION: S-pentenylalanine; Linked to R-octenylalanine
      at position 8

<400> SEQUENCE: 17

Ala Ile Lys Glu Ala Leu Gln Arg Ala Ile His Ile Val Gln Ser Ala
1               5                   10                  15

Ile Asn Thr Ser
            20

<210> SEQ ID NO 18
<211> LENGTH: 20
<212> TYPE: PRT
<213> ORGANISM: Artificial
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
<222> LOCATION: (5)..(5)
<223> OTHER INFORMATION: S-pentenylalanine; Linked to S-pentenylalanine
      at position 1
<220> FEATURE:
<221> NAME/KEY: MISC_FEATURE
<222> LOCATION: (13)..(13)
<223> OTHER INFORMATION: S-pentenylalanine; Linked to S-pentenylalanine
      at position 17
<220> FEATURE:
<221> NAME/KEY: MISC_FEATURE
<222> LOCATION: (17)..(17)
<223> OTHER INFORMATION: S-pentenylalanine; Linked to S-pentenylalanine
      at position 13

<400> SEQUENCE: 18

Ala Ile Lys Glu Ala Leu Gln Arg Phe Ile His Ile Ala Gln Ser Ile
1               5                   10                  15

Ala Asn Thr Ser
            20

<210> SEQ ID NO 19
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
<222> LOCATION: (5)..(5)
<223> OTHER INFORMATION: S-pentenylalanine; Linked to S-pentenylalanine
      at position 1
<220> FEATURE:
<221> NAME/KEY: MISC_FEATURE
<222> LOCATION: (13)..(13)
<223> OTHER INFORMATION: R-octenylalanine; Linked to S-pentenylalanine
      at position 20
<220> FEATURE:
<221> NAME/KEY: MISC_FEATURE
<222> LOCATION: (20)..(20)
<223> OTHER INFORMATION: S-pentenylalanine; Linked to R-octenylalanine
      at position 13

<400> SEQUENCE: 19

Ala Ile Lys Glu Ala Leu Gln Arg Phe Ile His Ile Ala Gln Ser Ile
1               5                   10                  15

Ile Asn Thr Ala
            20

<210> SEQ ID NO 20
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
```

```
<222> LOCATION: (5)..(5)
<223> OTHER INFORMATION: S-pentenylalanine; Linked to S-pentenylalanine
      at position 1
<220> FEATURE:
<221> NAME/KEY: MISC_FEATURE
<222> LOCATION: (9)..(9)
<223> OTHER INFORMATION: S-pentenylalanine; Linked to S-pentenylalanine
      at position 13
<220> FEATURE:
<221> NAME/KEY: MISC_FEATURE
<222> LOCATION: (13)..(13)
<223> OTHER INFORMATION: S-pentenylalanine; Linked to S-pentenylalanine
      at position 9
<220> FEATURE:
<221> NAME/KEY: MISC_FEATURE
<222> LOCATION: (18)..(18)
<223> OTHER INFORMATION: D stereochemical configuration
<220> FEATURE:
<221> NAME/KEY: MISC_FEATURE
<222> LOCATION: (19)..(19)
<223> OTHER INFORMATION: D stereochemical configuration
<220> FEATURE:
<221> NAME/KEY: MISC_FEATURE
<222> LOCATION: (20)..(20)
<223> OTHER INFORMATION: D stereochemical configuration

<400> SEQUENCE: 20

Ala Ile Lys Glu Ala Leu Gln Arg Ala Ile His Ile Ala Gln Ser Ile
1               5                   10                  15

Ile Asn Thr Ser
            20

<210> SEQ ID NO 21
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
<222> LOCATION: (5)..(5)
<223> OTHER INFORMATION: S-pentenylalanine; Linked to S-pentenylalanine
      at position 1
<220> FEATURE:
<221> NAME/KEY: MISC_FEATURE
<222> LOCATION: (9)..(9)
<223> OTHER INFORMATION: R-octenylalanine; Linked to S-pentenylalanine
      at position 16
<220> FEATURE:
<221> NAME/KEY: MISC_FEATURE
<222> LOCATION: (16)..(16)
<223> OTHER INFORMATION: S-pentenylalanine; Linked to R-octenylalanine
      at position 9
<220> FEATURE:
<221> NAME/KEY: MISC_FEATURE
<222> LOCATION: (18)..(18)
<223> OTHER INFORMATION: D stereochemical configuration
<220> FEATURE:
<221> NAME/KEY: MISC_FEATURE
<222> LOCATION: (19)..(19)
<223> OTHER INFORMATION: D stereochemical configuration
<220> FEATURE:
<221> NAME/KEY: MISC_FEATURE
<222> LOCATION: (20)..(20)
<223> OTHER INFORMATION: D stereochemical configuration

<400> SEQUENCE: 21

Ala Ile Lys Glu Ala Leu Gln Arg Ala Ile His Ile Val Gln Ser Ala
1               5                   10                  15
```

Ile Asn Thr Ser
            20

<210> SEQ ID NO 22
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: S-pentenylalanine; Linked to S-pentenylalanine
      at position 5
<220> FEATURE:
<221> NAME/KEY: MISC_FEATURE
<222> LOCATION: (5)..(5)
<223> OTHER INFORMATION: S-pentenylalanine; Linked to S-pentenylalanine
      at position 1
<220> FEATURE:
<221> NAME/KEY: MISC_FEATURE
<222> LOCATION: (13)..(13)
<223> OTHER INFORMATION: S-pentenylalanine; Linked to S-pentenylalanine
      at position 17
<220> FEATURE:
<221> NAME/KEY: MISC_FEATURE
<222> LOCATION: (17)..(17)
<223> OTHER INFORMATION: S-pentenylalanine; Linked to S-pentenylalanine
      at position 13
<220> FEATURE:
<221> NAME/KEY: MISC_FEATURE
<222> LOCATION: (18)..(18)
<223> OTHER INFORMATION: D stereochemical configuration
<220> FEATURE:
<221> NAME/KEY: MISC_FEATURE
<222> LOCATION: (19)..(19)
<223> OTHER INFORMATION: D stereochemical configuration
<220> FEATURE:
<221> NAME/KEY: MISC_FEATURE
<222> LOCATION: (20)..(20)
<223> OTHER INFORMATION: D stereochemical configuration

<400> SEQUENCE: 22

Ala Ile Lys Glu Ala Leu Gln Arg Phe Ile His Ile Ala Gln Ser Ile
1               5                   10                  15

Ala Asn Thr Ser
            20

<210> SEQ ID NO 23
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
<222> LOCATION: (3)..(3)
<223> OTHER INFORMATION: X = Any amino acid
<220> FEATURE:
<221> NAME/KEY: MISC_FEATURE
<222> LOCATION: (4)..(4)
<223> OTHER INFORMATION: S-pentenylalanine; Linked to S-pentenylalanine
      at position 8
<220> FEATURE:
<221> NAME/KEY: MISC_FEATURE
<222> LOCATION: (5)..(5)
<223> OTHER INFORMATION: X = Any amino acid

```
<220> FEATURE:
<221> NAME/KEY: MISC_FEATURE
<222> LOCATION: (6)..(6)
<223> OTHER INFORMATION: X = Any amino acid
<220> FEATURE:
<221> NAME/KEY: MISC_FEATURE
<222> LOCATION: (7)..(7)
<223> OTHER INFORMATION: X = Any amino acid
<220> FEATURE:
<221> NAME/KEY: MISC_FEATURE
<222> LOCATION: (8)..(8)
<223> OTHER INFORMATION: S-pentenylalanine; Linked to S-pentenylalanine
      at position 4
<220> FEATURE:
<221> NAME/KEY: MISC_FEATURE
<222> LOCATION: (9)..(9)
<223> OTHER INFORMATION: X = Any amino acid
<220> FEATURE:
<221> NAME/KEY: MISC_FEATURE
<222> LOCATION: (10)..(10)
<223> OTHER INFORMATION: X = Any amino acid

<400> SEQUENCE: 23

Xaa Xaa Xaa Ala Xaa Xaa Xaa Ala Xaa Xaa
1               5                   10

<210> SEQ ID NO 24
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
<222> LOCATION: (3)..(3)
<223> OTHER INFORMATION: R-octenylalanine; Linked to S-pentenylalanine
      at position 10
<220> FEATURE:
<221> NAME/KEY: MISC_FEATURE
<222> LOCATION: (4)..(4)
<223> OTHER INFORMATION: X = Any amino acid
<220> FEATURE:
<221> NAME/KEY: MISC_FEATURE
<222> LOCATION: (5)..(5)
<223> OTHER INFORMATION: X = Any amino acid
<220> FEATURE:
<221> NAME/KEY: MISC_FEATURE
<222> LOCATION: (6)..(6)
<223> OTHER INFORMATION: X = Any amino acid
<220> FEATURE:
<221> NAME/KEY: MISC_FEATURE
<222> LOCATION: (7)..(7)
<223> OTHER INFORMATION: X = Any amino acid
<220> FEATURE:
<221> NAME/KEY: MISC_FEATURE
<222> LOCATION: (8)..(8)
<223> OTHER INFORMATION: X = Any amino acid
<220> FEATURE:
<221> NAME/KEY: MISC_FEATURE
<222> LOCATION: (9)..(9)
<223> OTHER INFORMATION: X = Any amino acid
<220> FEATURE:
<221> NAME/KEY: MISC_FEATURE
<222> LOCATION: (10)..(10)
<223> OTHER INFORMATION: S-pentenylalanine; Linked to R-octenylalanine
      at position 3
<220> FEATURE:
<221> NAME/KEY: MISC_FEATURE
<222> LOCATION: (11)..(11)
```

<223> OTHER INFORMATION: X = Any amino acid

<400> SEQUENCE: 24

Xaa Xaa Ala Xaa Xaa Xaa Xaa Xaa Xaa Ala Xaa
1               5                   10

<210> SEQ ID NO 25
<211> LENGTH: 708
<212> TYPE: DNA
<213> ORGANISM: Homo sapiens

<400> SEQUENCE: 25

```
atggccttac cagtgaccgc cttgctcctg ccgctggcct tgctgctcca cgccgccagg      60
ccgagccagt tccgggtgtc gccgctggat cggacctgga acctgggcga cagtggag       120
ctgaagtgcc aggtgctgct gtccaacccg acgtcgggct gctcgtggct cttccagccg    180
cgcggcgccg ccgccagtcc caccttcctc ctatacctct cccaaaacaa gcccaaggcg    240
gccgaggggc tggacaccca gcggttctcg ggcaagaggt tggggacac cttcgtcctc     300
accctgagcg acttccgccg agagaacgag ggctactatt tctgctcggc cctgagcaac    360
tccatcatgt acttcagcca cttcgtgccg gtcttcctgc cagcgaagcc accacgacg     420
ccagcgccgc gaccaccaac accggcgccc accatcgcgt cgcagcccct gtcctgcgc     480
ccagaggcgt gccggccagc ggcgggggc gcagtgcaca cgagggggct ggacttcgcc    540
tgtgatatct acatctgggc gcccttggcc gggacttgtg gggtccttct cctgtcactg    600
gttatcaccc tttactgcaa ccacaggaac cgaagacgtg tttgcaaatg tccccggcct    660
gtggtcaaat cgggagacaa gcccagcctt tcggcgagat acgtctaa              708
```

<210> SEQ ID NO 26
<211> LENGTH: 235
<212> TYPE: PRT
<213> ORGANISM: Homo sapiens

<400> SEQUENCE: 26

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Ser Leu Val Ile Thr Leu Tyr Cys Asn His
        195                 200                 205

Arg Asn Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 27
<211> LENGTH: 732
<212> TYPE: DNA
<213> ORGANISM: Homo sapiens

<400> SEQUENCE: 27

| | | | | | |
|---|---|---|---|---|---|
| atgcggccgc | ggctgtggct | cctcttggcc | gcgcagctga | cagttctcca | tggcaactca | 60 |
| gtcctccagc | agaccctgc | atacataaag | gtgcaaacca | caagatggt | gatgctgtcc | 120 |
| tgcgaggcta | aaatctccct | cagtaacatg | cgcatctact | ggctgagaca | gcgccaggca | 180 |
| ccgagcagtg | acagtcacca | cgagttcctg | gccctctggg | attccgcaaa | agggactatc | 240 |
| cacggtgaag | aggtggaaca | ggagaagata | gctgtgtttc | gggatgcaag | ccggttcatt | 300 |
| ctcaatctca | caagcgtgaa | gccggaagac | agtggcatct | acttctgcat | gatcgtcggg | 360 |
| agccccgagc | tgaccttcgg | gaagggaact | cagctgagtg | tggttgattt | ccttcccacc | 420 |
| actgcccagc | ccaccaagaa | gtccaccctc | aagaagagag | tgtgccggtt | acccaggcca | 480 |
| gagacccaga | agggcccact | ttgtagcccc | atcacccttg | gcctgctggt | ggctggcgtc | 540 |
| ctggttctgc | tggtttccct | gggagtggcc | atccacctgt | gctgccggcg | gaggagagcc | 600 |
| cggcttcgtt | tcatgaaaca | gcctcaaggg | gaaggtatat | caggaacctt | tgtccccaa | 660 |
| tgcctgcatg | gatactacag | caatactaca | acctcacaga | agctgcttaa | cccatggatc | 720 |
| ctgaaaacat | ag | | | | | 732 |

<210> SEQ ID NO 28
<211> LENGTH: 243
<212> TYPE: PRT
<213> ORGANISM: Homo sapiens

<400> SEQUENCE: 28

Met Arg Pro Arg Leu Trp Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
            130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Val Ser Leu Gly Val Ala Ile His
                180                 185                 190

Leu Cys Cys Arg Arg Arg Ala Arg Leu Arg Phe Met Lys Gln Pro
                195                 200                 205

Gln Gly Glu Gly Ile Ser Gly Thr Phe Val Pro Gln Cys Leu His Gly
            210                 215                 220

Tyr Tyr Ser Asn Thr Thr Thr Ser Gln Lys Leu Leu Asn Pro Trp Ile
225                 230                 235                 240

Leu Lys Thr

<210> SEQ ID NO 29
<211> LENGTH: 462
<212> TYPE: DNA
<213> ORGANISM: Homo sapiens

<400> SEQUENCE: 29

```
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat tacaagaatc ccaaactcac caggatgctc     180
acatttaagt tttacatgcc caagaaggcc acagaactga acatcttca gtgtctagaa      240
gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                       462
```

<210> SEQ ID NO 30
<211> LENGTH: 153
<212> TYPE: PRT
<213> ORGANISM: Homo sapiens

<400> SEQUENCE: 30

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

```
Asp Glu Thr Ala Thr Ile Val Glu Phe Leu Asn Arg Trp Ile Thr Phe
            130                 135                 140

Cys Gln Ser Ile Ile Ser Thr Leu Thr
145                 150
```

<210> SEQ ID NO 31
<211> LENGTH: 489
<212> TYPE: DNA
<213> ORGANISM: Homo sapiens

<400> SEQUENCE: 31

```
atgagaattt cgaaaccaca tttgagaagt atttccatcc agtgctactt gtgtttactt     60
ctaaacagtc attttctaac tgaagctggc attcatgtct tcattttggg ctgtttcagt    120
gcagggcttc ctaaaacaga agccaactgg gtgaatgtaa taagtgattt gaaaaaaatt    180
gaagatctta ttcaatctat gcatattgat gctactttat atacggaaag tgatgttcac    240
cccagttgca agtaacagc aatgaagtgc tttctcttgg agttacaagt tatttcactt    300
gagtccggag atgcaagtat tcatgataca gtagaaaatc tgatcatcct agcaaacaac    360
agtttgtctt ctaatgggaa tgtaacagaa tctggatgca agaatgtga ggaactggag    420
gaaaaaaata ttaagaatt tttgcagagt tttgtacata ttgtccaaat gttcatcaac    480
acttcttga                                                           489
```

<210> SEQ ID NO 32
<211> LENGTH: 162
<212> TYPE: PRT
<213> ORGANISM: Homo sapiens

<400> SEQUENCE: 32

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 33
<211> LENGTH: 702
<212> TYPE: DNA
<213> ORGANISM: Homo sapiens

<400> SEQUENCE: 33

```
atggataacc aaggagtaat ctactcagac ctgaatctgc ccccaaaccc aaagaggcag      60
caacgaaaac ctaaaggcaa taaagctcc  attttagcaa ctgaacagga ataacctat     120
gcggaattaa accttcaaaa agcttctcag gattttcaag ggaatgacaa aacctatcac    180
tgcaaagatt taccatcagc tccagagaag ctcattgttg ggatcctggg aattatctgt    240
cttatcttaa tggcctctgt ggtaacgata gttgttattc cctctacatt aatacagagg    300
cacaacaatt cttccctgaa tacaagaact cagaaagcac gtcattgtgg ccattgtcct    360
gaggagtgga ttacatattc caacagttgt tactacattg gtaaggaaag aagaacttgg    420
gaagagagtt tgctggcctg tacttcgaag aactccagtc tgctttctat agataatgaa    480
gaagaaatga atttctgtc  catcatttca ccatcctcat ggattggtgt gtttcgtaac    540
agcagtcatc atccatgggt gacaatgaat ggtttggctt tcaaacatga gataaaagac    600
tcagataatg ctgaacttaa ctgtgcagtg ctacaagtaa atcgacttaa atcagcccag    660
tgtggatctt caataatata tcattgtaag cataagcttt ag                       702
```

<210> SEQ ID NO 34
<211> LENGTH: 233
<212> TYPE: PRT
<213> ORGANISM: Homo sapiens

<400> SEQUENCE: 34

```
Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
    210                 215                 220

Ile Ile Tyr His Cys Lys His Lys Leu
225                 230
```

```
<210> SEQ ID NO 35
<211> LENGTH: 648
<212> TYPE: DNA
<213> ORGANISM: Homo sapiens

<400> SEQUENCE: 35
atggataacc aaggagtaat ctactcagac ctgaatctgc ccccaaaccc aaagaggcag      60
caacgaaaac ctaaaggcaa taaaagctcc attttagcaa ctgaacagga ataacctat     120 gcggaattaa accttcaaaa agcttctcag gattttcaag ggaatgacaa aacctatcac    180
tgcaaagatt taccatcagc tccagagaag ctcattgttg ggatcctggg aattatctgt    240
cttatcttaa tggcctctgt ggtaacgata gttgttattc cctcacgtca ttgtggccat    300
tgtcctgagg agtggattac atattccaac agttgttact acattggtaa ggaaagaaga    360
acttgggaag agagtttgct ggcctgtact tcgaagaact ccagtctgct ttctatagat    420
aatgaagaag aaatgaaatt tctgtccatc atttcaccat cctcatggat tggtgtgttt    480
cgtaacagca gtcatcatcc atgggtgaca atgaatggtt tggctttcaa acatgagata    540
aaagactcag ataatgctga acttaactgt gcagtgctac aagtaaatcg acttaaatca    600
gcccagtgtg gatcttcaat aatatatcat tgtaagcata agctttag                 648

<210> SEQ ID NO 36
<211> LENGTH: 215
<212> TYPE: PRT
<213> ORGANISM: Homo sapiens

<400> SEQUENCE: 36

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Arg
                85                  90                  95

His Cys Gly His Cys Pro Glu Glu Trp Ile Thr Tyr Ser Asn Ser Cys
            100                 105                 110

Tyr Tyr Ile Gly Lys Glu Arg Arg Thr Trp Glu Glu Ser Leu Leu Ala
        115                 120                 125

Cys Thr Ser Lys Asn Ser Ser Leu Leu Ser Ile Asp Asn Glu Glu Glu
    130                 135                 140

Met Lys Phe Leu Ser Ile Ile Ser Pro Ser Ser Trp Ile Gly Val Phe
145                 150                 155                 160

Arg Asn Ser Ser His His Pro Trp Val Thr Met Asn Gly Leu Ala Phe
                165                 170                 175

Lys His Glu Ile Lys Asp Ser Asp Asn Ala Glu Leu Asn Cys Ala Val
            180                 185                 190

Leu Gln Val Asn Arg Leu Lys Ser Ala Gln Cys Gly Ser Ser Ile Ile
        195                 200                 205

Tyr His Cys Lys His Lys Leu
    210                 215
```

<210> SEQ ID NO 37
<211> LENGTH: 696
<212> TYPE: DNA
<213> ORGANISM: Homo sapiens

<400> SEQUENCE: 37

```
atgaataaac aaagaggaac cttctcagaa gtgagtctgg cccaggaccc aaagcggcag      60
caaaggaaac ctaaaggcaa taaaagctcc atttcaggaa ccgaacagga aatattccaa     120
gtagaattaa atcttcaaaa tccttccctg aatcatcaag ggattgataa atatatgac      180
tgccaaggtt tactgccacc tcagagaag ctcactgccg aggtcctagg aatcatttgc      240
attgtcctga tggccactgt gttaaaaaca atagttctta ttcctttcct ggagcagaac     300
aattttccc cgaatacaag aacgcagaaa gcacgtcatt gtggccattg tcctgaggag     360
tggattacat attccaacag ttgttattac attggtaagg aaagaagaac ttgggaagag     420
agtttgctgg cctgtacttc gaagaactcc agtctgcttt ctatagataa tgaagaagaa     480
atgaaatttc tggccagcat tttaccttcc tcatggattg gtgtgtttcg taacagcagt     540
catcatccat gggtgacaat aaatggtttg gctttcaaac ataagataaa agactcagat     600
aatgctgaac ttaactgtgc agtgctacaa gtaaatcgac ttaaatcagc ccagtgtgga     660
tcttcaatga tatatcattg taagcataag ctttag                              696
```

<210> SEQ ID NO 38
<211> LENGTH: 231
<212> TYPE: PRT
<213> ORGANISM: Homo sapiens

<400> SEQUENCE: 38

```
Met Asn Lys Gln Arg Gly Thr Phe Ser Glu Val Ser Leu Ala Gln Asp
1               5                   10                  15

Pro Lys Arg Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Pro
        35                  40                  45

Ser Leu Asn His Gln Gly Ile Asp Lys Ile Tyr Asp Cys Gln Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Phe Ser Pro Asn Thr Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Leu Ala
    130                 135                 140

Cys Thr Ser Lys Asn Ser Ser Leu Leu Ser Ile Asp Asn Glu Glu Glu
145                 150                 155                 160

Met Lys Phe Leu Ala Ser Ile Leu Pro Ser Ser Trp Ile Gly Val Phe
                165                 170                 175

Arg Asn Ser Ser His His Pro Trp Val Thr Ile Asn Gly Leu Ala Phe
            180                 185                 190

Lys His Lys Ile Lys Asp Ser Asp Asn Ala Glu Leu Asn Cys Ala Val
        195                 200                 205
```

-continued

Leu Gln Val Asn Arg Leu Lys Ser Ala Gln Cys Gly Ser Ser Met Ile
210                 215                 220

Tyr His Cys Lys His Lys Leu
225                 230

<210> SEQ ID NO 39
<211> LENGTH: 651
<212> TYPE: DNA
<213> ORGANISM: Homo sapiens

<400> SEQUENCE: 39

```
atgggggtgga ttcgtggtcg gaggtctcga cacagctggg agatgagtga atttcataat      60
tataacttgg atctgaagaa gagtgatttt tcaacacgat ggcaaaagca agatgtcca      120
gtagtcaaaa gcaaatgtag agaaaatgca tctccatttt ttttctgctg cttcatcgct      180
gtagccatgg gaatccgttt cattattatg gtaacaatat ggagtgctgt attcctaaac      240
tcattattca accaagaagt tcaaattccc ttgaccgaaa gttactgtgg cccatgtcct      300
aaaaactgga tatgttacaa aaataactgc taccaatttt ttgatgagag taaaaactgg      360
tatgagagcc aggcttcttg tatgtctcaa aatgccagcc ttctgaaagt atacagcaaa      420
gaggaccagg atttacttaa actggtgaag tcatatcatt ggatgggact agtacacatt      480
ccaacaaatg gatcttggca gtgggaagat ggctccattc tctcacccaa cctactaaca      540
ataattgaaa tgcagaaggg agactgtgca ctctatgcct cgagctttaa aggctatata      600
gaaaactgtt caactccaaa tacgtacatc tgcatgcaaa ggactgtgta a            651
```

<210> SEQ ID NO 40
<211> LENGTH: 216
<212> TYPE: PRT
<213> ORGANISM: Homo sapiens

<400> SEQUENCE: 40

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45

Asn Ala Ser Pro Phe Phe Phe Cys Cys Phe Ile Ala Val Ala Met Gly
        50                  55                  60

Ile Arg Phe Ile Ile Met Val Thr Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
            195                 200                 205

Tyr Ile Cys Met Gln Arg Thr Val
    210                 215

<210> SEQ ID NO 41
<211> LENGTH: 723
<212> TYPE: DNA
<213> ORGANISM: Homo sapiens

<400> SEQUENCE: 41

```
atgagtaaac aaagaggaac cttctcagaa gtgagtctgg cccaggaccc aaagtggcag    60
caaaggaaac ctaaaggcaa taaaagctcc atttcaggaa ccgaacagga aatattccaa   120
gtagaattaa accttcaaaa tgcttctctg aatcatcaag ggattgataa aatatatgac   180
tgccaaggtt tactgccacc tccagaaaag ctcactgccg aggtcctagg aatcatttgc   240
attgtcctga tggccactgt gttaaaaaca atagttctta ttccttcct ggagcagaac   300 aattcttccc cgaatgcaag aacccagaaa gcacgtcatt gtggccattg tcctgaggag   360
tggattacat attccaacag ttgttattac attggtaagg aaagaagaac ttgggaagag   420
agtttgcagg cctgtgcttc aaagaactct tctagtctgc tttgtataga taatgaagaa   480
gaaatgaaat ttctggccag cattttacct tcctcatgga ttggtgtgtt tcgtaacagc   540
agtcatcatc catgggtgac aataaatggt ttggctttca acatgagat aaaagactca   600 gatcatgctg aacgtaactg tgcaatgcta catgtacgtg gacttatatc agaccagtgt   660
ggatcttcaa gaatcattag acggggtttc atcatgttga ccaggctggt cttgaactcc   720
tga                                                                723
```

<210> SEQ ID NO 42
<211> LENGTH: 240
<212> TYPE: PRT
<213> ORGANISM: Homo sapiens

<400> SEQUENCE: 42

Met Ser Lys Gln Arg Gly Thr Phe Ser Glu Val Ser Leu Ala Gln Asp
1               5                   10                  15

Pro Lys Trp Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Ala
        35                  40                  45

Ser Leu Asn His Gln Gly Ile Asp Lys Ile Tyr Asp Cys Gln Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Ser Ser Pro Asn Ala Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Gln Ala
    130                 135                 140

Cys Ala Ser Lys Asn Ser Ser Ser Leu Leu Cys Ile Asp Asn Glu Glu
145                 150                 155                 160

```
Glu Met Lys Phe Leu Ala Ser Ile Leu Pro Ser Ser Trp Ile Gly Val
            165                 170                 175

Phe Arg Asn Ser Ser His His Pro Trp Val Thr Ile Asn Gly Leu Ala
            180                 185                 190

Phe Lys His Glu Ile Lys Asp Ser Asp His Ala Glu Arg Asn Cys Ala
            195                 200                 205

Met Leu His Val Arg Gly Leu Ile Ser Asp Gln Cys Gly Ser Ser Arg
        210                 215                 220

Ile Ile Arg Arg Gly Phe Ile Met Leu Thr Arg Leu Val Leu Asn Ser
225                 230                 235                 240

<210> SEQ ID NO 43
<211> LENGTH: 477
<212> TYPE: DNA
<213> ORGANISM: Homo sapiens

<400> SEQUENCE: 43
atgaataaac aaagaggaac ctactcagaa gtgagtctgg cccaggaccc aaagaggcag      60
caaaggaaac ttaagggcaa taaaatctcc atttcaggaa ccaaacagga atattccaa     120 gtagaattaa accttcaaaa tgcttcttcg gatcatcaag ggaatgacaa acatatcac     180 tgcaaaggtt tactgccacc tccagagaag ctcactgctg aggtcctagg aatcatttgc     240
attgtcctga tggccactgt gttaaaaaca atagttctta ttccttgtat tggagtactg     300
gagcagaaca attttttccct gaatagaaga atgcagaaag cacgtcattg tggccattgt     360
cctgaggagt ggattacata ttccaacagt tgttattaca ttggtaagga agaagaact     420 tgggaagaaa gagtttgctg gcctgtgctt cgaagaactc tgatctgctt tctatag       477

<210> SEQ ID NO 44
<211> LENGTH: 158
<212> TYPE: PRT
<213> ORGANISM: Homo sapiens

<400> SEQUENCE: 44

Met Asn Lys Gln Arg Gly Thr Tyr Ser Glu Val Ser Leu Ala Gln Asp
1               5                   10                  15

Pro Lys Arg Gln Gln Arg Lys Leu Lys Gly Asn Lys Ile Ser Ile Ser
            20                  25                  30

Gly Thr Lys Gln Glu Ile Phe Gln Val Glu Leu Asn Leu Gln Asn Ala
        35                  40                  45

Ser Ser Asp His Gln Gly Asn Asp Lys Thr Tyr His Cys Lys Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Cys
                85                  90                  95

Ile Gly Val Leu Glu Gln Asn Asn Phe Ser Leu Asn Arg Arg Met Gln
            100                 105                 110

Lys Ala Arg His Cys Gly His Cys Pro Glu Glu Trp Ile Thr Tyr Ser
        115                 120                 125

Asn Ser Cys Tyr Tyr Ile Gly Lys Glu Arg Arg Thr Trp Glu Arg
    130                 135                 140

Val Cys Trp Pro Val Leu Arg Arg Thr Leu Ile Cys Phe Leu
145                 150                 155

<210> SEQ ID NO 45
```

```
<211> LENGTH: 774
<212> TYPE: DNA
<213> ORGANISM: Homo sapiens

<400> SEQUENCE: 45
atgagtaaac aaagaggaac cttctcagaa gtgagtctgg cccaggaccc aaagtggcag      60
caaaggaaac ctaaaggcaa taaaagctcc atttcaggaa ccgaacagga aatattccaa     120
gtagaattaa accttcaaaa tgcttctctg aatcatcaag ggattgataa aatatatgac     180
tgccaaggtt tactgccacc tccagaaaag ctcactgccg aggtcctagg aatcatttgc     240
attgtcctga tggccactgt gttaaaaaca atagttctta ttccttcct ggagcagaac     300 aattcttccc cgaatgcaag aacccagaaa gcacgtcatt gtggccattg tcctgaggag     360
tggattacat attccaacag ttgttattac attggtaagg aaagaagaac ttgggaagag     420
agtttgcagg cctgtgcttc aaagaactct tctagtctgc tttgtataga taatgaagaa     480
gaaatgaaat ttctggccag cattttacct tcctcatgga ttggtgtgtt tcgtaacagc     540
agtcatcatc catgggtgac aataaatggt ttggctttca acatgagat aaaagactca     600 gatcatgctg aacgtaactg tgcaatgcta catgtacgtg gacttatatc agaccagtgt     660
ggatcttcaa gaatcattgt gagcataagc tttagaatta aagcgcttga gcttgcagtg     720
catcagataa aattttatat ttgttcaaac agaaatgata ttatgattgc ataa          774

<210> SEQ ID NO 46
<211> LENGTH: 257
<212> TYPE: PRT
<213> ORGANISM: Homo sapiens

<400> SEQUENCE: 46
```

Met Ser Lys Gln Arg Gly Thr Phe Ser Glu Val Ser Leu Ala Gln Asp
1               5                   10                  15

Pro Lys Trp Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Ala
        35                  40                  45

Ser Leu Asn His Gln Gly Ile Asp Lys Ile Tyr Asp Cys Gln Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Ser Ser Pro Asn Ala Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Gln Ala
    130                 135                 140

Cys Ala Ser Lys Asn Ser Ser Ser Leu Leu Cys Ile Asp Asn Glu Glu
145                 150                 155                 160

Glu Met Lys Phe Leu Ala Ser Ile Leu Pro Ser Ser Trp Ile Gly Val
                165                 170                 175

Phe Arg Asn Ser Ser His His Pro Trp Val Thr Ile Asn Gly Leu Ala
            180                 185                 190

Phe Lys His Glu Ile Lys Asp Ser Asp His Ala Glu Arg Asn Cys Ala
        195                 200                 205

```
-continued

Met Leu His Val Arg Gly Leu Ile Ser Asp Gln Cys Gly Ser Ser Arg
    210             215             220

Ile Ile Val Ser Ile Ser Phe Arg Ile Lys Ala Leu Glu Leu Ala Val
225             230             235             240

His Gln Ile Lys Phe Tyr Ile Cys Ser Asn Arg Asn Asp Ile Met Ile
            245             250             255

Ala
```